US012799217B2

(12) United States Patent
Zhang et al.

(10) Patent No.: US 12,799,217 B2
(45) **Date of Patent: *Nov. 17, 2026**

(54) GIPR ANTIBODY AND FUSION PROTEIN BETWEEN SAME AND GLP-1, AND PHARMACEUTICAL COMPOSITION AND APPLICATION THEREOF

(71) Applicant: GMAX BIOPHARM LLC, Hangzhou (CN)

(72) Inventors: Hua Zhang, Hangzhou (CN); Xiaofeng Wang, Hangzhou (CN); Chenjiang Yao, Hangzhou (CN); Cheng Zhang, Hangzhou (CN); Shuqian Jing, Hangzhou (CN)

(73) Assignee: GMAX BIOPHARM LLC, Hangzhou (CN)

( * ) Notice: Subject to any disclaimer, the term of this patent is extended or adjusted under 35 U.S.C. 154(b) by 1065 days.

This patent is subject to a terminal disclaimer.

(21) Appl. No.: 17/761,128

(22) PCT Filed: Sep. 16, 2020

(86) PCT No.: PCT/CN2020/115483

§ 371 (c)(1),
(2) Date: Mar. 16, 2022

(87) PCT Pub. No.: WO2021/052349

PCT Pub. Date: Mar. 25, 2021

(65) Prior Publication Data

US 2022/0411520 A1 Dec. 29, 2022

(30) Foreign Application Priority Data

Sep. 18, 2019 (CN) ........................ 201910882351.2

(51) Int. Cl.
*C07K 16/28* (2006.01)
*A61P 1/16* (2006.01)
*C07K 14/605* (2006.01)

(52) U.S. Cl.
CPC ............ *C07K 16/2869* (2013.01); *A61P 1/16* (2018.01); *C07K 14/605* (2013.01); *C07K 2317/24* (2013.01); *C07K 2317/33* (2013.01); *C07K 2317/565* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 11,780,916 B2 * | 10/2023 | Wang | C07K 14/605 | 424/133.1 |
| 2017/0275370 A1 | 9/2017 | Yie et al. | | |
| 2021/0061904 A1 * | 3/2021 | Wang | A61P 3/04 | |

FOREIGN PATENT DOCUMENTS

| | | | |
|---|---|---|---|
| CN | 109715662 | A | 5/2019 |
| JP | 2016532448 | A | 10/2016 |
| JP | 2019504032 | A | 2/2019 |
| JP | 7313372 | B | 7/2023 |
| KR | 10-2016-0055789 | A | 5/2016 |
| KR | 10-2018-0108602 | A | 10/2018 |
| TW | I832847 | B | 2/2024 |
| WO | WO 2017112824 | A2 | 6/2017 |
| WO | WO 2018136440 | A1 | 7/2018 |
| WO | WO 2018237095 | A1 | 12/2018 |
| WO | WO 2018237097 | A1 | 12/2018 |
| WO | WO 2019179424 | A1 | 9/2019 |

OTHER PUBLICATIONS

Ravn P et al, Structural and Pharmacological Characterization of Novel Potent and Selective Monoclonal Antibody Antagonists of Glucose-dependent Insulinotropic Polypeptide Receptor, Journal of Biological Chemistry, 2013, vol. 288 No. 27, 19760-19772.
Lewis JT et al, Glucose-Dependent Insulinotropic Polypeptide Confers Early Phase Insulin Release to Oral Glucose in Rats: Demonstration by a Receptor Antagonist, Endocrinology, 2000, vol. 141 No. 10, 3710-3716.
Office Action for TW109132123, mailed on Jul. 26, 2024.
Structural and Pharmacological Characterization of Novel Potent and Selective Monoclonal Antibody Antagonists of Glucose-dependent Insulinotropic Polypeptide Receptor, Ravn, Peter et al., Journal of Biological Chemistry, vol. 288, Issue 27, 19760-19772.

* cited by examiner

*Primary Examiner* — Marianne P Allen
(74) *Attorney, Agent, or Firm* — MARSHALL, GERSTEIN & BORUN LLP

(57) ABSTRACT

Provided herein are a gastric inhibitory polypeptide receptor (GIPR) antibody and its fusion protein with glucagon-like peptide-1 (GLP-1), and a pharmaceutical composition thereof. Also provided herein is a method for using the GIPR antibody and its fusion protein with GLP-1 to treat, prevent or improve one or more symptoms of non-alcoholic fatty liver disease, non-alcoholic steatohepatitis, type 2 diabetes or obesity.

22 Claims, 9 Drawing Sheets

Specification includes a Sequence Listing.

GIPR ANTIBODY AND FUSION PROTEIN BETWEEN SAME AND GLP-1, AND PHARMACEUTICAL COMPOSITION AND APPLICATION THEREOF

CROSS-REFERENCE TO RELATED APPLICATIONS

This application is a U.S. national stage of International Patent Application No. PCT/CN2020/115483, filed Sep. 16, 2020, which claims the priority to Chinese Patent Application No. 201910882351.2, filed Sep. 18, 2019, the disclosure of each of which is incorporated by reference herein in its entirety.

SEQUENCE LISTING

This application incorporates by reference in its entirety the Computer Readable Form of a Sequence Listing in ASCII text format submitted via EFS-Web. The Sequence Listing text file submitted via EFS-Web entitled "087222-8016US01 Amended SeqL_ST25", was created on Jan. 28, 2026 and is 118,499 bytes in size.

FIELD

Provided herein are an antibody specifically binding to GIPR and its fusion protein with GLP-1, and a pharmaceutical composition thereof. Also provided herein is a method for using the GIPR antibody and its fusion protein with GLP-1 to treat, prevent or improve one or more symptoms of non-alcoholic fatty liver disease, non-alcoholic steatohepatitis, type 2 diabetes or obesity.

BACKGROUND

Intestinal gastric inhibitory polypeptide (GIP) is a polypeptide hormone secreted by intestinal K cells after feeding, and includes two isoforms of 42- and 30-amino acid peptides. GIP takes part in the physiological process of insulin secretion by activating the gastric inhibitory polypeptide receptor (GIPR) on the surface of pancreatic β cells (Tseng et al., 1996, *J. Clin. Invest.* 98:2440-2445; Ravn et al., 2013, *J. Biol. Chem.* 288:19760-72). Since the classical biological function of GIP is similar to GLP-1, these peptide hormones are collectively called incretins. GIPR is widely distributed in many tissues, including pancreas, bone, heart, stomach, intestine and adipose tissues (Peter et al., 2013, *J. Biol. Chem.* 288:19760-72), and this diverse distribution suggests that the GIP/GIPR pathway has more biological functions than blood glucose regulation. Experimental evidence shows that the GIP/GIPR signaling pathway is at least closely related to lipid metabolism in these tissues (Yip and Wolfe, 2000, *Life Sci.* 66:91-103). Experimental data also shows that there is an increase of blood circulating GIP concentration in obese or diabetic patients (Creutzfeldt et al., 1978, *Diabetologia* 14:15-24; Flatt et al., 1984, *J. Endocrinol.* 101:249-256; Salera et al., 1982, *J. Clin. Endocrinol. Metab.* 55:329-336; Vilsbøll et al., 2003, *J. Clin. Endocrinol. Metab.* 88:2706-2713). After blocking the GIPR signal with a GIPR inhibitor, significant body weight loss, reduction in insulin resistance and even a reversal of type 2 diabetes were observed in obese mice induced by high fat diet (Ravn et al., 2013, *J. Biol. Chem.* 288:19760-72).

The long-acting glucagon-like peptide-1 analogues (GLP-1 analogue) are a new generation and also the most effective type 2 diabetes drug (Tomlinson et al., 2015,

*Expert Opin. Investig. Drugs* 25:1744-7658; Gallwitz, 2015, *Eur. Endocr.* 11:21-25). Long-acting GLP-1 drugs are also being studied in clinical trials for the treatment of nonalcoholic fatty liver disease (NAFLD). Studies show that long-acting GLP-1 drugs have a significant effect on the improvement of liver tissue morphology, the reduction of alanine aminotransferase/glutathione aminotransferase ratio and the liver fat content in patients with NAFLD (Samson et al., 2013, *J. Diabetes Complications* 27:401-6; Portillo-Sanchez and Cusi, 2016, *Clin. Diabetes Endocrinol.* 2:9).

If GLP-1 drugs and GIPR inhibitors can be used together, including the combination or fusion of the two together, this may achieve the effect of simultaneously improving insulin resistance and reducing excessive fat accumulation (obesity). In this regard, blood glucose is reduced and lipid metabolism is interfered, with the GLP-1 part improving glucose metabolism, reducing appetite and body weight and the GIPR antibody part reducing further accumulation of fat and improving liver function. The fat reduction effect of the GIPR antibody and the weight loss effect of the GLP-1 may be used synergistically to treat the non-alcoholic fatty liver disease/non-alcoholic steatohepatitis. This disclosure provides a fusion protein drug that will benefit patients who have one or more diseases of non-alcoholic fatty liver disease/non-alcoholic steatohepatitis, type 2 diabetes and obesity.

SUMMARY

Provided herein is an antibody specifically binding to GIPR, wherein the antibody is an antagonist of GIPR.

Provided herein also is an antibody specifically binding to GIPR, wherein the antibody comprising one, two, three, four, five or six amino acid sequences, wherein each amino acid sequence is independently selected from the amino acid sequences listed below:

a. Light chain CDR1 amino acid sequence: SEQ ID NO: 1, SEQ ID NO: 4, SEQ ID NO: 7, SEQ ID NO: 10, SEQ ID NO: 13, and SEQ ID NO: 15;
b. Light chain CDR2 amino acid sequence: SEQ ID NO: 2, SEQ ID NO: 5, SEQ ID NO: 8, SEQ ID NO: 11, and SEQ ID NO: 16;
c. Light chain CDR3 amino acid sequence: SEQ ID NO: 3, SEQ ID NO: 6, SEQ ID NO: 9, SEQ ID NO: 12, SEQ ID NO: 14, and SEQ ID NO: 17;
d. Heavy chain CDR1 amino acid sequence: SEQ ID NO: 18, SEQ ID NO: 23, and SEQ ID NO: 26;
e. Heavy chain CDR2 amino acid sequence: SEQ ID NO: 19, SEQ ID NO: 21, SEQ ID NO: 24, SEQ ID NO: 27, and SEQ ID NO: 29;
f. Heavy chain CDR3 amino acid sequence: SEQ ID NO: 20, SEQ ID NO: 22, SEQ ID NO: 25, SEQ ID NO: 28, and SEQ ID NO: 30;

Provided herein further is a GLP-1 fusion protein, wherein the fusion protein comprising an antibody specifically binding to GIPR, and one, two, three, four, five, six, seven or eight GLP-1 fragments; the fusion protein connects the carboxy terminal of a GLP-1 fragment with the amino terminal of a light chain or a heavy chain of a GIPR antibody, or connects the amino terminal of a GLP-1 fragment with the carboxy terminal of a light chain or a heavy chain of a GIPR antibody.

Provided herein is a GLP-1 fusion protein, wherein the fusion protein comprising a GIPR antibody and two GLP-1 fragments; the fusion protein connects the carboxy terminal of a GLP-1 fragment with the amino terminal of a light chain of a GIPR antibody: N'-GLP-1-Linker-R-C'; or the carboxy terminal of a GLP-1 fragment connecting to the amino terminal of a heavy chain of a GIPR antibody: N'-GLP-1-Linker-R-C'; wherein: N' represents an amino terminal of fusion protein polypeptide chain, C' represents a carboxy terminal of a fusion protein polypeptide chain, GLP-1 represents a GLP-1 fragment, R is the amino acid sequence of the light chain or heavy chain of a GIPR antibody, and Linker represents a peptide linker.

Provided herein is a polynucleotide encoding a GIPR antibody described herein.

Provided herein is a polynucleotide encoding a fusion protein of GIPR antibody and GLP-1 described herein.

Provided herein is a vector comprising a polynucleotide encoding a GIPR antibody described herein.

Provided herein is a vector comprising a polynucleotide encoding a fusion protein of GIPR antibody and GLP-1 described herein.

Provided herein is a host cell comprising a vector described herein.

Provided herein is a pharmaceutical composition comprising a GIPR antibody described herein and a pharmaceutically acceptable carrier.

Provided herein is a pharmaceutical composition comprising a fusion protein of GIPR antibody and GLP-1 described herein and a pharmaceutically acceptable carrier. Further provided herein is the use of a GIPR antibody described herein in the preparation of a medicament for the treatment, prevention or amelioration of non-alcoholic steatohepatitis diseases.

Provided herein is the use of a fusion protein of GIPR antibody and GLP-1 described herein in the preparation of a medicament for treating, preventing or ameliorating non-alcoholic steatohepatitis diseases.

Provided herein is the use of a GIPR antibody described herein in the preparation of a medicament for treating, preventing or ameliorating type 2 diabetes.

Provided herein is the use of a fusion protein of GIPR antibody and GLP-1 described herein in the preparation of a medicament for treating, preventing or ameliorating type 2 diabetes.

Provided herein is the use of a GIPR antibody described herein in the preparation of a medicament for losing weight or treating, preventing or ameliorating obesity and obesity-related diseases.

Provided herein is the use of a fusion protein of GIPR antibody and GLP-1 described herein in the preparation of a medicament for losing weight or treating, preventing or ameliorating obesity and obesity-related diseases.

Provided herein is the use of a GIPR antibody described herein in the preparation of a medicament for simultaneously treating, preventing or ameliorating two or more diseases of non-alcoholic steatohepatitis diseases, obesity, or type 2 diabetes.

Provided herein is the use of a fusion protein of GIPR antibody and GLP-1 described herein in the preparation of a medicament for simultaneously treating, preventing or ameliorating two or more diseases of non-alcoholic steatohepatitis diseases, obesity, or type 2 diabetes.

Provided herein is a method to treat, prevent, or improve one or more symptoms of non-alcoholic steatohepatitis, comprising giving subjects a therapeutically effective dose of a GIPR antibody described herein.

Provided herein is a method to treat, prevent, or improve one or more symptoms of non-alcoholic steatohepatitis, comprising giving subjects a therapeutically effective dose of a fusion protein of GIPR antibody and GLP-1 described herein.

Provided herein is a method to treat, prevent, or improve one or more symptoms of type 2 diabetes, comprising giving subjects a therapeutically effective dose of a GIPR antibody described herein.

Provided herein is a method to treat, prevent, or improve one or more symptoms of type 2 diabetes, comprising giving subjects a therapeutically effective dose of a fusion protein of GIPR antibody and GLP-1 described herein.

Provided herein is a method to treat, prevent, or improve one or more symptoms of obesity, comprising giving subjects a therapeutically effective dose of a GIPR antibody described herein.

Provided herein is a method to treat, prevent, or improve one or more symptoms of obesity, comprising giving subjects a therapeutically effective dose of a fusion protein of GIPR antibody and GLP-1 described herein.

DETAILED DESCRIPTION

Definitions

Figure 1:
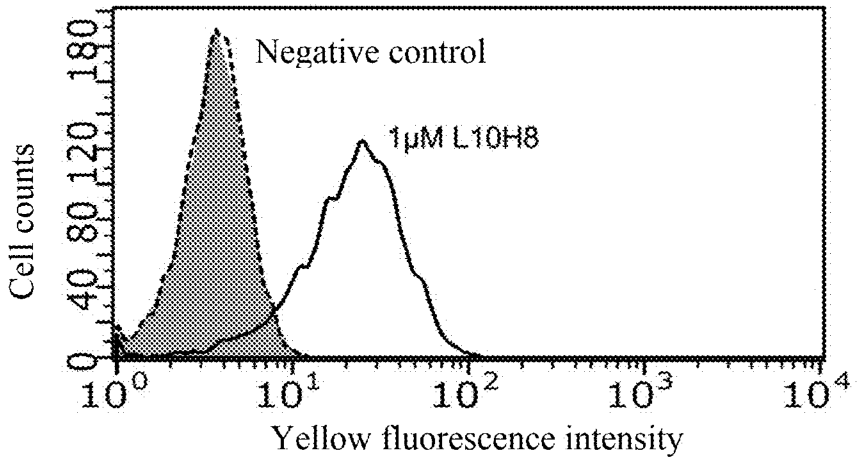
FIG. 1 shows the results of FACS test of the specific binding of the recombinantly expressed hGIPR antibody L10H8 (comprising SEQ ID NO: 70 and SEQ ID NO: 79) to hGIPR. The grey peak and dotted line peak are negative controls, the grey peak represents the background peak of the blank cell CHO-DHFR−, the dotted line peak represents the negative binding peak of L10H8 to the blank cell CHO-DHFR−, and the solid line peak represents the specific binding peak of L10H8 to CHO-DHFR-hGIPR.

Unless defined otherwise herein, scientific and technical terms shall have the meanings understood by ordinary technicians in the field. Generally, the nomenclature and techniques related to pharmacology, biology, biochemistry, cell and tissue culture, biology, molecular biology, immunology, microbiology, genetics and protein nucleic acid chemistry as well as hybridization are well known and commonly used in this field.

This invention used standard single-letter or three-letter abbreviations to indicate polynucleotide and polypeptide sequences. When the polypeptide sequence is written, the first amino acid residue (N') with the amino group is at the far left and the last amino acid residue (C') with the carboxyl group is at the far right, for example, the GLP-1 fragment sequence involved in this invention: SEQ ID NO:105, SEQ ID NO:106, SEQ ID NO: 107, SEQ ID NO:108, and SEQ ID NO:109. Reverse polypeptide sequence refers to a polypeptide sequence wherein amino acids arranged in a reversed order as to the original, for example, the reverse GLP-1 fragment sequences converted from the above GLP-1 fragment sequences: SEQ ID NO: 119, SEQ ID NO: 120, SEQ ID NO: 121, SEQ ID NO: 122, and SEQ ID NO: 123. The 5 'ends of the upstream chains of single-stranded and double-stranded nucleic acid sequences are on the left and their 3' ends are on the right. The specific portion of a polypeptide can be represented by an amino acid residue number, such as amino acids 80 to 130, or represented by the actual residue of the site, such as Lys80 to Lys130. The specific polypeptide or polynucleotide sequence can also be described by explaining its difference from the reference sequence.

The terms "peptide", "polypeptide", and "protein" refer to a molecule containing two or more amino acids that are interlinked by a peptide bond. These terms cover, for example, natural and artificial proteins and peptide analogues of protein sequences (such as mutant proteins, variants and fusion proteins) and proteins that are post-transcriptional or otherwise covalent or non-covalent modified. A peptide, polypeptide, or protein can be a monomer or a polymer.

The term "polypeptide fragment" refers to a polypeptide that has an amino terminus and/or a carboxyl terminus missing from the corresponding full-length protein. For example, the fragment length can be at least 5, 6, 7, 8, 9, 10, 11, 12, 13, 14, 15, 20, 50, 70, 80, 90, 100, 150, or 200 amino acids. The fragment length can be, for example, up to 1000, 750, 500, 250, 200, 175, 150, 125, 100, 90, 80, 70, 60, 50, 40, 30, 20, 15, 14, 13, 12, 11, or 10 amino acids. The fragment may further contain one or more additional amino acids at one end or both, such as amino acid sequences from different natural proteins (e.g., Fc or leucine zipper domains) or artificial amino acid sequences (e.g., artificial joint sequences).

The peptides in this invention include peptides modified for any reason and by any means, For example, by (1) decreasing proteolysis sensitivity, (2) decreasing oxidation sensitivity, (3) altering the affinity for forming protein complexes, (4) altering binding affinity, and (5) conferring or modifying other physicochemical or functional properties. Analogue contains a mutant protein of a polypeptide. For example, can perform single or multiple amino acid substitutions (e.g., conservative amino acid substitutions) in natural sequences (e.g., outside the domain of the polypeptide that forms intramolecular contact). The "conserved amino acid substitution" is the one that does not significantly change the structural characteristics of the parent sequence (e.g., The substitution of amino acids shall not destroy the helices present in the parent sequence or interfere with other secondary structural types necessary to give the parent sequence its properties or function).

A "mutant" of a polypeptide, wherein an amino acid sequence containing the insertion, deletion, and/or replacement of one or more residues in an amino acid sequence relative to another polypeptide sequence. The variants in this invention included fusion proteins.

A "derivative" of a polypeptide is a chemically modified polypeptide, for example, by binding to other chemical components such as polyethylene glycol and albumin (such as human serum albumin), phosphorylation, and glycosylation.

Unless otherwise stated, the term "antibody" includes antibodies with two full-length heavy chains and two full-length light chains, as well as their derivatives, variants, fragments, and mutated proteins. The instances are listed below.

The term "antibody" is a protein that contains the antigen-binding portion and optionally the scaffold or framework portion that allows the antigen-binding portion to adopt a conformation that promotes the binding of the antibody to the antigen. Examples of antibodies include complete antibodies, antibody fragments (such as the antigen-binding portion of an antibody), antibody derivatives, and antibody analogues. The antibody may contain alternative protein scaffolds or artificial scaffolds with transplanted CDRs or derivatives of CDRs. The scaffold includes, but not limited to the antibody-derived scaffold that is introduced to stabilize the three-dimensional structure of the antibody, and a fully synthetic scaffold comprising such as biocompatible polymer. See for example, Korndorfer et al., 2003, *Proteins* 53:121-129; Roque et al., 2004, *Biotechnol. Prog.* 20:639-654. In addition, the antibody may be either a mock peptide antibody ("PAMs") or a scaffold containing mock antibodies which uses fibrin connexin similar as scaffolds.

Antibodies may have structures as innate immunoglobulin. "Immunoglobulin" is a tetramer molecule. In natural immunoglobulin, each tetramer consists of two identical polypeptide chain pairs, each pair having a "light" chain (approx. 25 k Da) and a "heavy" chain (approx. 50-70 kDa). The amino terminus of each chain includes a variable domain of about 100 to 110 amino acids, which is mainly related to antigen recognition. The carboxyl terminus of each chain determines the constant region which is mainly associated with the effect of the effectors. The human antibody light chain is classified into K and 2 light chains. The heavy chains were classified into u, 8, a, or ¿, and determined the same type of antigen, such as IgM, IgD, IgG, IgA, and IgE. In light and heavy chains, the variable and constant regions are connected by the "J" region of about 12 or more amino acids, and the heavy chain also includes the "D" region of about over 10 amino acids. Refer to Fundamental Immunology ch. 7 (edited by Paul, 2nd edition, Raven Press, 1989). Variable regions of each light/heavy chain pair form antibody binding sites, in this way a complete immunoglobulin has two binding sites.

The innate immunoglobulin chains exhibit the same basic structure of a relatively conservative skeletal region (FR) connected by three highly variable regions, also known as the complementary decision region or CDRs. From the N end to the C end, the light and heavy chains contain the structural domains FR1, CDR1, FR2, CDR2, FR3, CDR3, and FR4. The distribution of amino acids in all structural domains was consistent with Kabat et al. in Sequences of Proteins of Immunological Interest, 5th edition, U.S. Dept. Of Health and Human Services, PHS, NIH, NIH Publication No. 91-3242, 1991.

Unless otherwise specified, "antibody" means either the intact immunoglobulin or the antigen-binding portion of that can specifically compete binding to intact antibody. Antigen-binding portion can be produced by recombinant DNA techniques, enzymatic or chemical cleavage of intact antibodies. Antigen-binding portion includes, in particular, Fab, Fab', $F(ab)_2$, Fv, structural domain antibodies (dAbs), fragments containing complementarity determining region (CDRs), single-chain antibody (scFv), chimeric antibody, double-chain antibody (diabodies), three-chain antibodies (triabodies), four-chain antibody (tetrabodies) and a polypeptide that contains at least a portion of the immunoglobulin that binds to a polypeptide-specific antigen.

The Fab fragment is a univalent fragment with $V_L$, $V_H$, $C_L$, and $C_{H1}$ domains; The $F(ab')_2$ fragment is a divalent fragment have two Fab fragments connected by a disulfide bond in the hinge region; Fv fragments have $V_H$ and $V_L$ domains; dAb fragments have $V_H$ domain, $V_L$ domain, or antigen binding fragments of $V_H$ or $V_L$ domain (US patent numbers U.S. Pat. Nos. 6,846,634 and 6,696,245; US patent application public numbers US 2005/0202512, US 2004/0202995, US 2004/0038291, US 2004/0009507, and US 2003/0039958; Ward et al., 1989, *Nature* 341:544-546).

Single-chain antibody (scFv) is a fusion protein in which the $V_L$ and $V_H$ regions are joined by a connector (for example, a synthetic sequence of amino acid residues) to form a continuous protein antibody, therein the connector is long enough to allow the protein chain to fold back to itself and to form a univalent antigen binding site (See, for example, Bird et al., 1988, *Science* 242:423-26; and Huston et al., 1988, *Proc. Natl. Acad. Sci. U.S.A.* 85:5879-83).

A double-chain antibody is a divalent antibody contain two polypeptide chains, each of which contains the $V_H$ and $V_L$ regions connected by a joint that is so short that it does not allow pairing of the two domains on the same chain. Therefore, each domain is allowed to pair with a complementary domain on another polypeptide chain (See, for example, Holliger et al., 1993, *Proc. Natl. Acad. Sci. U.S.A.* 90:6444-48; Poljak et al., 1994, *Structure* 2:11 21-23). If the two polypeptide chains of the double-stranded antibody are identical, the double-stranded antibody resulted from their pairing will have the same antigen-binding site. Polypeptide chains with different sequences can be used to prepare double-stranded antibodies with different antigen binding sites. Similarly, three-chain and four-chain antibodies are the antibodies that contain three and four polypeptide chains and form three and four antigen binding sites, which may be the same or different.

This article used the method that Kabat et al. described in Sequences of Proteins of Immunological Interest, 5th edition, U.S. Dept. Of Health and Human Services, PHS, NIH, NIH Publication No. 91-3242, 1991 to identify the complementarity determining region (CDRs) and framework region (FR) of a given antibody. One or more CDRs can be incorporated into a molecule either covalently or noncovalently to make it an antibody. The antibody can incorporate a larger polypeptide chain into the CDR(s). CDR(s) can be covalently attached to another polypeptide chain, or can be non-covalently incorporated into CDR(s). CDRs allows antibodies specifically binding to specific associated antigens.

Antibodies can have one or more binding sites. If there is more than one binding site, the binding site can be the same or different from another. For example, natural human immunoglobulin usually has two identical binding sites, while "bi-specific" or "bifunctional" antibodies have two different binding sites.

The term "murine antibody" includes antibodies having one or more variable and constant regions derived from mouse immunoglobulin sequences.

The term "humanized antibody" is an antibody made by transplanting the sequence of complementary decision regions of mouse antibody molecules into the framework of human antibody variable regions.

The terms "antigen-binding domain," "antigen-binding region," or "antigen-binding site" are the parts of an antibody that contain amino acid residues that interact with an antigen and contribute to its specificity and affinity for the antigen. For antibodies that bind specifically to their antigens, this will include at least part of at least one of its CDR domains.

The term "epitope" is the part of a molecule that binds to (for example, by an antibody) the antibody. An epitope may contain a discontinuous part of a molecule (for example, in a polypeptide, the amino acid residues that are discontinuous in the first order of the polypeptide are close enough to each other in the tertiary and quaternary structures of the polypeptide to be bound by an antibody).

The "same percentage" of two polynucleotides or two polypeptide sequences is determined using the GAP computer program's (GCG Wisconsin Package; a part of version 10.3 (Accelrys, San Diego, CA)) default parameters comparison sequence.

The terms "polynucleotide", "oligonucleotide" and "nucleic acid" can be used alternatively throughout the full text and include DNA molecules (e.g., cDNA or genomic DNA), RNA molecules (e.g., mRNA), DNA or RNA analogues and their hybrids produced using nucleotide analogues (e.g., peptide nucleic acids and non-natural nucleotide analogues). Nucleic acid molecules can be single or double stranded. In one embodiment, the nucleic acid molecules contained in this invention encode the antibody or its fragments, derivatives, mutant proteins, or variants continuous open reading frame.

If their sequences can be reversed and parallel, two single-stranded nucleotides are "complementary" to each other, so that each nucleotide in one polynucleotide is opposite to the complementary nucleotide in the other, no gaps are introduced and no unpaired nucleotides are found at the 5' or 3' ends of each sequence. If two polynucleotides can interbreed under moderately strict conditions, one polynucleotide is "complementary" to the other. Thus, one polynucleotide may be complementary to another polynucleotide, but not its complementary sequence.

The term "carrier" is a nucleic acid that can be used to introduce another nucleic acid connected to it into a cell. One type of carrier is a "plasmid", refer to a linear or circular double-stranded DNA molecule that can be attached to an additional nucleic acid segment. Another type of carrier is a viral vector (e.g., replication-defective retroviruses, adenoviruses, and adenoviral companion viruses) in which additional DNA segments can be introduced into the viral genome. Some carriers can replicate autonomously in the host cells into which they are introduced (For example, bacterial carriers containing the origin of bacterial replication and the free-type mammalian carriers). Other carriers (for example, non-free-type mammalian carriers) are integrated into the host cell genome when introduced into the host cell and thus replicate with the host genome. "Expression carrier" is the type of carrier that can guide the expression of selected polynucleotides.

If the regulatory sequence affects the expression of a nucleotide sequence (for example, expression level, time, or site), then the nucleotide sequence is "operationally linked" to the regulatory sequence. The "regulatory sequence" is the nucleic acid that affects the expression (for example, expression level, time, or site) of the nucleic acid with which it is operationally linked. Regulatory genes, for example, act directly on regulated nucleic acids or through one or more other molecules (e.g., polynucleotides that bind to regulatory sequences and/or nucleic acids). Examples of regulatory sequences include promoters, enhancers, and other expression control elements (e.g., polyadenylation signals). Further examples of regulatory sequences can be described such as Goeddel, 1990, *Gene Expression Technology: Methods in Enzymology*, Volume 185, Academic Press, San Diego, CA; And Baron et al., 1995, *Nucleic Acids Res.* 23:3605-06.

The term "host cell" refers to a cell used to express a nucleic acid such as that provided this article. The host cell may be a prokaryotes, such as *E. coli*, or it can be eukaryotes, such as unicellular eukaryotes (yeast or other fungi, for example), plant cells (such as tobacco or tomato plant cells), animal cells (for example, human cells, monkey cells, hamster cells, rat cells, mouse cells or insect cells) or hybridoma. Usually, the host cell is a culture cell that can be transformed or transfected with a peptide encoding nucleic acid, which can then be expressed in the host cell. The phrase "recombinant host cell" can be used to describe a host cell transformed or transfected with an expected expression of nucleic acid. The host cell may also be a cell that contains the nucleic acid but does not express it at the desired level, unless regulatory sequences are introduced to the host cell so that it is operationally linked to the nucleic acid. It should be understood that the term "host cell" refers to not only the specific subject cell but also to the progeny or possible progeny of that cell. Due to certain modifications occurring in subsequent generations, such as mutations or environmental influences, the progeny may in fact be different from the parent cell but still fall within the scope of the terminology used in this invention.

Intestinal Gastric Inhibitory Peptide Receptor

Intestinal gastric inhibitory peptide receptor belongs to type B of the seven-transmembrane G protein-coupled receptor family. The receptor is coupled to one or more intracellular signaling pathways by a heterotrimeric guanine nucleotide binding protein (G protein) (Drucker et al., 2006, *Cell Metab.* 3:153-65). Up to now, studies show that GIPR is mainly expressed on the surface of pancreatic β cell and adipose cells (Ravn et al., 2013, *J. Biol. Chem.* 288:19760-72), is involved both in the glucose and lipid metabolism in human, and is therefore closely related to diabetes, obesity and related diseases (Skaw et al., 2016, *Diabetes Obes. Metab.* 18:847-854). Both "human GIPR" and "hGIPR" used in this paper refer to human intestinal inhibitory peptide receptor, which can be used interchangeably. The "mouse GIPR" and "mGIPR" used in this paper both refer to the mouse gastric inhibitory peptide receptor, which can also be used interchangeably.

In one embodiment, the antibody presented here is an antibody specifically binding to human GIPR. In another embodiment, the antibody presented here is an antibody specifically binding to GIPR on the cell membrane, and the antibody can inhibit or block the transduction of GIP signals in these cells. In another embodiment, the antibody presented here is an antibody specifically binding to human GIPR and the antibody can bind to GIPR of other species (e.g., monkeys or mice) and block GIP signaling in these species. In a further embodiment, the antibody presented here is a murine antibody binding to human GIPR and the antibody can bind to GIPR of other species (e.g., monkey).

In one embodiment, the amino acid and polynucleotide sequences of GIPR are listed below, with sequence data from the Gene-Bank database of the US national center for biotechnology information and the Uniprot database of the European institute for biological information:

Human (*Homo sapiens*) polynucleotide (SEQ ID NO:114); accession number: S79852; Human (*Homo sapiens*) amino acid (SEQ ID NO:113); accession number: AAB35419.2;

Monkey (*Rhesus macaque*) polynucleotide (SEQ ID NO:116); accession number: XM 015124289.1;

Monkey (*Rhesus macaque*) amino acid (SEQ ID NO:115); accession number: XP 014979775;

Mouse (*Mus musculus*) polynucleotide (SEQ ID NO:118); accession number: CCDS39795; and mouse (*Mus musculus*) amino acid (SEQ ID NO:117); accession number: Q0P543.

Intestinal Gastric Inhibitory Peptide Receptor (GIPR) Antibody

In one embodiment, provided herein is the GIPR antibody. In another embodiment, the GIPR antibody provided herein is the complete GIPR antibody. In another embodiment, the GIPR antibody provided herein is the GIPR antibody fragment. In another embodiment, the GIPR antibody provided herein is a derivative of GIPR antibody. In another embodiment, the GIPR antibody provided herein is the GIPR antibody mutant protein. In a further embodiment, the GIPR antibody provided herein is the variant of GIPR antibody.

In one embodiment, the GIPR antibody provided herein comprises one, two, three, four, five, or six amino acid sequences, each of which is independently selected from the amino acid sequences listed below:

a. Light chain CDR1 amino acid sequence: SEQ ID NO: 1, SEQ ID NO: 4, SEQ ID NO: 7, SEQ ID NO: 10, SEQ ID NO: 13, and SEQ ID NO: 15;
b. Light chain CDR2 amino acid sequence: SEQ ID NO: 2, SEQ ID NO: 5, SEQ ID NO: 8, SEQ ID NO: 11, and SEQ ID NO: 16;
c. Light chain CDR3 amino acid sequence: SEQ ID NO: 3, SEQ ID NO: 6, SEQ ID NO: 9, SEQ ID NO: 12, SEQ ID NO: 14, and SEQ ID NO: 17;
d. Heavy chain CDR1 amino acid sequence: SEQ ID NO: 18, SEQ ID NO: 23, and SEQ ID NO: 26;
e. Heavy chain CDR2 amino acid sequence: SEQ ID NO: 19, SEQ ID NO: 21, SEQ ID NO: 24, SEQ ID NO: 27, and SEQ ID NO: 29; and
f. Heavy chain CDR3 amino acid sequence: SEQ ID NO: 20, SEQ ID NO: 22, SEQ ID NO: 25, SEQ ID NO: 28, and SEQ ID NO: 30.

Table 1 lists the amino acid sequences of the light chain CDRs of the GIPR antibody provided herein, as well as the corresponding polynucleotide coding sequences. Table 2 lists the amino acid sequences of the heavy chain CDRs of the GIPR antibody provided herein, as well as the corresponding polynucleotide coding sequences.

TABLE 1 light chain CDR amino acid sequences and polynucleotide coding sequences

| | CDR1 | CDR2 | CDR3 |
|---|---|---|---|
| A-1 nucleotide | aaggccagtcaggatgtgggtactgct gtagcc (SEQ ID NO: 31) | tgggcatacatccggcacact (SEQ ID NO: 32) | cagcaatatagcagctatccgtg gacg (SEQ ID NO: 33) |
| A-1 Amino acid | KASQDVGTAVA (SEQ ID NO: 1) | WAYIRHT (SEQ ID NO: 2) | QQYSSYPWT (SEQ ID NO: 3) |
| A-2 nucleotide | agacccagtgaaagtgttgatagttatg gcaatagttttatgcac (SEQ ID NO: 34) | cttgcatccaacctagaatct (SEQ ID NO: 35) | cagcaaaataatgaggatcctc ggacg (SEQ ID NO: 36) |
| A-2 Amino acid | RPSESVDSYGNSFMH (SEQ ID NO: 4) | LASNLES (SEQ ID NO: 5) | QQNNEDPRT (SEQ ID NO: 6) |
| A-3 nucleotide | aaggcaagtgaggacatatataatcg gttcgcc (SEQ ID NO: 37) | gatgcaaccagtttggaaact (SEQ ID NO: 38) | caacagtattggagtattccgtg gacg (SEQ ID NO: 39) |
| A-3 Amino acid | KASEDIYNRFA (SEQ ID NO: 7) | DATSLET (SEQ ID NO: 8) | QQYWSIPWT (SEQ ID NO: 9) |
| A-4 nucleotide | agggccagccaaagtgtcaatacatct gtctatagttatatacac (SEQ ID NO: 40) | tatgcatccaacctagaatct (SEQ ID NO: 41) | caacacagttgggattttccttac acg (SEQ ID NO: 42) |
| A-4 Amino acid | RASQSVNTSVYSYIH (SEQ ID NO: 10) | YASNLES (SEQ ID NO: 11) | QHSWDFPYT (SEQ ID NO: 12) |
| A-5 nucleotide | agagccagccagtccgtgaacacag ccgtgtactcttatatccac (SEQ ID NO: 43) | tatgcatccaacctagaatct (SEQ ID NO: 41) | cagcacagcttcgatttcccctac acc (SEQ ID NO: 44) |
| A-5 Amino acid | RASQSVNTAVYSYIH (SEQ ID NO: 13) | YASNLES (SEQ ID NO: 11) | QHSFDFPYT (SEQ ID NO: 14) |
| A-6 nucleotide | aaggcgagtcaggacattaatagctat ttaagc (SEQ ID NO: 45) | gcaaacagattggtagat (SEQ ID NO: 46) | ctacagtatgatgagtttccattc acg (SEQ ID NO: 47) |
| A-6 Amino acid | KASQDINSYLS (SEQ ID NO: 15) | ANRLVD (SEQ ID NO: 16) | LQYDEFPFT (SEQ ID NO: 17) |

TABLE 2 heavy chain CDR amino acid sequences and polynucleotide coding sequences

| | CDR1 | CDR2 | CDR3 |
|---|---|---|---|
| A-1 nucleotide | ggattcactttcagtagctat gccatgtct (SEQ ID NO: 48) | tccattagtagtggtggtgccacctact atccagacagtgtgaag (SEQ ID NO: 49) | ggcgagggcggtagtagctaccc ggcctggtttgctttc (SEQ ID NO: 50) |
| A-1 Amino acid | GFTFSSYAMS (SEQ ID NO: 18) | SISSGGATYYPDSVKG (SEQ ID NO: 19) | GEGGSSYPAWFAF (SEQ ID NO: 20) |
| A-2 nucleotide | ggattcactttcagtagctat gccatgtct (SEQ ID NO: 48) | gaaattagtagtggtggtagttacacct actatccagacactgtgacgggc (SEQ ID NO: 51) | gataaggcgactcgaactggcat gggatttttttaccatactatggact ac (SEQ ID NO: 52) |
| A-2 Amino acid | GFTFSSYAMS (SEQ ID NO: 18) | EISSGGSYTYYPDTVTG (SEQ ID NO: 21) | DKATRTGMGFFYHTM DY (SEQ ID NO: 22) |
| A-3 nucleotide | ggctacacattcagtaggt actggatagag (SEQ ID NO: 53) | gagattttacctggaagtgatagtccta actacaatgagaagttcaagggc (SEQ ID NO: 54) | acggtagtagctacaaggtttgctt ac (SEQ ID NO: 55) |
| A-3 Amino acid | GYTFSRYWIE (SEQ ID NO: 23) | EILPGSDSPNYNEKFK (SEQ ID NO: 24) | TVVATRFAY (SEQ ID NO: 25) |
| A-4 nucleotide | ggctactcaatcaccagtg attatgcctggaac (SEQ ID NO: 56) | tacataagctacagaggcatcgctacc tataaaccatctctcaaaagt (SEQ ID NO: 57) | ggggaatacggccccggcaactt tgacttc (SEQ ID NO: 58) |
| A-4 Amino acid | GYSITSDYAWN (SEQ ID NO: 26) | YISYRGIATYKPSLKS (SEQ ID NO: 27) | GEYGPGNFDF (SEQ ID NO: 28) |
| A-5 nucleotide | ggctactcaatcaccagtg attatgcctggaac (SEQ ID NO: 56) | tacataagctacagaggcatcgctacc tataaaccatctctcaaaagt (SEQ ID NO: 57) | ggggaatacggccccggcaactt tgacttc (SEQ ID NO: 58) |
| A-5 Amino acid | GYSITSDYAWN (SEQ ID NO: 26) | YISYRGIATYKPSLKS (SEQ ID NO: 27) | GEYGPGNFDF (SEQ ID NO: 28) |
| A-6 nucleotide | ggctactcaatcaccagtg attatgcctggaac (SEQ ID NO: 56) | tacatgagctaccgtggtaccgcaacg tacaatccatttctcaaaagt (SEQ ID NO: 59) | tatgattacgacgttccccggtttcc ttac (SEQ ID NO: 60) |
| A-6 Amino acid | GYSITSDYAWN (SEQ ID NO: 26) | YMSYRGTATYNPFLKS (SEQ ID NO: 29) | YDYDVPRFPY (SEQ ID NO: 30) |

In one embodiment, the antibody provided herein comprises a sequence different from one of the CDR amino acid sequences listed in Tables 1 and 2 by five, four, three, two or one single amino acid addition, replacement, and/or deletion. In another embodiment, the antibody provided herein contains a sequence different from one of the CDR amino acid sequences listed in Tables 1 and 2 by four, three, two or one single amino acid addition, replacement, and/or deletion.

In another embodiment, the antibody provided herein contains a sequence different from one of the CDR amino acid sequences listed in Tables 1 and 2 by three, two or one single amino acid addition, replacement, and/or deletion.

In another embodiment, the antibody provided herein contains a sequence different from one of the CDR amino acid sequences listed in Tables 1 and 2 by two or one single amino acid addition, replacement, and/or deletion.

In further embodiments, the antibody provided herein contains a sequence that differs from one of the CDR amino acid sequences listed in Tables 1 and 2 by a single amino acid addition, replacement, and/or deletion.

In one embodiment, the GIPR antibody provided herein comprises one or two amino acid sequences, wherein each amino acid sequence is independently selected from the amino acid sequences listed below:

a. Light chain CDR1 amino acid sequences: SEQ ID NO: 1, SEQ ID NO: 4, SEQ ID NO: 7, SEQ ID NO: 10, SEQ ID NO: 13, and SEQ ID NO: 15; and
b. Heavy chain CDR1 amino acid sequences: SEQ ID NO: 18, SEQ ID NO: 23, and SEQ ID NO: 26.

In another embodiment, the GIPR antibody provided herein comprises one or two amino acid sequences, wherein each amino acid sequence is independently selected from the amino acid sequences listed below:

a. Light chain CDR2 amino acid sequences: SEQ ID NO: 2, SEQ ID NO: 5, SEQ ID NO: 8, SEQ ID NO: 11, and SEQ ID NO: 16; and
b. Heavy chain CDR2 amino acid sequences: SEQ ID NO: 19, SEQ ID NO: 21, SEQ ID NO: 24, SEQ ID NO: 27, and SEQ ID NO: 29.

In another embodiment, the GIPR antibody provided herein comprises one, two, three, or four amino acid sequences, wherein each amino acid sequence is independently selected from the amino acid sequences listed below:

a. Light chain CDR3 amino acid sequences: SEQ ID NO: 3, SEQ ID NO: 6, SEQ ID NO: 9, SEQ ID NO: 12, SEQ ID NO: 14, and SEQ ID NO: 17; and
b. Heavy chain CDR3 amino acid sequences: SEQ ID NO: 20, SEQ ID NO: 22, SEQ ID NO: 25, SEQ ID NO: 28, and SEQ ID NO: 30.

In another embodiment, the GIPR antibody provided herein comprises one, two, three, or four amino acid sequences, wherein each amino acid sequence is independently selected from the amino acid sequences listed below:

a. Light chain CDR1 amino acid sequences: SEQ ID NO: 1, SEQ ID NO: 4, SEQ ID NO: 7, SEQ ID NO: 10, SEQ ID NO: 13, and SEQ ID NO: 15;

b. Heavy chain CDR1 amino acid sequences: SEQ ID NO: 18, SEQ ID NO: 23, and SEQ ID NO: 26;

c. Light chain CDR2 amino acid sequences: SEQ ID NO: 2, SEQ ID NO: 5, SEQ ID NO: 8, SEQ ID NO: 11, and SEQ ID NO: 16; and d. Heavy chain CDR2 amino acid sequences: SEQ ID NO: 19, SEQ ID NO: 21, SEQ ID NO: 24, SEQ ID NO: 27, and SEQ ID NO: 29.

In another embodiment, the GIPR antibody provided herein comprises one, two, three, or four amino acid sequences, wherein each amino acid sequence is independently selected from the amino acid sequences listed below:

a. Light chain CDR1 amino acid sequences: SEQ ID NO: 1, SEQ ID NO: 4, SEQ ID NO: 7, SEQ ID NO: 10, SEQ ID NO: 13, and SEQ ID NO: 15;

b. Heavy chain CDR1 amino acid sequences: SEQ ID NO: 18, SEQ ID NO: 23, and

SEQ ID NO: 26;

c. Light chain CDR3 amino acid sequences: SEQ ID NO: 3, SEQ ID NO: 6, SEQ ID NO: 9, SEQ ID NO: 12, SEQ ID NO: 14, and SEQ ID NO: 17; and d. Heavy chain CDR3 amino acid sequences: SEQ ID NO: 20, SEQ ID NO: 22, SEQ ID NO: 25, SEQ ID NO: 28, and SEQ ID NO: 30.

In further embodiments, the GIPR antibody provided herein comprises one, two, three, or four amino acid sequences, wherein each amino acid sequence is independently selected from the amino acid sequences listed below:

a. Light chain CDR2 amino acid sequences: SEQ ID NO: 2, SEQ ID NO: 5, SEQ ID NO: 8, SEQ ID NO: 11, and SEQ ID NO: 16;

b. Heavy chain CDR2 amino acid sequences: SEQ ID NO: 19, SEQ ID NO: 21, SEQ ID NO: 24, SEQ ID NO: 27, and SEQ ID NO: 29;

c. Light chain CDR3 amino acid sequences: SEQ ID NO: 3, SEQ ID NO: 6, SEQ ID NO: 9, SEQ ID NO: 12, SEQ ID NO: 14, and SEQ ID NO: 17; and d. Heavy chain CDR3 amino acid sequences: SEQ ID NO: 20, SEQ ID NO: 22, SEQ ID NO: 25, SEQ ID NO: 28, and SEQ ID NO: 30.

In one embodiment, the GIPR antibody provided herein comprises one, two, or three amino acid sequences, wherein each amino acid sequence is independently selected from the amino acid sequences listed below: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

In another embodiment, the GIPR antibody provided herein comprises one, two, or three amino acid sequences, wherein each amino acid sequence is independently selected from the amino acid sequences listed below: SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In one embodiment, the GIPR antibody provided herein comprises a combination of light chain and heavy chain CDR1 amino acid sequences independently selected from the list below: SEQ ID NO: 1 and SEQ ID NO: 18, SEQ ID NO: 4 and SEQ ID NO: 18, SEQ ID NO: 7 and SEQ ID NO: 23, SEQ ID NO: 10 and SEQ ID NO: 26, SEQ ID NO: 13 and SEQ ID NO: 26, and SEQ ID NO: 15 and SEQ ID NO: 26.

In another embodiment, the GIPR antibody provided herein comprises a combination of light chain and heavy chain CDR2 amino acid sequences independently selected from the list below: SEQ ID NO: 2 and SEQ ID NO: 19, SEQ ID NO: 5 and SEQ ID NO: 21, SEQ ID NO: 8 and SEQ ID NO: 24, SEQ ID NO: 11 and SEQ ID NO: 27, and SEQ ID NO: 16 and SEQ ID NO: 29.

In further embodiments, the GIPR antibody provided herein comprises a combination of light chain and heavy chain CDR3 amino acid sequences independently selected from the list below: SEQ ID NO: 3 and SEQ ID NO:20, SEQ ID NO: 6 and SEQ ID NO: 22, SEQ ID NO: 9 and SEQ ID NO: 25, SEQ ID NO: 12 and SEQ ID NO: 28, SEQ ID NO: 14 and SEQ ID NO: 28, and SEQ ID NO: 17 and SEQ ID NO: 30.

In one embodiment, the GIPR antibody provided herein comprises:

a. A combination of light and heavy chain CDR1 amino acid sequences independently selected from the list below: SEQ ID NO: 1 and SEQ ID NO: 18, SEQ ID NO: 4 and SEQ ID NO: 18, SEQ ID NO: 7 and SEQ ID NO: 23, SEQ ID NO: 10 and SEQ ID NO: 26, SEQ ID NO: 13 and SEQ ID NO: 26, and SEQ ID NO: 15 and SEQ ID NO: 26; and b. A combination of light and heavy chain CDR2 amino acid sequences independently selected from the list below: SEQ ID NO: 2 and SEQ ID NO: 19, SEQ ID NO: 5 and SEQ ID NO: 21, SEQ ID NO: 8 and SEQ ID NO: 24, SEQ ID NO: 11 and SEQ ID NO: 27, and SEQ ID NO: 16 and SEQ ID NO: 29.

In another embodiment, the GIPR antibody provided herein comprises:

a. A combination of light and heavy chain CDR1 amino acid sequences independently selected from the list below: SEQ ID NO: 1 and SEQ ID NO: 18, SEQ ID NO: 4 and SEQ ID NO: 18, SEQ ID NO: 7 and SEQ ID NO: 23, SEQ ID NO: 10 and SEQ ID NO: 26, SEQ ID NO: 13 and SEQ ID NO: 26, and SEQ ID NO: 15 and SEQ ID NO: 26; and b. A combination of light and heavy chain CDR3 amino acid sequences independently selected from the list below: SEQ ID NO: 3 and SEQ ID NO:20, SEQ ID NO: 6 and SEQ ID NO: 22, SEQ ID NO: 9 and SEQ ID NO: 25, SEQ ID NO: 12 and SEQ ID NO: 28, SEQ ID NO: 14 and SEQ ID NO: 28, and SEQ ID NO: 17 and SEQ ID NO: 30.

In another embodiment, the GIPR antibody provided herein contains:

a. A combination of light and heavy chain CDR2 amino acid sequences independently selected from the list below: SEQ ID NO: 2 and SEQ ID NO: 19, SEQ ID NO: 5 and SEQ ID NO: 21, SEQ ID NO: 8 and SEQ ID NO: 24, SEQ ID NO: 11 and SEQ ID NO: 27, and SEQ ID NO: 16 and SEQ ID NO: 29; and b. A combination of light and heavy chain CDR3 amino acid sequences independently selected from the list below: SEQ ID NO: 3 and SEQ ID NO:20, SEQ ID NO: 6 and SEQ ID NO: 22, SEQ ID NO: 9 and SEQ ID NO: 25, SEQ ID NO: 12 and SEQ ID NO: 28, SEQ ID NO: 14 and SEQ ID NO: 28, and SEQ ID NO: 17 and SEQ ID NO: 30.

In a further embodiment, the GIPR antibody provided herein comprises:

a. A combination of light and heavy chain CDR1 amino acid sequences independently selected from the list below: SEQ ID NO: 1 and SEQ ID NO: 18, SEQ ID NO: 4 and SEQ ID NO: 18, SEQ ID NO: 7 and SEQ ID NO: 23, SEQ ID NO: 10 and SEQ ID NO: 26, SEQ ID NO: 13 and SEQ ID NO: 26, and SEQ ID NO: 15 and SEQ ID NO: 26;

b. A combination of light and heavy chain CDR2 amino acid sequences independently selected from the list below: SEQ ID NO: 2 and SEQ ID NO: 19, SEQ ID NO: 5 and SEQ ID NO: 21, SEQ ID NO: 8 and SEQ ID NO: 24, SEQ ID NO: 11 and SEQ ID NO: 27, and SEQ ID NO: 16 and SEQ ID NO: 29; and c. A combination of light and heavy chain CDR3 amino acid sequences independently selected from the list below: SEQ ID NO: 3 and SEQ ID NO:20, SEQ ID NO: 6 and SEQ ID NO: 22, SEQ ID NO: 9 and SEQ ID NO: 25, SEQ ID NO: 12 and SEQ ID NO: 28, SEQ ID NO: 14 and SEQ ID NO: 28, and SEQ ID NO: 17 and SEQ ID NO: 30.

In one embodiment, the GIPR antibody provided herein comprises:

a. Combination of light chain and heavy chain CDR1, CDR2, and CDR3 amino acid sequences: SEQ ID NO: 1, SEQ ID NO: 2, SEQ ID NO: 3, SEQ ID NO: 18, SEQ ID NO: 19, and SEQ ID NO: 20;

b. Combination of light chain and heavy chain CDR1, CDR2, and CDR3 amino acid sequences: SEQ ID NO: 4, SEQ ID NO: 5, SEQ ID NO: 6, SEQ ID NO: 18, SEQ ID NO: 21, and SEQ ID NO: 22;

c. Combination of light chain and heavy chain CDR1, CDR2, and CDR3 amino acid sequences: SEQ ID NO: 7, SEQ ID NO: 8, SEQ ID NO: 9, SEQ ID NO: 23, SEQ ID NO: 24, and SEQ ID NO: 25;

d. Combination of light chain and heavy chain CDR1, CDR2, and CDR3 amino acid sequences: SEQ ID NO: 10, SEQ ID NO: 11, SEQ ID NO: 12, SEQ ID NO: 26, SEQ ID NO: 27, and SEQ ID NO: 28;

e. Combination of light chain and heavy chain CDR1, CDR2, and CDR3 amino acid sequences: SEQ ID NO: 13, SEQ ID NO: 11, SEQ ID NO: 14, SEQ ID NO: 26, SEQ ID NO: 27, and SEQ ID NO: 28; or f. Combination of light chain and heavy chain CDR1, CDR2, and CDR3 amino acid sequences: SEQ ID NO: 15, SEQ ID NO: 16, SEQ ID NO: 17, SEQ ID NO: 26, SEQ ID NO: 29, and SEQ ID NO: 30.

In one embodiment, the GIPR antibody provided herein comprises one or two amino acid sequences, wherein each amino acid sequence is independently selected from the amino acid sequence listed below:

a. Light chain variable domain amino acid sequences: SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO:69, SEQ ID NO: 70, and SEQ ID NO: 71; and an amino acid sequence that is at least 80%, at least 85%, at least 90%, or at least 95% identical to any above sequence; and b. Heavy chain variable domain amino acid sequences: SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, and SEQ ID NO: 80; and an amino acid sequence that is at least 80%, at least 85%, at least 90%, or at least 95% identical to any above sequence.

In another embodiment, the polynucleotide coding sequence for the GIPR antibody provided herein comprises one or two polynucleotide coding sequences, wherein each polynucleotide coding sequence is independently selected from the polynucleotide sequences listed below:

a. Light chain variable domain polynucleotide coding sequences: SEQ ID NO: 81, SEQ ID NO: 82, SEQ ID NO: 83, SEQ ID NO: 84, SEQ ID NO: 85, SEQ ID NO: 86, SEQ ID NO:87, SEQ ID NO: 88, SEQ ID NO: 89, SEQ ID NO: 90, and SEQ ID NO: 91; and a polynucleotide sequence that is at least 80%, at least 85%, at least 90%, or at least 95% identical to any above sequence; and b. Heavy chain variable domain polynucleotide coding sequences: SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, and SEQ ID NO: 100; and a polynucleotide sequence that is at least 80%, at least 85%, at least 90%, or at least 95% identical to any above sequence.

In one embodiment, the GIPR antibody provided herein comprises an amino acid sequence independently selected from the list below: SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO:69, SEQ ID NO: 70, and SEQ ID NO: 71.

In another embodiment, the GIPR antibody provided herein comprises an amino acid sequence independently selected from the list below: SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, and SEQ ID NO: 80.

In one embodiment, the GIPR antibody provided herein comprises a combination of amino acid sequences independently selected from the light chain and heavy chain variable domain amino acid sequences listed below: SEQ ID NO: 61 and SEQ ID NO: 72, SEQ ID NO: 62 and SEQ ID NO: 73, SEQ ID NO: 63 and SEQ ID NO: 74, SEQ ID NO: 64 and SEQ ID NO: 74, SEQ ID NO: 65 and SEQ ID NO: 75, SEQ ID NO: 66 and SEQ ID NO: 76, SEQ ID NO: 67 and SEQ ID NO: 77, SEQ ID NO: 68 and SEQ ID NO: 77, SEQ ID NO: 69 and SEQ ID NO: 78, SEQ ID NO: 70 and SEQ ID NO: 79, and SEQ ID NO: 71 and SEQ ID NO: 80.

In one embodiment, the GIPR antibody provided herein comprises an amino acid sequence independently selected from the list below: SEQ ID NO: 62, SEQ ID NO: 63, SEQ ID NO: 64, SEQ ID NO: 66, SEQ ID NO: 67, SEQ ID NO: 68, SEQ ID NO: 73, SEQ ID NO: 74, SEQ ID NO: 76, and SEQ ID NO: 77.

In another embodiment, the GIPR antibody provided herein comprises a combination of amino acid sequences independently selected from the light chain and heavy chain variable domain amino acid sequences listed below: SEQ ID NO: 61 and SEQ ID NO: 72 (L1H1), SEQ ID NO: 62 and SEQ ID NO: 73 (L2H2), SEQ ID NO: 63 and SEQ ID NO: 74 (L3H3), SEQ ID NO: 64 and SEQ ID NO: 74 (L4H3), SEQ ID NO: 65 and SEQ ID NO: 75 (L5H4), SEQ ID NO: 66 and SEQ ID NO: 76 (L6H5), SEQ ID NO: 67 and SEQ ID NO: 77 (L7H6), SEQ ID NO: 68 and SEQ ID NO: 77 (L8H6), SEQ ID NO: 69 and SEQ ID NO: 78 (L9H7), SEQ ID NO: 70 and SEQ ID NO: 79 (L10H8), and SEQ ID NO: 71 and SEQ ID NO: 80 (L11H9).

The symbol "LxHy" can also be used herein to refer to the GIPR antibody provided herein, wherein "x" corresponds to the light chain variable region sequence code and "y" corresponds to the heavy chain variable region sequence code. For example, L2H2 is a complete antibody with a light chain variable region comprising the SEQ ID NO: 62 (L2) amino acid sequence and a heavy chain variable region comprising the SEQ ID NO: 73 (H2) amino acid sequence.

In one embodiment, the GIPR antibody provided herein comprises one or two amino acid sequences, wherein each amino acid sequence is independently selected from the amino acid sequence listed below:

a. Light chain constant region amino acid sequences: SEQ ID NO: 101 and SEQ ID NO: 102; and b. Heavy chain constant region amino acid sequences: SEQ ID NO: 103 and SEQ ID NO: 104, and SEQ ID NO: 124.

In one embodiment, the GIPR antibody provided herein comprises one or two amino acid sequences, wherein each amino acid sequence is independently selected from a combination of light chain and heavy chain constant region amino acid sequences listed below: SEQ ID NO: 101 and SEQ ID NO: 103, SEQ ID NO: 101 and SEQ ID NO: 104, SEQ ID NO: 102 and SEQ ID NO: 103, and SEQ ID NO: 102 and SEQ ID NO: 104. In another embodiment, the GIPR antibody provided herein comprises one or two amino acid sequences, wherein each amino acid sequence is independently selected from a combination of light chain and heavy chain constant region amino acid sequences listed below: SEQ ID NO: 101 and SEQ ID NO: 124, and SEQ ID NO: 102 and SEQ ID NO: 124.

In one embodiment, the GIPR antibodies provided herein comprise the light and heavy chain CDRs listed herein, and the amino acid sequences of the FRs (framework). The amino acid sequences of FRs are contained in the light chain or the heavy chain variable domain sequence and are not separately displayed. In one embodiment, the antibody comprises a light chain CDR1 sequence listed herein. In another embodiment, the antibody comprises a light chain CDR2 sequence listed herein. In another embodiment, the antibody comprises a light chain CDR3 sequence listed herein. In another embodiment, the antibody comprises a heavy chain CDR1 sequence listed herein. In another embodiment, the antibody comprises a heavy chain CDR2 sequence listed herein. In another embodiment, the antibody comprises a heavy chain CDR3 sequence listed herein. In another embodiment, the antibody comprises a light chain FR1 sequence herein. In another embodiment, the antibody comprises a light chain FR2 sequence herein. In another embodiment, the antibody comprises a light chain FR3 sequence herein. In another embodiment, the antibody comprises a light chain FR4 sequence herein. In another embodiment, the antibody comprises a heavy chain FR1 sequence herein. In another embodiment, the antibody comprises a heavy chain FR2 sequence herein. In another embodiment, the antibody comprises a heavy chain FR3 sequence herein. In a further embodiment, the antibody comprises a heavy chain FR4 sequence herein.

In one embodiment, a light chain CDR3 sequence of the antibody differs from SEQ ID NO: 6, SEQ ID NO: 12, and SEQ ID NO: 14 of the light chain CDR3 sequences illustrated above by no more than six, five, four, three, two or one amino acid addition(s), substitution(s), and/or deletion(s). In another embodiment, a heavy chain CDR3 sequence of the antibody differs from SEQ ID NO: 22 and SEQ ID NO: 28 of the heavy chain CDR3 sequences illustrated above by no more than six, five, four, three, two or one amino acid addition(s), substitution(s), and/or deletion(s). In a further embodiment, a light chain CDR3 sequence of the antibody differs from SEQ ID NO: 6, SEQ ID NO: 12, and SEQ ID NO: 14 of the light chain CDR3 sequences illustrated above by no more than six, five, four, three, two or one amino acid addition(s), substitution(s), and/or deletion(s), and a heavy chain CDR3 sequence of the antibody differs from SEQ ID NO: 22 and SEQ ID NO: 28 of the heavy chain CDR3 sequences illustrated above by no more than six, five, four, three, two or one amino acid addition(s), substitution(s), and/or deletion(s). In another embodiment, the antibody further comprises a combination of one, two, three, four, five or six of light and heavy chain CDR sequences illustrated above.

In one embodiment, the GIPR antibody provided herein comprises a light chain variable domain amino acid sequence selected from L2 (SEQ ID NO:62), L3 (SEQ ID NO: 63), L4 (SEQ ID NO:64), L6 (SEQ ID NO:66), L7 (SEQ ID NO:67), and L8 (SEQ ID NO: 68) light chain variable domain sequences listed herein. In one embodiment, the amino acid sequence of the light chain variable domain of the GIPR antibody differs from the amino acid sequence of one light chain variable domain of L2 (SEQ ID NO:62), L3 (SEQ ID NO:63), L4 (SEQ ID NO:64), L6 (SEQ ID NO:66), L7 (SEQ ID NO:67), and L8 (SEQ ID NO:68) by fifteen, fourteen, thirteen, twelve, eleven, ten, nine, eight, seven, six, five, four, three, two or one amino acid difference, wherein the difference in each sequence is independently a deletion, insertion or substitution of an amino acid residue. In another embodiment, the light chain variable domain of the GIPR antibody comprises an amino acid sequence at least 70%, at least 75%, at least 80%, at least 85%, at least 90%, at least 95%, at least 97%, or at least 99% identical to the amino acid sequence of one light chain variable domain of L2 (SEQ ID NO:62), L3 (SEQ ID NO: 63), L4 (SEQ ID NO:64), L6 (SEQ ID NO:66), L7 (SEQ ID NO:67), and L8 (SEQ ID NO: 68). In another embodiment, the polynucleotide coding sequence of the light chain variable domain of the GIPR antibody comprises a nucleotide coding sequence at least 70%, at least 75%, at least 80%, at least 85%, at least 90%, at least 95%, at least 97%, or at least 99% identical to one polynucleotide coding sequence of L2 (SEQ ID NO: 62), L3 (SEQ ID NO:63), L4 (SEQ ID NO:64), L6 (SEQ ID NO:66), L7 (SEQ ID NO: 67), and L8 (SEQ ID NO:68). In another embodiment, the polynucleotide coding sequence of the light chain variable domain of the GIPR antibody comprises polynucleotide sequences hybridized under moderate conditions with one complementary polynucleotide coding sequences of L2 (SEQ ID NO:62), L3 (SEQ ID NO: 63), L4 (SEQ ID NO:64), L6 (SEQ ID NO:66), L7 (SEQ ID NO:67), and L8 (SEQ ID NO: 68). In a further embodiment, the polynucleotide coding sequence of the light chain variable domain of the GIPR antibody comprises a polynucleotide sequence hybridized under stringent conditions with a complementary polynucleotide coding sequence of one light chain variable domain of L2 (SEQ ID NO:62), L3 (SEQ ID NO: 63), L4 (SEQ ID NO:64), L6 (SEQ ID NO:66), L7 (SEQ ID NO:67), and L8 (SEQ ID NO: 68).

In one embodiment, the GIPR antibody provided herein comprises a heavy chain variable domain amino acid sequence selected from H2 (SEQ ID NO:73), H3 (SEQ ID NO: 74), H5 (SEQ ID NO:76), and H6 (SEQ ID NO:77) heavy chain variable domain sequences listed herein. In another embodiment, the heavy chain variable domain amino acid sequence of the GIPR antibody differs from one heavy chain variable domain sequence of H2 (SEQ ID NO:73), H3 (SEQ ID NO:74), H5 (SEQ ID NO:76), and H6 (SEQ ID NO:77) by fifteen, fourteen, thirteen, twelve, eleven, ten, nine, eight, seven, six, five, four, three, two or one amino acid, wherein the difference in each sequence is independently a deletion, insertion or substitution of one amino acid residue. In another embodiment, the heavy chain variable domain of the GIPR antibody comprises an amino acid sequence at least 70%, at least 75%, at least 80%, at least 85%, at least 90%, at least 95%, at least 97%, or at least 99% identical to one heavy chain variable domain sequence of H2 (SEQ ID NO:73), H3 (SEQ ID NO:74), H5 (SEQ ID NO:76), and H6 (SEQ ID NO:77). In another embodiment, the heavy chain variable domain of the GIPR antibody comprises a polynucleotide coding sequence at least 70%, at least 75%, at least 80%, at least 85%, at least 90%, at least 95%, at least 97%, or at least 99% identical to one heavy chain variable domain polynucleotide coding sequence of H2 (SEQ ID NO: 73), H3 (SEQ ID NO:74), H5 (SEQ ID NO:76), and H6 (SEQ ID NO:77). In another embodiment, the polynucleotide coding sequence of the GIPR antibody heavy chain variable domain comprises a polynucleotide sequence hybridized to a complementary polynucleotide coding sequence of one heavy chain variable domains of H2 (SEQ ID NO:73), H3 (SEQ ID NO:74), H5 (SEQ ID NO:76), and H6 (SEQ ID NO: 77) under moderately strict conditions. In one embodiment, the polynucleotide coding sequence of the GIPR antibody heavy chain variable domain comprises a polynucleotide sequence hybridized under stringent conditions with a complementary polynucleotide coding sequence of one heavy chain variable domains of H2 (SEQ ID NO: 73), H3 (SEQ ID NO:74), H5 (SEQ ID NO:76), and H6 (SEQ ID NO:77).

In an embodiment, the antibody provided herein is an antibody comprising a combination of L1H1 (SEQ ID NO:61 and SEQ ID NO:72), L2H2 (SEQ ID NO:62 and SEQ ID NO:73), L3H3 (SEQ ID NO:63 and SEQ ID NO:74), L4H3 (SEQ ID NO:64 and SEQ ID NO:74), L5H4 (SEQ ID NO:65 and SEQ ID NO:75), L6H5 (SEQ ID NO: 66 and SEQ ID NO:76), L7H6 (SEQ ID NO:67 and SEQ ID NO:77), L8H6 (SEQ ID NO: 68 and SEQ ID NO:77), L9H7 (SEQ ID NO:69 and SEQ ID NO:78), L10H8 (SEQ ID NO:70 and SEQ ID NO:79), or L11H9 (SEQ ID NO:71 and SEQ ID NO:80), or of a desired phenotype (for example, IgA, IgG1, IgG2a, IgG2b, IgG3, IgM, IgE, or IgD), or a Fab or F(ab') 2 fragment thereof.

In an embodiment, the antibody provided herein is an antibody comprising a combination of L2H2 (SEQ ID NO:62 and SEQ ID NO:73), L3H3 (SEQ ID NO:63 and SEQ ID NO:74), L4H3 (SEQ ID NO:64 and SEQ ID NO:74), L6H5 (SEQ ID NO:66 and SEQ ID NO:76), L7H6 (SEQ ID NO:67 and SEQ ID NO:77), or L8H6 (SEQ ID NO: 68 and SEQ ID NO:77), or of a desired phenotype (for example, IgA, IgG1, IgG2a, IgG2b, IgG3, IgM, IgE, or IgD), or a Fab or F(ab') 2 fragment thereof.

The antibodies provided herein can comprise any of the known constant regions of the field. The light chain constant region can be, for example, k or A light chain constant region, such as a mouse k or 2 light chain constant region. The heavy chain constant region can be, for example, an a, 8, ¿, y, or u heavy chain constant region, such as the mouse a, 8, &, Y, or u heavy chain constant region. In an embodiment, the light or heavy chain constant region is a fragment, derivative, variant, or mutant of the natural constant region.

In an embodiment, the antibody provided herein further comprises a human light chain κ or λ constant domain or fragment thereof. The amino acid sequence of the light chain constant region is as follows:

Human light chain κ constant domain amino acid sequence: (SEQ ID NO: 101); and

Human light chain λ constant domain amino acid sequence: (SEQ ID NO: 102).

In one embodiment, the antibodies provided herein further comprise a human heavy chain constant domain or fragment thereof.

The amino acid sequence of the heavy chain constant region is as follows:

Human heavy chain constant region amino acid sequence (hIgG2): (SEQ ID NO: 103);

Human heavy chain constant region amino acid sequence (hIgG4): (SEQ ID NO: 104); and Human heavy chain constant region amino acid sequence (hIgG4): (SEQ ID NO: 124).

In one embodiment, the GIPR antibody provided herein comprises one light chain domain amino acid sequence, wherein the sequence is selected from V1 (SEQ ID NO: 125) and V2 (SEQ ID NO: 126) provided herein. In one embodiment, the light chain domain amino acid sequence of the GIPR antibody differs from one light chain domain amino acid sequence of V1 and V2 by fifteen, fourteen, thirteen, twelve, eleven, ten, nine, eight, seven, six, five, four, three, two or one amino acid, wherein the difference in each sequence is independently a deletion, insertion or substitution of one amino acid residue. In another embodiment, the light chain domain amino acid sequence of the GIPR antibody comprises an amino acid sequence at least 70%, at least 75%, at least 80%, at least 85%, at least 90%, at least 95%, at least 97% and at least 99% identical to one light chain domain amino acid sequence of V1 and V2. In another embodiment, the light chain domain polynucleotide encoding sequence of the GIPR antibody comprises a polynucleotide sequence at least 70%, at least 75%, at least 80%, at least 85%, at least 90%, at least 95%, at least 97% and at least 99% identical to one light chain domain polynucleotide encoding sequence of V1 and V2. In another embodiment, the light chain domain polynucleotide encoding sequence of the GIPR antibody comprises a polynucleotide sequence that hybridizes under moderately stringent conditions to the complement of one light chain domain polynucleotide encoding sequence of V1 and V2. In another embodiment, the light chain domain polynucleotide encoding sequence of the GIPR antibody comprises a polynucleotide sequence that hybridizes under stringent conditions to the complement of one light chain domain polynucleotide encoding sequence of V1 and V2.

In one embodiment, the GIPR antibody provided herein comprises one heavy chain domain amino acid sequence, and the sequence is selected from W1 (SEQ ID NO: 127), W2 (SEQ ID NO: 128), W3 (SEQ ID NO: 129), W4 (SEQ ID NO: 130), W5 (SEQ ID NO: 131), W6 (SEQ ID NO: 132), W7 (SEQ ID NO: 133), W8 (SEQ ID NO: 134), and W9 (SEQ ID NO: 135) provided herein. In one embodiment, the heavy chain domain amino acid sequence of the GIPR antibody differs from one heavy chain domain amino acid sequence of W1, W2, W3, W4, W5, W6, W7, W8 and W9 by fifteen, fourteen, thirteen, twelve, eleven, ten, nine, eight, seven, six, five, four, three, two or one amino acid, wherein the difference in each sequence is independently a deletion, insertion or substitution of one amino acid residue. In another embodiment, the heavy chain domain amino acid sequence of the GIPR antibody comprises an amino acid sequence at least 70%, at least 75%, at least 80%, at least 85%, at least 90%, at least 95%, at least 97% and at least 99% identical to one heavy chain domain amino acid sequence of W1, W2, W3, W4, W5, W6, W7, W8 and W9. In another embodiment, the heavy chain domain polynucleotide encoding sequence of the GIPR antibody comprises a polynucleotide sequence at least 70%, at least 75%, at least 80%, at least 85%, at least 90%, at least 95%, at least 97% and at least 99% identical to one heavy chain domain polynucleotide encoding sequence of W1, W2, W3, W4, W5, W6, W7, W8 and W9. In another embodiment, the heavy chain domain polynucleotide encoding sequence of the GIPR antibody comprises a polynucleotide sequence that hybridizes under moderately stringent conditions to the complement of one heavy chain domain polynucleotide encoding sequence of W1, W2, W3, W4, W5, W6, W7, W8 and W9. In another embodiment, the heavy chain domain polynucleotide encoding sequence of the GIPR antibody comprises a polynucleotide sequence that hybridizes under stringent conditions to the complement of one heavy chain domain polynucleotide encoding sequence of W1, W2, W3, W4, W5, W6, W7, W8 and W9.

In another embodiment, the antibody provided herein is an antibody comprising the combination of V1W1 (SEQ ID NO: 125 and SEQ ID NO: 127), V1W2 (SEQ ID NO: 125 and SEQ ID NO: 128), V1W3 (SEQ ID NO: 125 and SEQ ID NO: 129), V1W4 (SEQ ID NO: 125 and SEQ ID NO: 130), V1W5 (SEQ ID NO: 125 and SEQ ID NO: 131), V1W6 (SEQ ID NO: 125 and SEQ ID NO: 132), V1W7 (SEQ ID NO: 125 and SEQ ID NO: 133), V1W8 (SEQ ID NO: 125 and SEQ ID NO: 134), V1W9 (SEQ ID NO: 125 and SEQ ID NO: 135), V2W1 (SEQ ID NO: 126 and SEQ ID NO: 127), V2W2 (SEQ ID NO: 126 and SEQ ID NO: 128), V2W3 (SEQ ID NO: 126 and SEQ ID NO: 129), V2W4 (SEQ ID NO: 126 and SEQ ID NO: 130), V2W5 (SEQ ID NO: 126 and SEQ ID NO: 131), V2W6 (SEQ ID NO: 126 and SEQ ID NO: 132), V2W7 (SEQ ID NO: 126 and SEQ ID NO: 133), V2W8 (SEQ ID NO: 126 and SEQ ID NO: 134), or V2W9 (SEQ ID NO: 126 and SEQ ID NO: 135).

In one embodiment, the antibody provided herein is an antibody comprising the combination of V1W1 (SEQ ID NO: 125 and SEQ ID NO: 127). In one embodiment, the antibody provided herein is an antibody comprising the combination of V1W2 (SEQ ID NO: 125 and SEQ ID NO: 128). In one embodiment, the antibody provided herein is an antibody comprising the combination of V1W3 (SEQ ID NO: 125 and SEQ ID NO: 129). In one embodiment, the antibody provided herein is an antibody comprising the combination of V1W4 (SEQ ID NO: 125 and SEQ ID NO: 130). In one embodiment, the antibody provided herein is an antibody comprising the combination of V1W5 (SEQ ID NO: 125 and SEQ ID NO: 131). In one embodiment, the antibody provided herein is an antibody comprising the combination of V1W6 (SEQ ID NO: 125 and SEQ ID NO: 132). In one embodiment, the antibody provided herein is an antibody comprising the combination of V1W7 (SEQ ID NO: 125 and SEQ ID NO: 133). In one embodiment, the antibody provided herein is an antibody comprising the combination of V1W8 (SEQ ID NO: 125 and SEQ ID NO: 134). In one embodiment, the antibody provided herein is an antibody comprising the combination of V1W9 (SEQ ID NO: 125 and SEQ ID NO: 135). In one embodiment, the antibody provided herein is an antibody comprising the combination of V2W1 (SEQ ID NO: 126 and SEQ ID NO: 127). In one embodiment, the antibody provided herein is an antibody comprising the combination of V2W2 (SEQ ID NO: 126 and SEQ ID NO: 128). In one embodiment, the antibody provided herein is an antibody comprising the combination of V2W3 (SEQ ID NO: 126 and SEQ ID NO: 129). In one embodiment, the antibody provided herein is an antibody comprising the combination of V2W4 (SEQ ID NO: 126 and SEQ ID NO: 130). In one embodiment, the antibody provided herein is an antibody comprising the combination of V2W5 (SEQ ID NO: 126 and SEQ ID NO: 131). In one embodiment, the antibody provided herein is an antibody comprising the combination of V2W6 (SEQ ID NO: 126 and SEQ ID NO: 132). In one embodiment, the antibody provided herein is an antibody comprising the combination of V2W7 (SEQ ID NO: 126 and SEQ ID NO: 133). In one embodiment, the antibody provided herein is an antibody comprising the combination of V2W8 (SEQ ID NO: 126 and SEQ ID NO: 134). In one embodiment, the antibody provided herein is an antibody comprising the combination of V2W9 (SEQ ID NO: 126 and SEQ ID NO: 135).

In one embodiment, the GIPR antibodies provided herein are selected from mouse-derived antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, quadruple-chain antibodies, Fab fragments, F(ab')x fragments, structural domain antibodies, IgD antibodies, IgE antibodies, IgM antibodies, IgG1 antibodies, IgG2 antibodies, IgG3 antibodies, or IgG4 antibodies.

In one embodiment, the GIPR antibody provided herein is a GIPR monoclonal antibody.

In another embodiment, the GIPR antibody provided herein is a monoclonal antibody comprising a combination of amino acid sequences selected from the list below: SEQ ID NO: 61 and SEQ ID NO: 72, SEQ ID NO: 62 and SEQ ID NO: 73, SEQ ID NO: 63 and SEQ ID NO: 74, SEQ ID NO: 64 and SEQ ID NO: 74, SEQ ID NO: 65 and SEQ ID NO: 75, SEQ ID NO: 66 and SEQ ID NO: 76, SEQ ID NO: 67 and SEQ ID NO: 77, SEQ ID NO: 68 and SEQ ID NO: 77, SEQ ID NO: 69 and SEQ ID NO: 78, SEQ ID NO: 70 and SEQ ID NO: 79, and SEQ ID NO: 71 and SEQ ID NO: 80.

In one embodiment, the GIPR antibody provided herein is a mouse GIPR antibody. In another embodiment, the GIPR antibody provided herein is a humanized GIPR antibody.

In one embodiment, the GIPR antibody provided herein reduces the human GIP signal transduction with an IC50 value of about 1 nM to 200 nM or about 1 nM to 100 nM.

Antibodies and Antibody Fragments

In one embodiment, the antibody provided herein is a full-length antibody (including polyclonal, monoclonal, chimeric, humanized or human antibody with full length heavy and/or light chains). In another embodiment, the antibody provided herein is an antibody fragment, for example, F(ab')2, Fab, Fab', Fv, Fc, or Fd fragment, single domain antibodies, single-chain antibodies, maxibodies, minibodies, intrabodies, double-chain antibodies, triple-chain antibodies, tetra-chain antibodies, v-NAR or bis-scFv (see e.g., Hollinger and Hudson, 2005*, Nature Biotechnology,* 23:1126-1136). In another embodiment, the antibody provided herein also includes antibody polypeptides such as those disclosed in U.S. Pat. No. 6,703,199, including fibronectin polypeptide monobodies. In another embodiment, the antibody provided herein also includes other antibody polypeptides disclosed in U.S. Patent Publication 2005/0238646, which are single-chain polypeptides.

In one embodiment, the variable regions of the IgG gene expressing a monoclonal antibody of interest in a hybridoma are amplified using nucleotide primers. These primers can be synthesized by one of ordinary skill in the art, or can be purchased commercially. Primers for mouse and human variable regions including $V_{Ha}$, $V_{Hb}$, $V_{Hc}$, $V_{Ha}$, $C_{H1}$, $V_L$ and $C_L$ regions can be purchased commercially. These primers can be used to amplify heavy or light chain variable regions, which can then be inserted into vectors such as IMMUNO- ZAP™H or IMMUNOZAP™L (Stratagene), respectively. These vectors can then be introduced into *E. coli*, yeast, or mammalian-based systems for expression. Large amounts of a single-chain protein containing a fusion of the $V_H$ and $V_L$ regions can be produced using these methods (see Bird et al., 1988, *Science* 242:423-426).

It should be understood by one skilled in the art that certain proteins, such as antibodies, can undergo a variety of post-translational modifications. The types and extents of these modifications often depend on the host cell lines used to express the protein as well as the culture conditions. Such modifications can include variations in glycosylation, methionine oxidation, diketopiperizine formation, aspartate isomerization and asparagine deamidation. A frequent modification is the loss of a carboxyl-terminal basic residue (such as lysine or arginine) due to the action of carboxypeptidases (as described in Harris, 1995, *Journal of Chromatography* 705:129-134).

A common method for production of a murine monoclonal antibody is by hybridoma cells. Monoclonal antibodies can be isolated and purified by a variety of well-established techniques. Such isolation techniques include affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). A monoclonal antibody can be purified by affinity chromatography using an appropriate ligand selected based on particular properties of the antibody (e.g., heavy or light chain isotype, binding specificity, etc.). Examples of suitable ligands immobilized on a solid support include Protein A, Protein G, an anti-constant region (light chain or heavy chain) antibody, an anti-idiotype antibody, and a TGF-β binding protein, or a fragment or variant thereof.

Molecular evolution of the complementarity determining regions (CDRs) in the center of the antibody binding site also has been used to remold antibodies with increased affinities, for example, antibodies having increased affinities for c-erbB-2, as described by Schier et al., 1996, *J. Mol. Biol.* 263:551-567. Accordingly, such techniques can be used in preparing antibodies against GIPR.

Antibodies against human GIPR can be used, for example, in assays to detect the presence of GIPR, either in vitro or in vivo.

Antibodies can also be prepared by any of the conventional techniques. For example, they can be purified from cells that naturally express them (e.g., an antibody can be purified from a hybridoma that produces it) or produced in recombinant expression systems using any technique known in the art. For example, Monoclonal Antibodies, Hybridomas: A New Dimension in Biological Analyses, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988). This is discussed in the nucleic acid section below.

Antibodies can be prepared and screened for desired properties by any known techniques. Some techniques relate to the isolation of nucleic acids encoding polypeptide chains (or portions thereof) of related antibodies (e.g., anti-GIPR antibodies) and manipulation of nucleic acid through recombinant DNA techniques. Nucleic acids can be fused with another relevant nucleic acid or modified (e.g., induced mutations or other conventional techniques) to add, delete or replace one or more amino acid residues.

When it is desired to improve the affinity of antibodies according to the invention containing one or more of the above-mentioned CDRs, such antibodies can be obtained by a number of affinity maturation protocols, including maintaining the CDRs (Yang et al., 1995, *J. Mol. Biol.*, 254:392-403), chain shuffling (Marks et al., 1992, *Bio/Technology*, 10:779-783), use of mutation strains of *E. coli*. (Low et al., 1996, *J. Mol. Biol.*, 250:350-368), DNA shuffling (Patten et al., 1997, *Curr. Opin. Biotechnol.*, 8:724-733), phage display (Thompson et al., 1996, *J. Mol. Biol.*, 256:7-88) and additional PCR techniques (Crameri et al., 1998, *Nature*, 391:288-291). All of these methods or affinity maturation are discussed in Vaughan et al., 1998, *Nature Biotechnology*, 16:535-539.

In one embodiment, fragments of the GIPR antibody are provided herein. Such fragments can comprise entirely antibody-derived sequences or additional sequences. Examples of antigen binding fragments include Fab, F(ab') 2, single chain antibodies, diabodies, tribodies, tetrabodies, and domain antibodies. Other examples are provided in Lunde et al., 2002, *Biochem. Soc. Trans.* 30:500-06.

Single chain antibodies can be formed by linking heavy and light chain variable domain (Fv region) fragments via an amino acid bridge (short peptide linker), resulting in a single polypeptide chain. Such single-chain Fvs (scFvs) have been prepared by fusion DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different VL and VH-comprising polypeptides, multimeric scFvs that bind to different epitopes can be formed (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544; de Graaf et al., 2002, *Methods Mol. Biol.* 178:379-87. Single chain antibodies derived from antibodies provided herein including, but not limited to, scFvs comprising the variable domain combination L1H1, are encompassed by the present invention.

Antigen binding fragments derived from an antibody can also be obtained, for example, by proteolytic hydrolysis of the antibody, for example, pepsin or papain digestion of a whole antibody according to conventional methods. By way of example, antibody fragments can be produced by enzymatic cleavage of antibodies with pepsin to provide a SS fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoffet et al., 1960, *Arch. Biochem. Biophys.* 89:230; Porter, 1959, *Biochem. J.* 73:119; Edelman et al., *Methods in Enzymology* 1:422 (Academic Press 1967); and by Andrews, S. M. and Titus, J. A. in *Current Protocols in Immunology* (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques can also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDRs. Such polynucleotides are prepared, for example, by using the polymerase chain reaction to synthesize the variable region using mRNA or antibody-producing cells as a template (see, for example, Larrick et al., 1991, *Methods: A Companion to Methods in Enzymology* 2:106; Courtenay-Luck, "(Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression or Antibodies," in Monoclonal Antibodies: Principles and Applications, Birch et al., (eds.), page 137 (Wiley-Liss, Inc. 1995). The antibody fragment further can comprise at least one variable region domain of an antibody described herein. Thus, for example, the V region domain can be monomeric and be a $V_H$ or $V_L$ domain, which can bind to GIPR with an affinity of $1\times10^{-7}$ M or less as described below.

The variable region domain can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing one CDR and optionally one or more framework amino acids from a first antibody and the remainder of the variable region domain from a second antibody.

The variable region domain can be covalently attached at a C-terminal amino acid to at least one other antibody domain or a fragment thereof. Thus, for example, a $V_H$ domain that is present in the variable region domain can be linked to an immunoglobulin $C_{H1}$ domain or a fragment thereof. Similarly, a $V_L$ domain can be linked to a $C_K$ domain or a fragment thereof. In this way, for example, the antibody can be a Fab fragment, wherein the antigen binding domain contains associated $V_H$ and $V_L$ domains covalently linked at their C-termini to a $C_{H1}$ and $C_K$ domain, respectively. The $C_{H1}$ domain can be extended with further amino acids, for example to provide a hinge region or a portion of a hinge region domain as found in a Fab' fragment, or to provide further domains, such as antibody $C_{H2}$ and $C_{H3}$ domains.

Derivatives and Variants of Antibodies

The nucleotide sequences of L1 and H1 can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, *Gene* 42:133; Bauer et al., 1985, *Gene* 37:73; Craik, 1985, *BioTechniques,* 3:12-19; Smith et al., 1981, Genetic Engineering: Principles and Methods, Plenum Press; and U.S. Pat. Nos. 4,518,584 and 4,737,462. These and other methods can be used to make, for example, derivatives of GIPR antibodies that have a desired property, for example, an increase in affinity, avidity, or specificity for GIPR or in vivo or in vitro stability, or reduced in vivo side-effects as compared to the underivatized antibody.

Other derivatives of GIPR antibodies within the scope or this invention include covalent or aggregative conjugates of anti-GIPR antibodies, or fragments thereof, with other proteins or polypeptides, such as by expression or recombinant fusion proteins comprising heterologous polypeptides fused to the N-terminus or C-terminus of an anti-GIPR antibody polypeptide. For example, the conjugated peptide can be a heterologous signal (or leader) polypeptide, e.g., the yeast alpha-factor leader or a peptide such as an epitope tag. An antibody containing fusion proteins can comprise peptides added to facilitate purification or identification of antigen binding protein (e.g., poly-His). An antibody also can be linked to the FLAG peptide as described in Hopp et al., 1988, *Bio/Technology* 6:1204, and U.S. Pat. No. 5,011,912. The FLAG peptide is highly antigenic and provides an epitope reversibly bound by a specific monoclonal antibody (mAb), enabling rapid assay and facile purification of an expressed recombinant protein. Reagents useful for preparing fusion proteins in which the FLAG peptide is fused to a given polypeptide are commercially available (Sigma, St. Louis, Mo.). In another embodiment, oligomers that contain one or more antibodies can be employed as GIPR antagonists. Oligomers can be in the form of covalently linked or non-covalently linked dimers, trimers, or higher oligomers. Oligomers comprising two or more antibodies are contemplated for use, with one example being a homodimer. Other oligomers include heterodimers, homotrimers, heterotrimers, homotetramers, heterotetramers, etc.

One embodiment is directed to oligomers comprising multiple antibodies joined via covalent or non-covalent interactions between peptide moieties fused to the antibodies. Such peptides can be peptide linkers (spacers), or peptides that have the property of promoting oligomerization. Leucine zippers and certain polypeptides derived from antibodies are among the peptides that can promote oligomerization of antibodies attached thereto, as described in more detail below.

In particular embodiments, the oligomers comprise from two to four antibodies. The antibodies of the oligomer can be in any form, such as any of the forms described above, e.g., variants or fragments. Preferably, the oligomers comprise antibodies that show GIPR binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *PNAS USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11. One embodiment provided herein is directed to a dimer comprising two fusion proteins created by fusing an GIPR binding fragment of an anti-GIPR antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-GIPR antibody can be substituted for the variable portion of an antibody heavy and/or light chain.

Alternatively, the oligomer is a fusion protein comprising multiple antibodies, with or without peptide linkers (spacer peptides). Among the suitable peptide linkers are those described in U.S. Pat. Nos. 4,751,180 and 4,935,233.

Another method for preparing oligomeric antibodies involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one method, recombinant fusion proteins comprising an anti-GIPR antibody fragment or derivative fused to a leucine zipper peptide are expressed in suitable host cells, and the soluble oligomeric anti-GIPR antibody fragments or derivatives that form are recovered from the culture supernatant.

In another embodiment, the antibody derivatives can comprise at least one of the CDRs disclosed herein. For example, one or more CDR can be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides can be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody provided herein can have at least one amino acid substitution, providing that the antibody retains binding specificity. Therefore, modifications to the antibody structures are encompassed within the scope of the invention. These can include amino acid substitutions, which may be conservative or non-conservative, that do not destroy the human GIPR binding capability of an antibody. Conservative amino acid substitutions may encompass non-naturally occurring amino acid residues, which are typically incorporated by chemical peptide synthesis rather than by synthesis in biological systems. This include peptidomimetics and other reversed or inverted forms of amino acid moieties. A conservative amino acid substitution can also involve a substitution of a native amino acid residue with a normative residue such that there is little or no effect on the polarity or charge of the amino acid residue at that position. Non-conservative substitutions can involve the exchange of a member of one class of amino acids or amino acid mimetics for a member from another class with different physical properties (e.g., size, polarity, hydrophobicity, charge).

Moreover, one skilled in the art may generate variants to be tested, which contain a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

One skilled in the art will be able to determine suitable variants of the polypeptide as set forth herein using well-known techniques. In certain embodiments, one skilled in the art may identify suitable areas of the molecule that may be changed without destroying activity by targeting regions not to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult, 1996, *Curr. Op. Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276 and Chou et al., *Biophys. J.* 26:367-384. Moreover, computer programs are currently available to assist with predicting secondary structure. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within the structure of a polypeptide or protein. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci. USA* 84: 4355-4358), and "evolutionary linkage" (see Holm, supra (1999), and Brenner, supra (1997)). In certain embodiments, variants of antibodies include glycosylation variants, wherein the number and/or type of glycosylation sites have been altered compared to the amino acid sequences of a parent polypeptide. In certain embodiments, variants comprise a greater or lesser number of N-linked glycosylation sites than the native protein. Alternatively, elimination of such a sequence by substitutions removes an existing N-linked carbohydrate chain. Also provided is a rearrangement of N-linked carbohydrate chains, wherein one or more N-linked glycosylation sites (typically those that are naturally occurring) are eliminated and one or more new N-linked sites are created. Additional preferred antibody variants include cysteine variants, wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human GIPR, or to increase or decrease the affinity of the antibodies to human GIPR described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically cannot substantially change the structural characteristics of the parent sequence (e.g., a replacement amino acid should not break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (Branden and Tooze, Eds., Garland Publishing, New York, N.Y. (1991)); and Thornton et al., 1991, *Nature* 354:105, each of which is incorporated herein by reference.

In certain embodiments, antibodies of the invention can be chemically bonded with polymers, lipids, or other moieties.

The antigen binding agents can comprise at least one of the CDRs described herein incorporated into a biocompatible framework structure. In one embodiment, the biocompatible framework structure comprises a polypeptide or portion thereof that is sufficient to form a conformationally stable structural support, or framework, or scaffold, which is able to present one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains can be used (see, e.g., Nygren and Uhlen, 1997, *Current Opinion in Structural Biology* 7:463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, light chain CDR1, CDR2 and CDR3 can have at least one amino acid substitution, provided that the antibody retains the binding specificity of the non-substituted CDR. The non-CDR portion of the antibody can be a non-protein molecule, wherein the binding agent cross-blocks the binding of an antibody disclosed herein to human GIPR and/or inhibits the activity of GIP signaling through the receptor. The non-CDR portion of the antibody can be a non-protein molecule in which the antibody exhibits a similar binding pattern to human GIPR peptides in a competition binding assay as that exhibited by at least one of antibodies L2H2/L6H5, and/or neutralizes the activity of GIP. The non-CDR portion of the antibody can be composed of amino acids, wherein the antibody is a recombinant binding protein or a synthetic peptide, and the recombinant binding protein cross-blocks the binding of an antibody disclosed herein to human GIPR and/or neutralizes GIP's activity in vitro or in vivo. The non-CDR portion of the antibody can be composed of amino acids, wherein the antibody is a recombinant antibody, and the recombinant antibody exhibits a similar binding pattern to human GIPR peptides in a competition binding assay as exhibited by at least one of the antibodies L2H2/L6H5, and/or neutralizes GIP's activity.

Fusion Protein of GIPR Antibody and GLP-1 or Reverse GLP-1

In one embodiment, provided herein is a fusion protein of GIPR antibody and GLP-1, comprising an antibody that binds specifically to GIPR, and one, two, three, four, five, six, seven, or eight GLP-1 fragments or reverse GLP-1 fragments, wherein the fusion protein connects the carboxy terminus of GLP-1 fragment to the amino terminus of the light or heavy chain of GIPR antibody through a peptide linker sequence (Linker), or connects the amino terminus of reverse GLP-1 fragment to the carboxy terminus of the light or heavy chain of GIPR antibody.

In another embodiment, provided herein is a fusion protein of GIPR antibody and GLP-1, comprising an antibody that binds specifically to GIPR, and one, two, three, four, five, six, seven, or eight GLP-1 fragments; the fusion protein connects the carboxy terminus of a GLP-1 fragment with the amino terminus of a GIPR antibody light chain or heavy chain through a peptide linker sequence (Linker).

In another embodiment, provided herein is a fusion protein of GIPR antibody and GLP-1, comprising an antibody that binds specifically to GIPR, and one, two, three, four, five, six, seven, or eight reverse GLP-1 fragments; the fusion protein connects the amino terminus of a reverse GLP-1 fragment to the carboxy terminus of a GIPR antibody light chain or heavy chain through a peptide linker sequence (Linker).

In another embodiment, provided herein is a fusion protein of GIPR antibody and GLP-1, comprising an antibody that binds specifically to GIPR, and one, two, three, or four GLP-1 fragments; the fusion protein connects the carboxy terminus of a GLP-1 fragment with the amino terminus of a GIPR antibody light chain or heavy chain through a peptide linker sequence (Linker).

In another embodiment, provided herein is a fusion protein of GIPR antibody and GLP-1, comprising an antibody that binds specifically to GIPR, and one, two, three, or four reverse GLP-1 fragments; the fusion protein connects the amino terminus of a reverse GLP-1 fragment to the carboxy terminus of a GIPR antibody light chain or heavy chain through a peptide linker sequence (Linker).

In another embodiment, provided herein is a fusion protein of GIPR antibody and GLP-1, comprising an antibody that binds specifically to GIPR, and two GLP-1 fragments; the fusion protein connects the carboxy terminus of a GLP-1 fragment with the amino terminus of a GIPR antibody light chain or heavy chain through a peptide linker sequence (Linker).

In another embodiment, provided herein is a fusion protein of GIPR antibody and GLP-1, comprising an antibody that specifically binds to GIPR, and two reverse GLP-1 fragments; the fusion protein connects the amino terminus of a reverse GLP-1 fragment to the carboxy terminus of a GIPR antibody light chain or heavy chain through a peptide linker sequence (Linker).

In another embodiment, provided herein is a GLP-1 fusion protein comprising a GIPR antibody and two GLP-1 fragments; the fusion protein connects the carboxy terminus of a GLP-1 fragment with the amino terminus of a GIPR antibody light chain through a peptide linker sequence (Linker): N'-GLP-1-Linker-R-C'; or connects the carboxy terminus of a GLP-1 fragment to the amino terminus of a GIPR antibody heavy chain: N'-GLP-1-Linker-R-C'; wherein: N' represents the amino terminus of the fusion protein polypeptide chain, C' represents the carboxy terminus of the fusion protein polypeptide chain, GLP-1 represents GLP-1 fragment, R represents the amino acid sequence of a light chain or heavy chain of GIPR antibody, and Linker represents a peptide linker sequence.

In another embodiment, provided herein is a GLP-1 fusion protein comprising GIPR antibody and two reverse GLP-1 fragments; the fusion protein connects the amino terminus of a reverse GLP-1 fragment to the carboxy terminus of a GIPR antibody light chain: N'-R-Linker-reverse GLP-1-C'; or connects the amino terminus of a reverse GLP-1 fragment through a peptide linker sequence (Linker) to the carboxy terminus of a GIPR antibody heavy chain: N'-R-Linker-reverse GLP-1-C'; wherein: N' represents the amino terminus of the fusion protein polypeptide chain, C' represents the carboxy terminus of the fusion protein polypeptide chain, and the reverse GLP-1 represents a reverse GLP-1 fragment, R represents the amino acid sequence of the light chain or heavy chain of a GIPR antibody, and Linker represents a peptide linker sequence.

In a further embodiment, provided herein is a GLP-1 fusion protein comprising a GIPR antibody and two GLP-1 fragments; the fusion protein connects the carboxy terminus of a GLP-1 fragment through a peptide linker sequence (Linker) to the amino terminal of a GIPR antibody light chain: N'-GLP-1-Linker-R-C'; wherein: N' represents the amino terminus of the fusion protein polypeptide chain, C' represents the carboxy terminus of the fusion protein polypeptide chain, GLP-1 represents a GLP-1 fragment, R represents the amino acid sequence of a GIPR antibody light chain, and Linker represents a peptide linker sequence.

In one embodiment, in the GLP-1 fusion protein provided herein, wherein the GLP-1 fragment is independently selected from one of the following amino acid sequences: SEQ ID NO: 105, SEQ ID NO: 106, SEQ ID NO: 107, SEQ ID NO: 108, and SEQ ID NO: 109. In one embodiment, in the GLP-1 fusion protein provided herein, wherein the reverse GLP-1 fragment is independently selected from one of the following amino acid sequences: SEQ ID NO: 119, SEQ ID NO: 120, SEQ ID NO: 121, SEQ ID NO: 122, and SEQ ID NO: 123.

In one embodiment, in the GLP-1 fusion protein provided herein, wherein the peptide linker (Linker) sequence independently comprises from 1 to 200 amino acid residues, from 2 to 100 amino acid residues, from 5 to 50 amino acid residues, from 6 to 25 amino acid residues, or from 10 to 20 amino acid residues.

In another embodiment, in the GLP-1 fusion protein provided herein, wherein the peptide linker (Linker) sequence is independently selected from the following amino acid sequences: SEQ ID NO: 110, SEQ ID NO: 111, And SEQ ID NO: 112.

Nucleic Acids

In one aspect, the present invention provides isolated nucleic acid molecules that encode the antibodies provided herein. The nucleic acids comprise, for example, polynucleotides that encode all or part of an antibody or GLP-1 fusion protein, for example, one or both chains of an antibody of the invention, or a fragment, derivative, mutein, or variant thereof; polynucleotides sufficient for use as hybridization probes; PCR primers or sequencing primers for identifying, analyzing, mutating or amplifying a polynucleotide encoding a polypeptide; anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) can be isolated from B-cells of mice that have been immunized with GIPR antigen. The nucleic acid of the antibody or GLP-1 fusion protein can be isolated by conventional procedures such as polymerase chain reaction (PCR).

Nucleic acid sequences encoding the variable regions of the heavy and light chain are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antibody or GLP-1 fusion protein provided herein.

The invention further provides nucleic acids that hybridize to other nucleic acids (e.g., nucleic acids comprising a nucleotide sequence of any of L2H2/L6H5) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., Eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antibody) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. No matter how it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, nucleotide sequences provided herein for L1 to L11 and H1 to H9, or GLP-1 fusion protein, or fragments, variants, or derivatives thereof, are mutated such that they encode amino acid sequences provided herein for L1 to L11 and H1 to H9, comprising one or more deletions or substitutions of amino acid residues to result in sequences bearing two or more different amino acid residues. In another embodiment, the mutagenesis inserts an amino acid adjacent to one or more amino acid residues shown herein for L1 to L11 and H1 to H9 or GLP-1 fusion protein to result in sequences with two or more different amino acid residues. Alternatively, one or more mutations can be introduced into a nucleic acid that selectively change the biological activity. (e.g., binding to GIPR) of a polypeptide that it encodes. For example, the mutation can quantitatively or qualitatively change the biological activity. Examples of quantitative changes include increasing, reducing or eliminating the activity. Examples of qualitative changes include changing the antigen specificity of the antibody or GLP-1 fusion protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a GIPR binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the vectors provided herein comprise a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors provided herein can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, *Science* 236:1237, the disclosure of each of which is incorporated by reference herein in its entirety), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see Id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram-negative or gram-positive organisms, for example, *E. coli* or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, *Cytotechnology* 28:31) or CHO strain DXB-11, which is deficient in DHFR (see Urlaub et al., 1980, *Proc. Natl. Acad. Sci. USA* 77:4216-20). Additional CHO cell lines include CHO-K1 (ATCC #CCL-61), EM9 (ATCC #CRL-1861), and W20 (ATCC #CRL-1862). Additional host cells include the COS-7 line of monkey kidney cells (ATCC #CRL-1651) (see Gluzman et al., 1981, *Cell* 23:175), L cells, C127 cells, 3T3 cells (ATCC CCL-163), AM-1/D cells (described in U.S. Pat. No. 6,210,924), HeLa cells, BHK (ATCC CRL-10) cell lines, the CV1/EBNA cell line derived from the African green monkey kidney cell line CV1 (ATCC CCL-70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, N.Y., 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of a polypeptide, and the polypeptide recovered by conventional protein purification procedures. One such purification procedure is described in the Examples below. Polypeptides contemplated for use herein include substantially homogeneous recombinant mammalian GIPR antibody or GLP-1 fusion protein polypeptides substantially free of contaminating endogenous materials.

Activity of GIPR Antibody

The activity of the GIPR antibody refers to the effect of the antibody provided herein in binding specifically to GIPR, inhibiting or blocking GIP signaling, thereafter demonstrating a therapeutic biological effect, for example, in treating obesity, T2DM and/or Non-Alcoholic Steatohepatitis (NASH). The term "decreasing the biological activity of GIP signaling" or "inhibiting or blocking a biological activity of GIP signaling" refers to an effect of GIPR antibody or its GLP-1 fusion protein thereof in inhibiting or blocking the downstream cellular responses to GIP by binding to GIPR in vivo. Those responses include but not limited to insulinotropic effect, promoting fat accumulation, and inhibiting lipolysis. In one embodiment, a mouse antibody or humanized antibody provided herein specifically binds to a human GIPR. Such antibodies comprise antagonistic or neutralizing antibodies that reduce or neutralize GIP signaling.

In one embodiment, the $K_d$ of the antibody provided herein binding to human GIPR is ranging approximately from 0.01 nM to 1000 nM, from 0.1 nM to 500 nM, from 0.5 nM to 200 nM, from 1 nM to 200 nM, or from 10 nM to 100 nM. In another embodiment, the $K_d$ of the antibody provided herein binding to GIPR is approximately from 1 nM to 200 nM. In yet another embodiment, the $K_d$ of the antibody provided herein binding to GIPR is approximately from 1 nM to 100 nM. In yet another embodiment, the $K_d$ of the antibody provided herein binding to GIPR is approximately 1 nM, 2 nM, 5 nM, 10 nM, 20 nM, 30 nM, 40 nM, 50 nM, 60 nM, 70 nM, 80 nM, 90 nM, or 100 nM.

In one embodiment, the $IC_{50}$ of the antibody provided herein in antagonizing GIP signaling is approximately from 0.01 nM to 500 nM, from 0.1 nM to 200 nM, from 0.5 nM to 200 nM, from 1 nM to 200 nM, or from 10 nM to 100 nM. In another embodiment, the $IC_{50}$ of the antibody provided herein in antagonizing GIP signaling is approximately from 1 nM to 200 nM. In yet another embodiment, the $IC_{50}$ of the antibody provided herein in antagonizing GIP signaling is approximately from 10 nM to 100 nM. In yet another embodiment, the $IC_{50}$ of the antibody provided herein in antagonizing GIP signaling is approximately 1 nM, 2 nM, 5 nM, 10 nM, 20 nM, 30 nM, 40 nM, 50 nM, 60 nM, 70 nM, 80 nM, 90 nM, or 100 nM.

In one embodiment, the antibody provided herein specifically binds to GIPR with one or more following properties:

a. providing the substantially similar Kd as a reference antibody in binding to GIPR;
b. providing the substantially similar IC50 as a reference antibody in antagonizing GIPR activated by GIP; and
c. cross-competing binding with a reference antibody to human GIPR.

In another embodiment, the antibody provided herein is an antibody with one or more following properties:

a. providing the same or better Kd than a reference antibody in binding to GIPR;
b. providing the same or better IC50 than a reference antibody in antagonizing GIPR activated by GIP; and
c. cross-competing binding with a reference antibody to human GIPR.

In one embodiment, the reference antibody comprises a combination of light chain variable domain amino acid sequence SEQ ID NO: 66 and heavy chain variable domain amino acid sequence SEQ ID NO: 76.

In one embodiment, the reference antibody comprises a combination of light chain variable domain amino acid sequence SEQ ID NO: 68 and heavy chain variable domain amino acid sequence SEQ ID NO: 77.

In another embodiment, the reference antibody is monoclonal antibody L2H2, L6H5, or L10H8.

As used herein, the term "substantially similar" means comparable to, or approximately 200%, 180%, 160%, 150%, 140%, 120%, 110%, 100%, 99%, 98%, 97%, 95%, 90%, 85%, 80%, 75%, 70%, 65%, or 50% of the $IC_{50}$ or $K_d$ of a reference antibody. In one embodiment, the reference antibody is, for example, an antibody comprising a combination of a heavy chain SEQ ID NO:76 and light chain SEQ ID NO:66. In another embodiment, the reference antibody includes GIPR antibodies L2H2, L6H5, or L10H8.

Biological Activity of the Fusion Protein of GIPR Antibody and GLP-1

The biological activity of the fusion protein of GIPR antibody and GLP-1 comprises the biological activity of GLP-1 and the activity of GIPR antibody. The activity of GIPR antibodies is as described above. "GLP-1 biological activity" refers to the biological activity of the fusion protein of GIPR antibody and GLP-1 that binds in vivo and activates GLP-1 receptor and causes cellular signaling response, and shows therapeutic effects, such as obesity, Type 2 diabetes, or non-alcoholic steatohepatitis. The signaling response comprises, but is not limited to, increased insulin secretion, suppression of glucagon secretion, suppression of appetite, weight loss, induction of satiety, inhibition of apoptosis, induction of pancreatic β cell proliferation, and pancreatic β cell differentiation. Combining the biological activities of GLP-1 and GIPR antibodies, the GLP-1 fusion protein provided herein can be used to treat various diseases and disorders associated with GLP-1R and GIPR. The fusion protein exerts its biological effect by acting on GLP-1R and/or GIPR, so the GLP-1 fusion protein treatment provided herein can be used to treat subjects whose disease or symptom will benefit from "increasing GLP-1R signaling" or "decreasing GIPR signaling". These subjects are referred to as subjects who "need GLP-1R stimulation therapy" or "need to reduce GIPR stimulation", including non-insulin-dependent diabetes, insulin-dependent diabetes, stroke (GLP-1R see WO 00/16797), myocardial infarction (GLP-1R see WO 98/08531), obesity (GLP-1R see WO 98/19698; GIPR see Furija et al., 2008, *PLoS ONE* 3: e3163; US 2017/0275370 A1), catabolic changes after surgery (GLP-1R see U.S. Pat. No. 6,006,753), functional dyspepsia and irritable bowel syndrome (GLP-1R see WO99/64060), liver steatosis (GIPR see US 2017/0275370A1), non-alcoholic fatty liver disease (GLP-1R see Debra et al., 2016, *Hepatobiliary Surg Nutr* 5:515-518; GIPR see US 2017/0275370 A1), non-alcoholic steatohepatitis (GLP-1 see Armstrong et al., 2013, *BMJ Open* 3: e003995; GIPR see US 2017/0275370 A1), also including subjects at risk of developing non-insulin-dependent diabetes (see WO 00/07617), subjects with impaired glucose tolerance or impaired fasting glucose, subjects whose body weight is about 25% higher than the normal height and weight, and subjects with partial pancreatectomy.

In one embodiment, the biological activity changes of the GIPR antibody or its fusion protein with GLP-1 are detected using a direct cAMP assay, quantifying the function of GIPR antibody or GLP-1 fusion protein in inhibiting GIPR in vitro.

Pharmaceutical Compositions

In one embodiment, a pharmaceutical composition provided herein comprises an GIPR antibody provided herein and one or more pharmaceutically acceptable carriers.

In another embodiment, a pharmaceutical composition provided herein comprises a fusion protein of GIPR antibody and GLP-1 provided herein, and one or more pharmaceutically acceptable carriers.

The term "carrier" as used herein comprises a carrier, a pharmaceutical excipient, or a stabilizer that is harmless by exposing cells or mammals to it at the dosage and concentration used.

Treatment Method

In one embodiment, provided herein is a method of treating, preventing, or ameliorating type 2 diabetes, wherein comprising administration to a subject a therapeutically effective dosage of the GIPR antibody provided herein or a pharmaceutical composition thereof.

In another embodiment, provided herein is a method of treating, preventing, or ameliorating non-alcoholic fatty liver disease, wherein comprising administration to a subject a therapeutically effective dosage of the GIPR antibody provided herein, or a pharmaceutical composition thereof.

In another embodiment, provided herein is a method of treating, preventing, or ameliorating non-alcoholic fatty liver disease, wherein comprising administration to a subject a therapeutically effective dosage of a fusion protein of the GIPR antibody provided herein and GLP-1, or a pharmaceutical composition thereof.

In another embodiment, provided herein is a method of treating, preventing, or ameliorating non-alcoholic steatohepatitis, wherein comprising administration to a subject a therapeutically effective dosage of the GIPR antibody provided herein, or a pharmaceutical composition thereof.

In another embodiment, provided herein is a method of treating, preventing, or ameliorating non-alcoholic steatohepatitis, wherein comprising administration to a subject a therapeutically effective dosage of a fusion protein of the GIPR antibody provided herein and GLP-1, or a pharmaceutical composition thereof.

In another embodiment, provided herein is a method of treating, preventing, or ameliorating type 2 diabetes, wherein comprising administration to a subject a therapeutically effective dosage of the GIPR antibody provided herein, or a pharmaceutical composition thereof.

In another embodiment, provided herein is a method of treating, preventing, or ameliorating type 2 diabetes, wherein comprising administration to a subject a therapeutically effective dosage of a fusion protein of the GIPR antibody and GLP-1 provided herein, or a pharmaceutical combination thereof.

In another embodiment, provided herein is a method of treating, preventing, or ameliorating obesity, wherein comprising administration to a subject a therapeutically effective dosage of the GIPR antibody provided herein, or a pharmaceutical composition thereof.

In a further embodiment, provided herein is a method of treating, preventing, or ameliorating obesity, wherein comprising administration to a subject a therapeutically effective dosage of a fusion protein of the GIPR antibody provided herein and GLP-1, or a pharmaceutical composition thereof.

In any of the uses provided herein, the pharmaceutical composition provided herein is for intravenous or subcutaneous injection.

As used herein, the term "subject" refers to a mammal, including humans, and is used interchangeably with the term "patient."

The term "treatment" comprises alleviation or prevention of at least one symptom or other aspect of a disorder, or reduction of disease severity. A GIPR antibody or fusion protein of GIPR antibody and GLP-1 provided herein needs not to provide a complete cure, or to eradicate every symptom or manifestation of a disease, to be an effective therapeutic agent. As is recognized in the pertinent field, therapeutic agents can reduce the severity of a given disease state, but need not to abolish every manifestation of the disease to be effective. Similarly, a prophylactic agent needs not to prevent the onset of a condition completely in order to be effective. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antibody in an amount and for a time sufficient to induce a sustained improvement over baseline of an indicator that reflects the severity of a particular disorder.

A pharmaceutical composition of a GIPR antibody or fusion protein of GIPR antibody and GLP-1 can be administered by any suitable technique, including, but not limited to, parenterally, topically, or by inhalation. If injected, the pharmaceutical composition can be administered, for example, via an intra-articular, intravenous, intramuscular, intralesional, intraperitoneal or subcutaneous route, by bolus injection or continuous infusion. It is considered, for example, localized administration at the disease or injury site, such as transdermal administration and sustained release of an implant. Delivery by inhalation includes, for example, nasal or oral inhalation, use of a nebulizer, inhalation of an antibody in aerosol form, and the like. Other alternatives include oral preparations, including pills, syrups, or lozenges.

Advantageously, the GIPR antibody or fusion protein of GLP-1 provided herein, is administered in a composition comprising one or more additional components such as a physiologically acceptable carrier, excipient or diluent. The composition additionally comprises one or more physiologically active agents as described below. In many particular embodiments, the composition comprises one, two, three, four, five, or six physiologically active agents in addition to one or more antibodies (e.g., murine antibodies or humanized antibodies) or GLP-1 fusion protein provided herein.

In one embodiment, the pharmaceutical composition comprises a murine antibody or humanized antibody or GLP-1 fusion protein provided herein together with one or more substances selected from the group consisting of a buffer suitable for the antibody at a suitable pH, an antioxidant such as ascorbic acid, a low molecular weight polypeptide (such as those having fewer than 10 amino acids), a protein, an amino acid, a carbohydrate such as dextrin, a chelating agent such as EDTA, glutathione, a stabilizer, and an excipient. In accordance with appropriate industry standards, preservatives can also be added. The composition can be formulated as a lyophilizate using appropriate excipient solutions as diluents. Suitable components are nontoxic to recipients at the dosages and concentrations employed. Further examples of components that can be employed in pharmaceutical formulations are presented in Remington's Pharmaceutical Sciences, 16th Ed. (1980) and 20th Ed. (2000). Mack Publishing Company kits for use by medical practitioners are provided, including one or more antibodies or GLP-1 fusion protein of the invention and a label or other instructions for use in treating any of the conditions discussed herein. In one embodiment, the kit includes a sterile preparation of one or more human antibodies or GLP-1 fusion proteins, which can be in the form of a composition as disclosed above, and can be in one or more vials.

Dosages and the frequency of administration can vary according to such factors as the route of administration, the particular antibody or GLP-1 fusion protein employed, the nature and severity of the disease to be treated, whether the condition is acute or chronic, and the size and general condition of the subject. Appropriate dosages can be determined by procedures known in the pertinent art, e.g. in clinical trials that can involve dose escalation studies.

The antibody or GLP-1 fusion protein provided herein can be administered, for example, once or more than once, e.g., at regular intervals over a period of time. In particular embodiments, the murine antibody or humanized antibody or GLP-1 fusion protein is administered once over a period of at least a month or longer, e.g., for one, two, or three months or even indefinitely. For treating chronic conditions, long-term treatment is generally most effective. However, for treating acute conditions, administration for shorter periods, e.g., from one to six weeks, can be sufficient. In general, the humanized antibody is administered until the patient manifests a medically relevant degree of improvement over baseline for the chosen indicator or indicators.

An example of the treatment regimen provided herein includes subcutaneous injection of the antibody or GLP-1 fusion protein at an appropriate dose once a week or longer to treat symptoms caused by type 2 diabetes, obesity, or non-alcoholic steatohepatitis. The antibody or GLP-1 fusion protein can be administered weekly or monthly until the desired result is achieved, for example, the patient's symptoms subside. Treatment can be renewed as needed, or, alternatively, a maintenance dose can be given.

The patient's blood glucose concentration and body weight can be monitored before, during, and/or after treatment with the antibody or GLP-1 fusion protein, such as the human antibody or GLP-1 fusion protein, to detect any changes in their pressure. For certain conditions, changes in blood glucose can vary with factors such as disease progression. The blood glucose concentration can be determined using known techniques.

Specific embodiments of the methods and compositions herein involve the use of, for example, the antibody or GLP-1 fusion protein and one or more GIP antagonists, two or more antibodies or GLP-1 fusion proteins provided herein, or the antibody or GLP-1 fusion protein provided herein and one or more other GIP antagonists. In a further embodiment, the antibody or GLP-1 fusion protein is administered alone or in combination with other agents used to treat symptoms that are painful for the patient. Examples of these agents include protein and non-protein drugs. When multiple drugs are administered in combination, the dosage should be adjusted accordingly as is well known in the art. "Combined administration" combination therapy is not limited to simultaneous administration, but also includes treatment regimens in which the antigen and protein are administered at least once during the course of administration involving the administration of at least one other therapeutic agent to the patient.

On the other hand, provided herein is a method for preparing a medicament for treating type 2 diabetes, obesity and non-alcoholic steatohepatitis and related disorders, which comprises a mixture of the antibody or GLP-1 fusion protein provided herein and a pharmaceutically acceptable excipient for the treatment of the related diseases of the above diseases. The pharmaceutical preparation method is as described above.

Further provided herein are compositions, kits, and methods related to antibodies or GLP-1 fusion proteins that can specifically bind to human GIPR. Nucleic acid molecules and derivatives and fragments thereof are also provided, wherein comprising polynucleotides encoding all or part of a polypeptide that binds to GIPR, for example, nucleic acid encoding all or part of an GIPR antibody, antibody fragment, antibody derivative, or GLP-1 fusion protein. Further provided herein are vectors and plasmids containing such nucleic acids and cells and cell lines containing such nucleic acids and/or vectors and plasmids. Methods provided herein comprise, for example, methods for preparing, identifying, or isolating antibodies or GLP-1 fusion proteins that bind to human GIPR, a method to determine whether the antibody or GLP-1 fusion protein binds to GIPR, and a method of administering the antibody or GLP-1 fusion protein that binds to GIPR into an animal model.

The technical solutions described herein will be further understood by the following examples.

If not specified, the starting materials and equipment described herein are commercially available or commonly used in the art. The methods in the following examples, unless otherwise specified, are all conventional methods in the art. 1: Preparation of antigen for immunization CHO-DHFR-cells were seeded into a 6-well plate. After 24 hours (hr), the cells were transfected with a pTM15 plasmid containing hGIPR (human GIPR) gene (see SEQ ID NO: 114 for the nucleotide sequence, and SEQ ID NO: 113 for the amino acid sequence). The transfection was carried out using Lipofectamine 2000 (Invitrogen) following the manufacturer's recommended protocol. 48 hr after transfection, the medium was replaced with a complete medium containing 300 μg/mL hygromycin, and the medium was changed every 3 days (d). For about two weeks of culturing, the stable clones were visible. The dispersed cell colonies were detached from the plate and continually subcultured until they reached 100% confluence. The constructed stable cell lines were analyzed by FACS, using a monoclonal antibody (Life Technologies) against V5 tag to verify positive clones after pressure selection. A large amount of cell-surface hGIPR expression was detected on the selected CHO-DHFR-hGIPR cells. Finally, three high hGIPR expression stable cell lines were identified by subcloning and further verification. These cell lines were used to produce immunogens for antibody preparation (see Example 2). In addition, in some embodiments, the fusion protein of the extracellular domain of hGIPR and hIgG Fc can also be used as an immunogen for antibody preparation. The preparation method is the following: subcloning the fusion protein gene of hGIPR extracellular domain, hIgG Fc and the peptide linker (Linker) into the pTM5 plasmid. Cell supernatant was generated by mass transient expression using suspended HEK293 cells, and then the hGIPR extracellular domain fusion protein was obtained by affinity chromatography purification.

2: Preparation of Antibodies

Antibodies against hGIPR can be produced using an immunogen including any of the following. For example, in certain embodiments, the whole cells expressing hGIPR are used as immunogens to produce antibodies against hGIPR. Furthermore, in certain embodiments, fusion proteins comprising N-terminal extracellular domain of hGIPR and hFc are used as immunogens to generate antibodies against hGIPR. The immunogen and aluminum hydroxide adjuvant were mixed, and BALB/c mice (6-8 weeks) was subcutaneously injected and boosted once a week. After 6-round of immunization in total, blood samples were collected from the tail veins and serum was separated by centrifugation, then the serum titer was analyzed by FACS. After the highest titers were achieved, the mice were sacrificed and their spleen cells were harvested under aseptic conditions. SP2/0 cells in the logarithmic growth phase were collected, centrifuged, and the cell pellets were resuspended with serum-free culture medium, then centrifuged, resuspended for a second time and counted. Spleen cells and SP2/0 cells were mixed at ratio of SP2/0 cells: spleen cells≥1:1, followed by 3-round of washing-centrifugation. After the pellets from the last centrifugation were flicked, 1 mL of pre-warmed PEG-1500 was added dropwise, pipette-mixed for 1 min, 30 mL of the pre-warmed serum-free medium was added slowly to terminate the PEG fusion. The cell pellets were resuspended in the fusion culture medium. Spleen cells and feeder layer cells in 100 μL were plated into each well of 96-well plates. Fused hybridoma cells and feeder layer cells were co-cultured in 96-well plates with HAT (sarcine, amethopterin and thymidine) selection to remove non-fused cells. After 10 days, the supernatants of the hybridoma cells in the culture plates were collected for ELISA analysis.

3: ELISA Screening of Antibodies

CHO-DHFR-hGIPR cells over-expressing hGIPR and CHO-DHFR-blank cells were separately transferred into a 96-well plate and allowed to reach 90% confluence. The supernatant of the culture medium was removed and attached cells were washed twice with PBS, and 100% methanol was added to fix the cells at 4° C. Then 100 μL of freshly made 0.6% $H_2O_2$—PBS was added, and after incubation at room temperature for 20 minutes (min), the cells were washed twice with PBS. After blocking with 1% BSA solution (dissolved in PBS), the hybridoma supernatant was added and incubated for 90 min at 4° C. After several washes, 100 μL of the diluted goat anti-mouse Fc-HRP secondary antibody (Sigma-Aldrich) was added into each well and incubated at 37° C. for 30 min. After washing five times, 100 μL of TMB chromogenic substrate was added and incubated at 37° C. for 15 min, and then 50 μL of 2M $H_2SO_4$ was added to terminate the reaction before reading at 450 nm. Furthermore, in certain embodiments, a fusion protein of the N-terminal extracellular domain of hGIPR and hFc is used as the coating antigen. After blocking with 1% BSA (dissolved in PBS), the supernatant of hybridoma cells was added and incubated at 4° C. for 90 min. The subsequent steps are the same as the above ELISA method to screen anti-hGIPR monoclonal antibodies. The positive control is the serum of immunized mice; the negative control is the cell culture medium. After preliminary screening by ELISA, several positive hybridoma cell lines secreting hGIPR antibodies were obtained. These hybridoma cell lines secreting hGIPR antibodies were selected and subcloned by limiting dilution. Finally, the supernatant of positive hybridoma cells was verified by FACS analysis (referring Example 10).

4: Cloning and Subcloning of Antibody Genes

Hybridoma cells secreting antibodies were collected. Hybridoma mRNA was extracted according to the manufacturer protocol of QIAGEN mRNA extraction kit. Then the extracted mRNA was reverse-transcribed into cDNA. The reverse transcription primers were specific primers for murine light and heavy chain constant regions, specifically the heavy chain reverse transcription primer was (5'-TTTGGRGGGAAGATGAAGAC-3') (SEQ ID NO: 137), the light chain reverse transcription primers were (5'-TTAACACTCTCCCCTGTTGAA-3') (SEQ ID NO: 138) and (5'-TTAACACTCATTCCTGTTGAA-3') (SEQ ID NO: 139). RT-PCR reaction conditions were listed as following: 25° C. for 5 min, 50° C. for 60 min, and 70° C. for 15 min. Reversely transcribed cDNA was diluted with 0.1 mM TE to 500 μL, added into the ultrafiltration centrifuge tube (Amicon Ultra-0.5) and centrifuged at 2,000 g for 10 min. The filtrate was removed, 500 μL of 0.1 mM TE were added and centrifuged at 2,000 g for 10 min. The filtrate was removed and the preparation tube was placed in inversion to the new centrifugal tube, and centrifuged at 2,000 g for 10 min to obtain the purified cDNA. Purified cDNA (10 μL) was taken as a template, followed by addition of 4 μL 5×tailing buffer (Promega), 4 μL dATP (1 mM) and 10 U terminal transferase (Promega), mixing uniformly, and incubation at 37° C. for 5 min and then at 65° C. for 5 min. The Poly A tail cDNA was used as a template and PCR was performed to amplify light and heavy chain variable region genes of antibodies. Upstream primers were all oligo dT, with heavy chain downstream primers being (5'-TGGACAGGGATCCAGAGTTCC-3') (SEQ ID NO: 140) and (5'-TGGACAGGGCTCCATAGTTCC-3') (SEQ ID NO: 141), and light chain downstream primer being (5'-ACTCGTCCTTGGTCAACGTG-3') (SEQ ID NO: 142). The PCR reaction conditions were: 95° C. for 5 min; 95° C. for 30 seconds(s), 56° C. for 30 s, 72° C. for 1 min, 40 cycles; and 72° C. for 7 min. The PCR products were connected to the PMD 18-T vector (Takara Bio) for sequencing. PCR primers were designed based on the DNA sequences of the antibodies, thus the complete light chain, heavy chain signal peptides and variable domains and mouse IgG1 constant region were ligated into expression vector pTM5.

5: Antibody Humanization and Optimization

First of all, the sequences of light and heavy chain variable regions of the mouse antibodies were used as input in a search with NCBI online antibody variable region sequence alignment tool (Ig Blast) to find the germline gene sequences of a human antibody (Ig Germline Gene sequence) homologous to the mouse antibodies variable region sequence for humanization, and the human gene sequence with highest homology excluding the CDR sequences was used as a template for CDR grafting to obtain humanized antibody variable region sequences. The humanized antibody light and heavy chain variable regions genes were synthesized and combined with the human IgG2 or IgG4 constant region sequence to obtain full-length recombinant humanized antibody sequences. The recombinant antibodies were expressed according to Example 8, and their affinities to GIPR was analyzed by FACS as described in Example 10 to select the antibody with the best affinity. The variable region sequences of the humanized antibody were engineered by site-specific mutagenesis to further improve its affinity for GIPR.

6: Subcloning of Genes of Humanized hGIPR Antibodies

The heavy and light chain variable region gene sequences of optimized humanized antibodies were synthesized by outsourcing. During the process, two restriction sites, NheI at the 5'-end and SalI at the 3'-end, were introduced into the heavy chain variable region sequence. The complete heavy chain variable region was ligated with a heavy chain constant region in an expression vector of pTM5. Similarly, by introducing NheI at the 5'-end and BsiwI at the 3'-end, the light chain variable region was ligated with a light chain constant region in the expression vector of pTM5.

7: Construct of the Fusion Protein of Humanized hGIPR Antibody and GLP-1

Optimized humanized antibody was fused with GLP-1 or its derivative sequences, via the N-terminus or C-terminus of the light chain to form a GLP-1 fusion protein, and the sequences of the two are connected by the peptide linker sequence (Linker) as a bridge. Nucleotide sequence of the signal peptide-GLP-1-Linker is synthesized by Genscript Biotechnology Co., Ltd. Using the synthetic gene as the template, the sequence of the part "signal peptide-GLP1-Linker" was amplified using PCR. In addition, using the nucleotide sequence of the humanized antibody as template, the sequence of the antibody of the fusion protein sequence is amplified. Then through overlapping PCR, the part "signal peptide-GLP-1-peptide linker" of the nucleic acid sequence of the fusion protein is connected with the antibody part, introducing two restriction enzyme sites NheI and Not1 to both ends of the primers, and thus complete fusion protein sequence and the expression vector pTM5 are linked together.

8: Transient Expression of hGIPR Antibody and GLP-1 Fusion Protein

HEK293 or CHO suspension cells ($5\times10^5$/mL) was inoculated into a shaker flask. After rotating at 37° C. for 24 hr, the cells density reached $1\times10^6$/mL and were used for transfection. Polyethylenimine (PEI) is used as a transfection reagent, and it is mixed with DNA. The mixture of PEI/DNA was added into the cell culture after 15 minutes of incubation. After receiving the mixture of PEI/DNA, the cells were continuously cultured at 37° C., 5% $CO_2$ for 24 hr. Then tryptone was added into the cell culture as a supplement for expression. Finally, after the protein expression was completed (more than 96 hr), the cell supernatant was collected for antibody purification.

9: Purification and Separation of hGIPR Antibody and GLP-1 Fusion Protein

Cells and cellular debris were removed from the culture after centrifugation (8000 rpm), and the supernatant was filtered through a 0.22 μm filter. The clarified supernatant is used for purification. The purification process was completed through chromatograph. The supernatant first flows through the protein A/G affinity column, during which the antibody within bounded to the A/G proteins and remained in the column. The antibodies were then eluted from the chromatography column using an elution buffer with a low pH (less than or equal to 3.0). The low pH eluent was neutralized immediately with 1M Tris-HCl. The purified antibody was then dialyzed against PBS or other buffer systems.

10: FACS to Verify the Binding Activity of Functional hGIPR Antibodies

Figure 2:
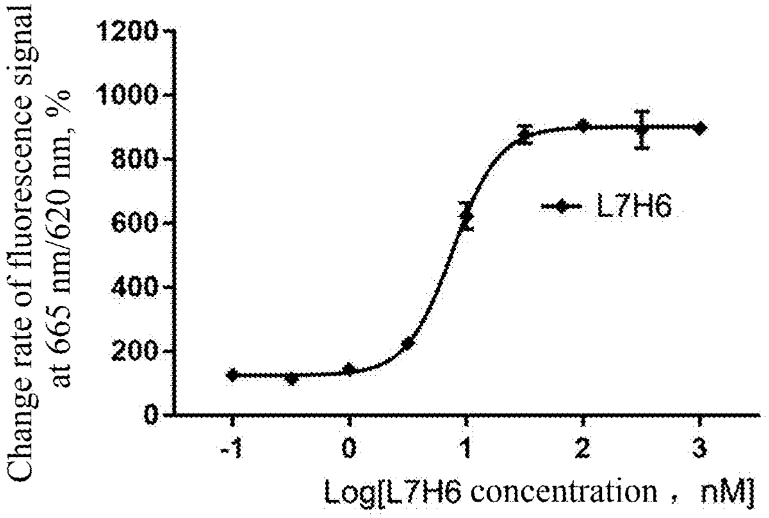
FIG. 2 shows the concentration inhibition curve of hGIPR antibody L7H6 (comprising SEQ ID NO: 67 and SEQ ID NO: 77) antagonizing GIP activation of hGIPR signaling pathway, as determined by direct cAMP assay ($IC_{50}$=7.6 nM, $R^2$=0.99).
Figure 3:
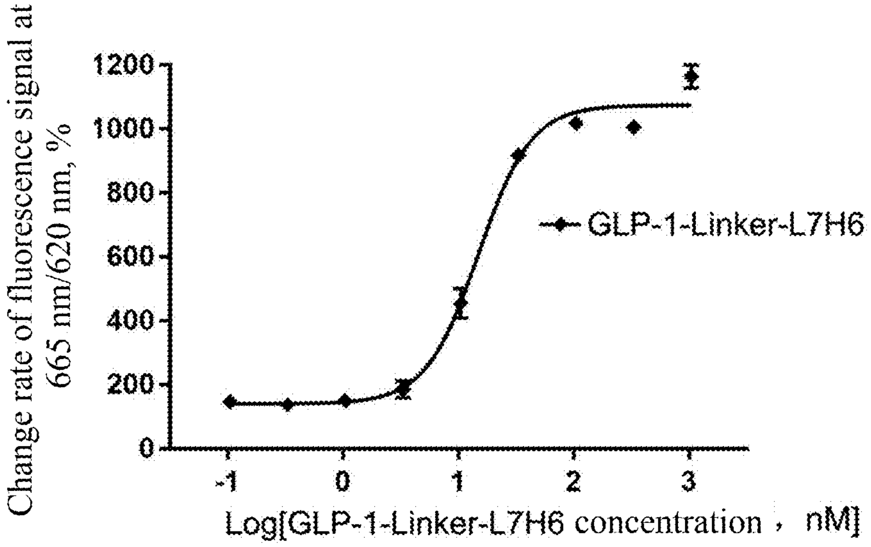
FIG. 3 shows the inhibition curve of GIPR antibody/GLP-1 fusion protein GLP-1-Linker-L7H6 (comprising SEQ ID NO: 67, SEQ ID NO: 77, SEQ ID NO: 106, SEQ ID NO: 111) antagonizing GIP activation of the hGIPR signal pathway, as determined by direct cAMP assay ($IC_{50}$=14.9 nM, $R^2$=0.99).

PBS containing 10 mM EDTA was used to detach the CHO-DHFR-hGIPR cells and $10^5$ cells/tube was distributed into 1.5 mL EP tubes, and the supernatant was removed after centrifugation. The negative control sample was resuspended with a loading buffer (PBS, 2% FBS). For the positive control, 200 μL GIPR antibody solution of specific concentration was added to the cells and incubated at room temperature; after incubation, the cells were then centrifuged at 1500 rpm to remove the supernatant, washed with a FACS loading buffer and centrifuged again. The cells were resuspended with addition (200 μL/well) of a FITC labeled goat anti-mouse fluorescent antibody or PE labeled goat anti-human fluorescent antibody at 1:50 dilution and incubated at room temperature for 30 min in the dark. The supernatant was removed after centrifugation, and cells were washed with FACS loading buffer, centrifuged again and resuspended with the loading buffer for FACS analysis. The recombinant anti-hGIPR functional antibody specifically binds to GIPR-expressing CHO-DHFR-GIPR cells. In the experimental results shown in FIG. 1, grey peak and dotted line peak were negative controls; the solid line peak, corresponding to 1 μM of antibody L10H8, shows a significant right shift to prove the specific binding of L10H8 and CHO-DHFR-GIPR. 11: CAMP assay test of hGIPR antibody or hGIPR antibody/GLP-1 fusion protein for its in vitro antagonistic activity of GIPR CHO-DHFR cells stably expressing human GIPR were seeded with 30,000 cells per well into 96-well cell culture plates, placed in a 37° C., 5% $CO_2$ incubator overnight. The next day the supernatant was removed and the hybridoma supernatant or serially diluted antibody of 45 μL/well was added. The cells were left at room temperature for 30 min, then GIP peptide were added (Phoenix Pharmaceuticals, 50 μM) at 45 μL/well. Then the 96-well plate was placed in a 37° C., 5% $CO_2$ incubator for 30 minutes, 10 μL/well of 10% Triton X-100 were added to lyse the cells at room temperature, and lysate was mixed evenly with the pipette. The CAMP kit (CisBio) was used to detect the CAMP produced in the experiment. The above 10 μL/well cell lysate were transferred into a white 384-well plate, 5 μL/well of 1:20 diluted cAMP-d2 was added, and finally 5 L/well of 1:20 diluted Anti-CAMP-Eu3±cryptate was added, and the plate was incubated at room temperature for 1 hr. The time-resolved fluorescence 665 nm/620 nm signal ratio was read on the Envision 2103 microplate reader, and then Prism5.0 was used to calculate the $IC_{50}$ value. FIG. 2 shows that L7H6 antagonizes GIPR with $IC_{50}$=7.6 nM. FIG. 3 shows that GLP-1-Linker-L7H6 antagonizes GIPR with $IC_{50}$=14.9 nM.

Figure 4:
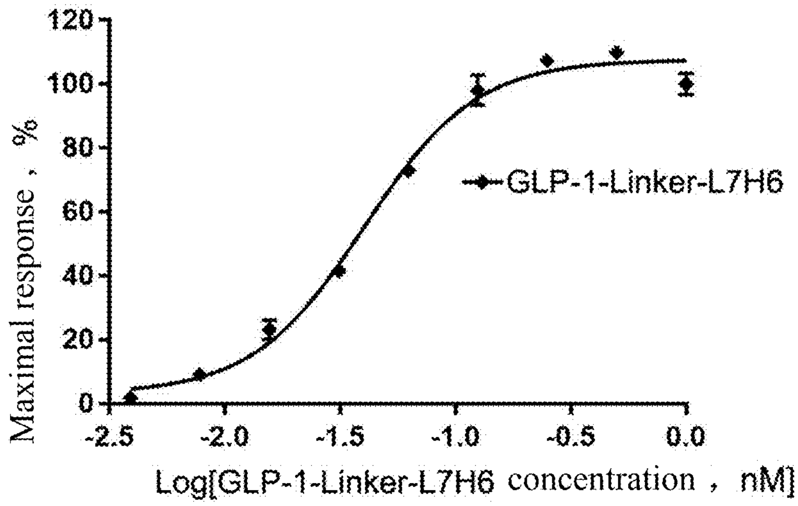
FIG. 4 shows the activation curve of the reporter gene experiment to test the GIPR antibody/GLP-1 fusion protein GLP-1-Linker-L7H6 to activate the hGLP-1R signaling pathway, as determined by reporter gene assay ($EC_{50}$=0.04 nM, $R^2$=0.99).

12: Reporter Gene Assay Test of hGIPR Antibody/GLP-1 Fusion Protein for its In Vitro Activation of GLP-1R CHO-DHFR-cells co-expressing hGLPIR and CRE-Luciferase were seeded into a 96-well cell culture plate with 20000 cells per well, and cultured at 37° C. overnight. The next day the culture supernatant was removed. The cells were washed twice with serum free medium and residual liquid was removed as well. Then add 100 μL of serum free medium containing serially diluted antibodies or GLP-1 and incubate at 37° C. for 4 hr. After the stimulation, 100 μL of Bright Glo chemiluminescence substrate (Promega) was added. Finally, the cell lysates were transferred into a white 96-well plate, and the relative luminous intensity was recorded in SpectraMax L microplate reader (Molecular Devices). FIG. 4 shows that GLP-1-Linker-L7H6 activates hGLP-1R with $EC_{50}$=0.04 nM.

13: In Vivo Efficacy Study of hGIPR Antibody in High-Fat Diet-Induced C57BL/6 Obese Mice 60% high-fat diet induced C57BL/6 mice obesity model (DIO mice) was established. After the mice were purchased and fed on a normal diet for a week, randomly select a certain number of mice as the normal control group to give ordinary mice diet, and the remaining animals were fed with high-fat diet. All animals were continuously fed for 8 weeks, and body weight and food intake were assessed once a week. Subsequently, the mice fed with high-fat diet were randomly divided into the L10H8 group (10 mg/kg) and the model group according to their body weight. The drugs were injected subcutaneously every two days for 6 weeks. The normal control group is not administered, and the model group is given the same amount of blank formulation. The data of body weight, food intake and behavioral observation were collected during the experiment period. At the last day of the experiment, after 12 hr fast (free access to water), the animal's orbital blood was collected to separate serum and then euthanized, the liver was dissected and weighed, and the liver morphology was observed. ALT, AST, GLU, TC and TG in sera, and TG in liver were tested (see results in FIG. 5 and Table 3).

TABLE 3

Biochemical Test Results of Each Group after Drug Administration

| Analytes | Normal group | L10H8 group | Model group |
|---|---|---|---|
| ALT (IU/L) | 37.88 ± 5.08** | 92.08 ± 30.05** | 158.37 ± 40.50 |
| AST (IU/L) | 136.20 ± 24.21** | 157.20 ± 27.09 | 184.82 ± 35.49 |
| GLU (mmol/L) | 8.38 ± 1.15** | 11.67 ± 2.04 | 10.91 ± 1.87 |
| TC (mmol/L) | 3.29 ± 0.25** | 6.30 ± 0.31 | 6.62 ± 1.00 |
| TG (mmol/L) | 0.99 ± 0.07** | 1.41 ± 0.13* | 1.21 ± 0.11 |
| Liver TG (mmol/L) | 26.83 ± 16.96** | 88.23 ± 9.61* | 159.08 ± 67.87 |
| Liver index (g/100 g) | 3.65 ± 0.23 | 3.76 ± 0.44* | 4.56 ± 1.28 |

Note:
Means ± SEM, compared with the model group,
*P < 0.05,
**P < 0.01; Liver index = liver weight/body weight *100.

Figure 5:
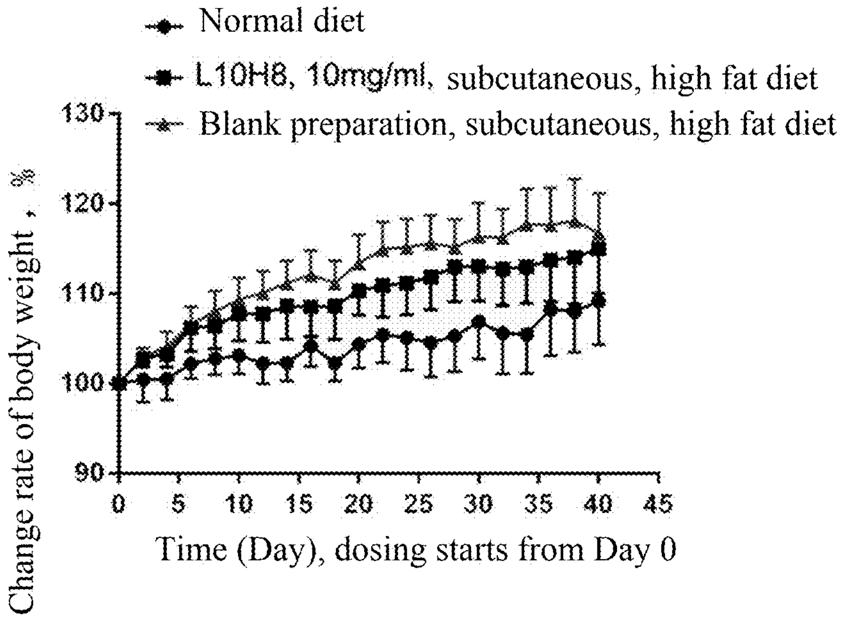
FIG. 5 shows the time curve of body weight change rate in different groups of C57BL/6 obese mice induced by high fat diet during the efficacy test period.

After 6 weeks of administration of the L10H8, the weight gain of the L10H8 group was only slightly lower than that of the model group, but the liver weight was significantly lower than that of the model group, and close to that of the normal control group. The liver TG of the L10H8 group was significantly lower than that of the model group, and the serum TG was significantly higher than that of the model group. These results show that L10H8 significantly slows the absorption and accumulation of liver fat. FIG. 5 shows the percentage of body weight change of each group. Table 3 summarizes the liver analytical data in each group after receiving L10H8 antibody for 6 weeks.

Figure 6:
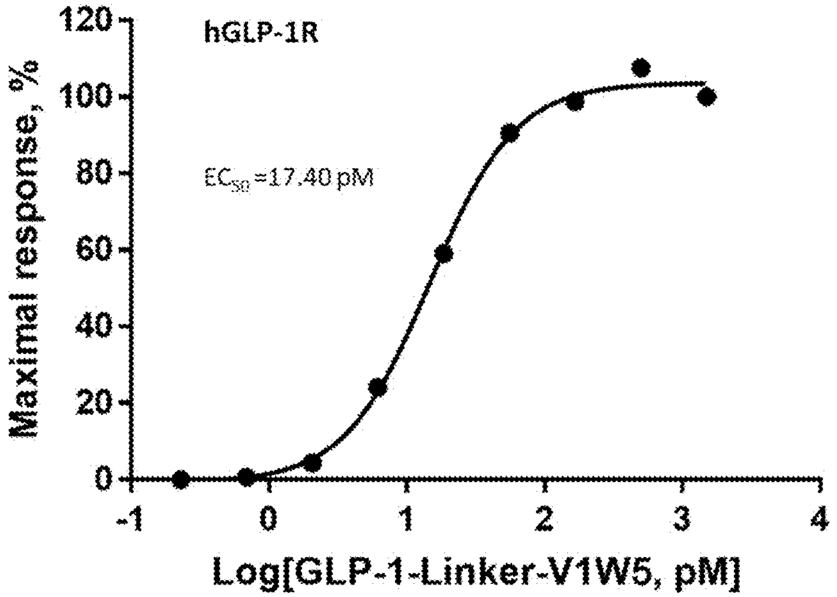
FIG. 6 shows the activation curve of the reporter gene experiment to test the GIPR antibody/GLP-1 fusion protein GLP-1-Linker-V1W5 (comprising SEQ ID NO: 106, SEQ ID NO:111, SEQ ID NO: 125 and SEQ ID NO: 131) to activate human GLP-1 receptor (hGLP-1R) signaling pathway, as determined by reporter gene assay ($EC_{50}$=17.40 μM, $R^2$=0.99).

14. Reporter Gene Assay Test of hGIPR Antibody/GLP-1 Fusion Protein GLP-1-Linker-V1W5 for its In Vitro Activation of GLP-1R CHO-DHFR-cells co-expressing hGLP-1R-CRE-Luciferase were seeded into a 96-well cell culture plate with 20000 cells per well, and cultured at 37° C. overnight. The next day the culture supernatant was removed. The cells were washed twice with serum free medium and residual liquid was removed as well. Then add 100 μL of serum free medium containing serially diluted antibodies or GLP-1 and incubate at 37° C. for 4 hr. After the stimulation, 100 μL of Bright Glo chemiluminescence substrate (Promega) was added. Finally, the cell lysates were transferred into a white 96-well plate, and the relative luminous intensity was recorded in SpectraMax L microplate reader (Molecular Devices). FIG. 6 shows that GLP-1-Linker-V1W5 activates hGLP-1R with $EC_{50}$=17.40 μM.

Figure 7:
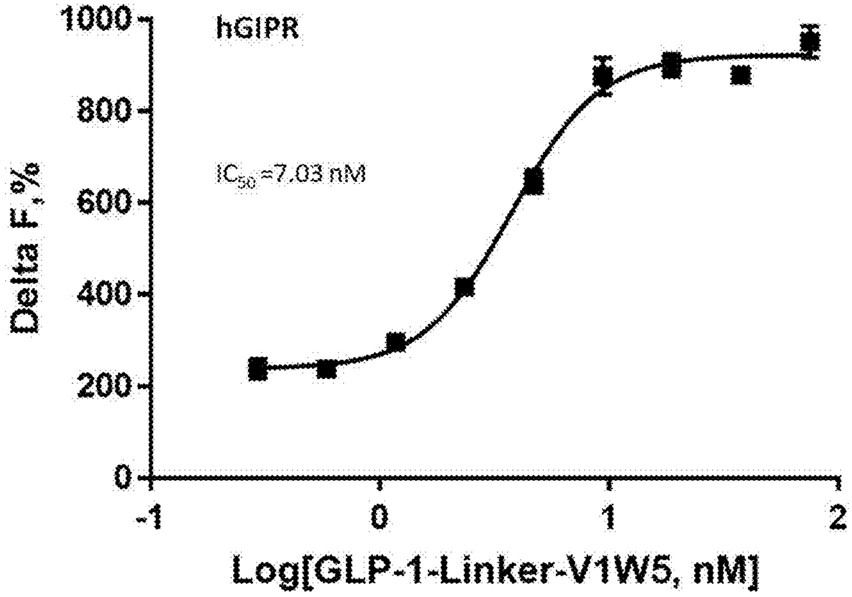
FIG. 7 shows the inhibition curve of hGIPR antibody GLP-1-Linker-V1W5 antagonizing GIP activation of hGIPR signaling pathway, as determined by direct CAMP assay (IC50=7.03 nM, $R^2$=0.99).
Figure 8:
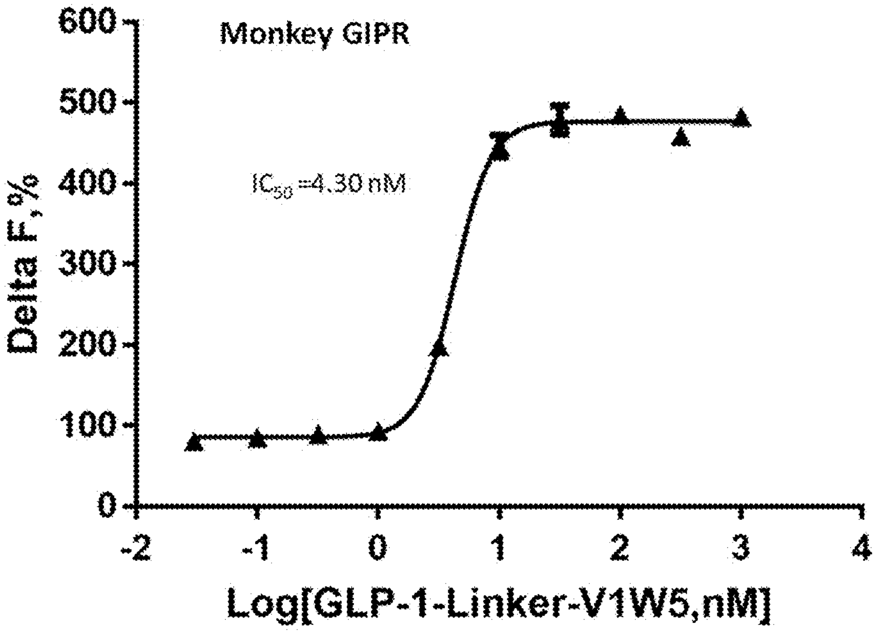
FIG. 8 shows the inhibition curve of human GIP receptor (hGIPR) antibody/GLP-1 fusion protein GLP-1-Linker-V1W5 antagonizing GIP activation of monkey GIPR receptor (maGIPR) signaling pathway, as determined by direct cAMP assay (IC50=4.30 nM, $R^2$=0.99).

15. CAMP Assay Test of hGIPR Antibody or hGIPR Antibody/GLP-1 Fusion Protein GLP-1-Linker-V1W5 for its In Vitro Antagonistic Activity of GIPR CHO-DHFR cells stably expressing human GIPR were seeded with 30,000 cells per well into 96-well cell culture plates, placed in a 37° C., 5% $CO_2$ incubator overnight. The next day the supernatant was removed and the hybridoma supernatant or serially diluted antibody of 45 μL/well was added. The cells were left at room temperature for 30 min, then GIP peptide were added (Phoenix Pharmaceuticals, 50 μM) at 45 μL/well. Then the 96-well plate was placed in a 37° C., 5% $CO_2$ incubator for 30 minutes, 10 μL/well of 10% Triton X-100 were added to lyse the cells at room temperature, and lysate was mixed evenly with the pipette. The CAMP kit (CisBio) was used to detect the CAMP produced in the experiment. The above 10 μL/well cell lysate were transferred into a white 384-well plate, 5 μL/well of 1:20 diluted cAMP-d2 was added, and finally 5 μL/well of 1:20 diluted Anti-CAMP-Eu3±cryptate was added, and the plate was incubated at room temperature for 1 hr. The time-resolved fluorescence 665 nm/620 nm signal ratio was read on the Envision 2103 microplate reader, and then Prism5.0 was used to calculate the $IC_{50}$ value. FIG. 7 shows that GLP-1-Linker-V1W5 antagonizes human GIP receptor (hGIPR) with $IC_{50}$=7.03 nM. FIG. 8 shows that GLP-1-Linker-V1W5 antagonizes monkey GIP receptor (maGIPR) with $IC_{50}$=4.30 nM.

16: Pharmacokinetic Study of GIPR Antibody/GLP-1 Fusion Protein in Cynomolgus Monkeys A total of 6 cynomolgus monkeys (3 male and 3 female) received a single subcutaneous injection of GLP-1/hGIPR antibody fusion protein at 2 mg/kg dose, and 0.6 mL whole blood sample was collected each at pre-administration (0 min), post-administration 2 hr, 4 hr, 8 hr, 12 hr, 24 hr, 2 d, 4 d, 6 d, 8 d, 10 d, 12 d, 18 d, 28 d via the forelimb vein at the body side same to the administration site and placed in a centrifuge tube on ice, after natural coagulation, the blood samples were then centrifuged to separate the sera and stored at a low temperature (−80° C.) until use. The GLP-1 part and hGIPR antibody part of GLP-1/hGIPR antibody fusion protein in the serum samples were quantified separately by ELISA, and the half-lives of both in the cynomolgus monkey was determined through software analysis.

17: Pharmacokinetic Study of GIPR Antibody/GLP-1 Fusion Protein in Rhesus Monkeys A total of 9 male healthy rhesus monkeys received a single subcutaneous injection of hGIPR antibody/GLP-1 fusion protein (GLP-1-Linker-V1W4, GLP-1-Linker-V1W5, or GLP-1-Linker-V1W6) at 4 mg/kg, 3 animals per group, and 0.6 mL whole blood sample was collected via the forelimb vein at pre-administration (0 min) and 2 hr, 4 hr, 8 hr, 12 hr, 24 hr, 2 d, 4 d, 6 d, 8 d, 10 d, 12 d, 16 d, 20 d, 24 d, 30 d, 36 d, 42 d, 50 d, 60 d post administration, and placed in a centrifuge containing 8 μl DDP-IV inhibitor on ice, after natural coagulation, the blood samples were then centrifuged to separate the sera and stored at a low temperature (−80° C.) until use. The hGIPR antibody part and GLP-1 part of the GLP-1/hGIPR antibody fusion protein in the serum samples were quantified separately by ELISA, and the half-lives of both in the rhesus monkey was determined through software analysis.

Figure 9:
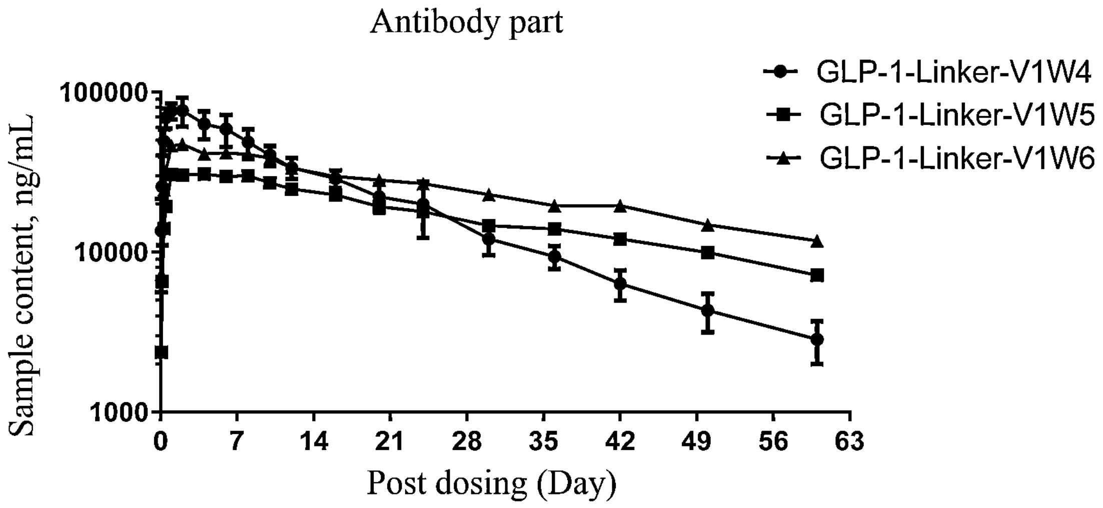
FIG. 9 shows the pharmacokinetic (PK) time curve of the antibody part of the hGIPR antibody/GLP-1 fusion protein in *Rhesus macaque* during the pharmacokinetic study period.
Figure 10:
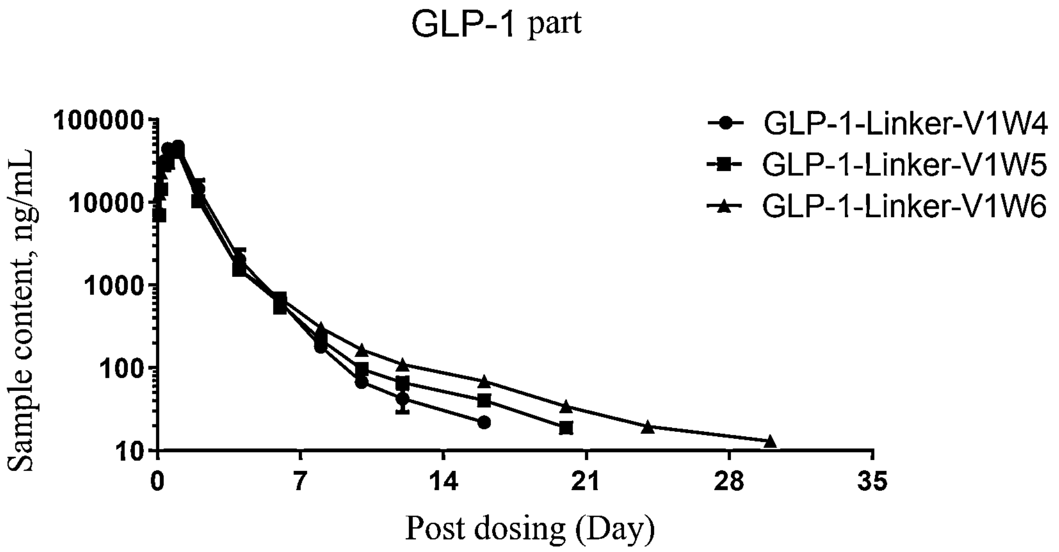
FIG. 10 shows the pharmacokinetic (PK) time curve of the GLP-1 part of the hGIPR antibody/GLP-1 fusion protein in *Rhesus macaque* during the pharmacokinetic study period.

The PK results showed that the $T_{1/2}$ of the antibody part of the three GLP-1/hGIPR antibody fusion proteins described above was approximately 360, 679 and 614 hours respectively, and the $T_{1/2}$ of the GLP-1 part was approximately 87, 82 and 97 hours respectively. The PK curves and parameters of the monkeys in different groups are shown in FIG. 9, FIG. 10 and Table 4.

TABLE 4

PK Parameters of Monkeys in Different Groups

| | | | GLP-1-Linker-V1W4 | GLP-1-Linker-V1W5 | GLP-1-Linker-V1W6 |
|---|---|---|---|---|---|
| Antibody Part | $T_{1/2}$ | Hour | 360 ± 65 | 679 ± 87 | 614 ± 83 |
| | $T_{max}$ | Hour | 12-48 | 24-96 | 24-48 |
| | $C_{max}$ | ng/mL | 82416 ± 11141 | 32270 ± 1097 | 49615 ± 8410 |
| GLP-1 Part | $T_{1/2}$ | Hour | 87 ± 0 | 82 ± 5 | 97 ± 18 |
| | $T_{max}$ | Hour | 12-24 | 24 | 12-24 |
| | $C_{max}$ | ng/mL | 47634 ± 5853 | 41440 ± 1071 | 42251 ± 14729 |

18: In Vivo Efficacy Study of hGIPR Antibody/GLP-1 Fusion Protein in Obese Cynomolgus Monkeys Induced by High-Fat Diet to Evaluate the Efficacy of hGIPR Antibody/GLP-1 Fusion Protein in Primates The obese cynomolgus monkey model (DIO cynomolgus monkey) was established by 60% high-fat diet induction, and then used to evaluate the in vivo efficacy of GLP-1-Linker-L7H6 via subcutaneous administration. The high-fat diet induced monkeys were randomly divided into the GLP-1-Linker-L7H6 (10 mg/kg) group and the model group according to their body weight. The drug was injected subcutaneously every two days for a total of 8 weeks, and the model group was given equal volume of blank formulation. The data of body weight, food intake and behavioral observation were collected during the experiment period. After the experiment was completed, the animals were euthanized, the liver was dissected and weighed, and the liver morphology was observed. ALT, AST, GLU, TC and TG in sera, and TC and TG in liver were tested.

Figure 11:
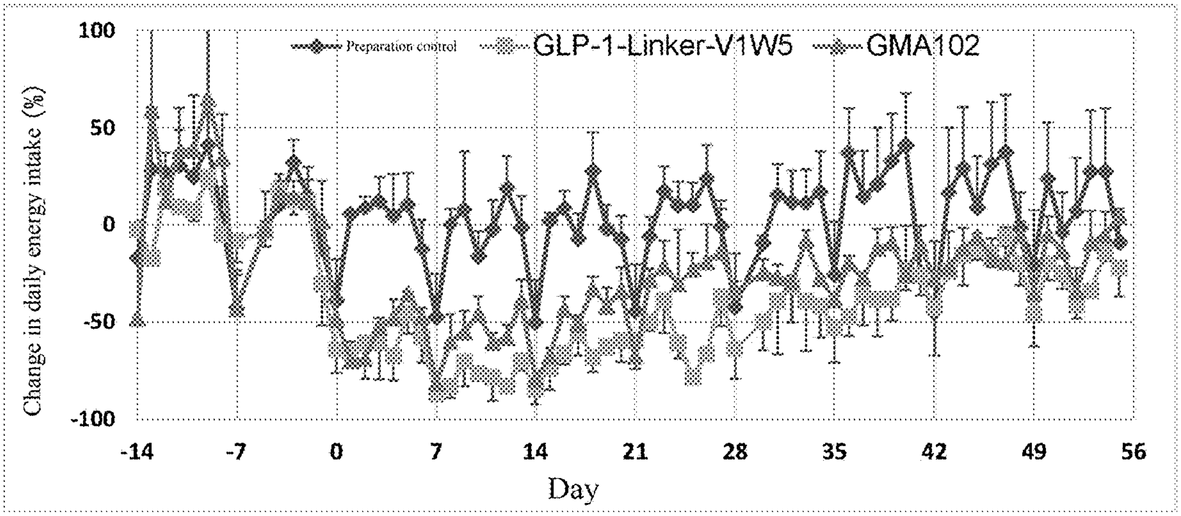
FIG. 11 shows the time curve of the effect of hGIPR antibody/GLP-1 fusion protein on food intake change during the efficacy study period in obese cynomolgus macaque induced by high fat diet.
Figure 12:
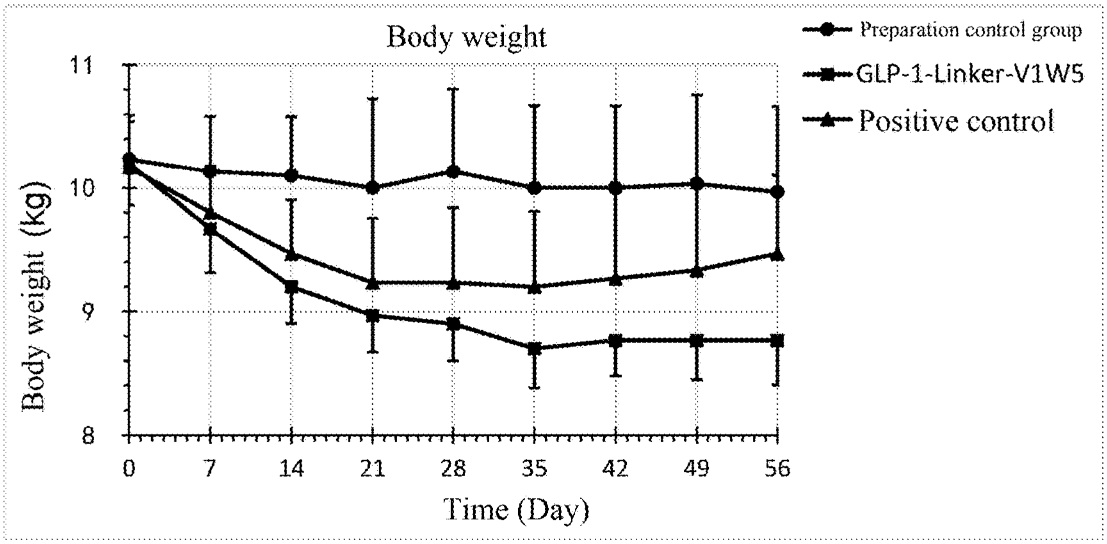
FIG. 12 shows the time curve of the effect of hGIPR antibody/GLP-1 fusion protein on body weight change during the efficacy study period in obese cynomolgus macaque induced by high fat diet.
Figure 13:
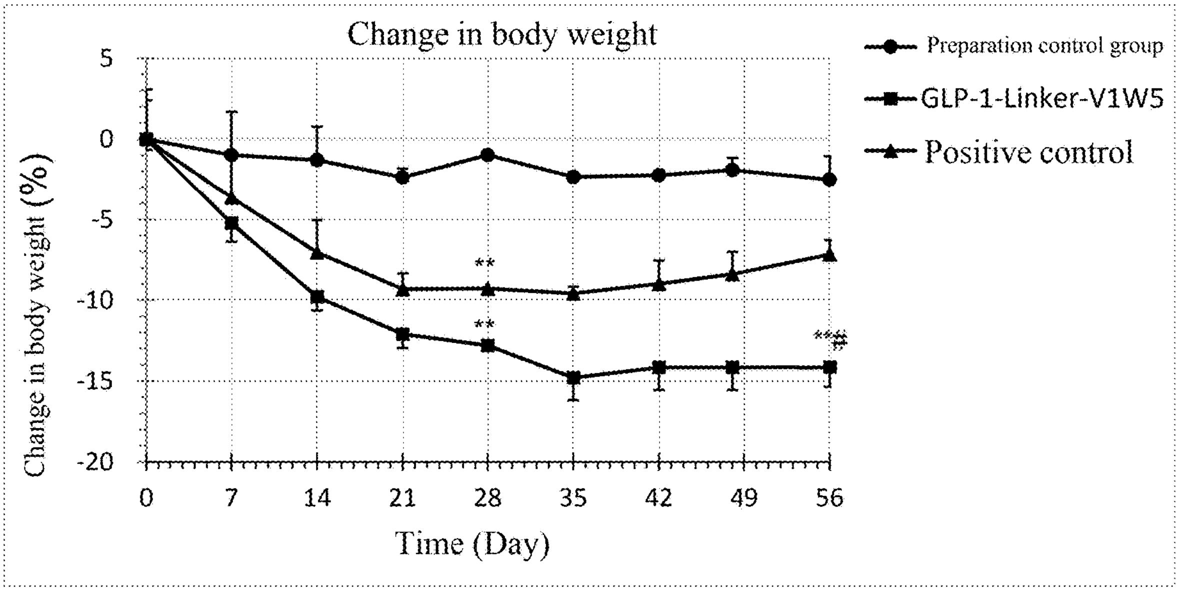
FIG. 13 shows the time curve of the effect of hGIPR antibody/GLP-1 fusion protein on the ratio of body weight change during the efficacy study period in obese cynomolgus macaque induced by high fat diet. Day28: As compared with preparation control group, GLP-1-Linker-V1W5 and positive control groups showed statistical P value of 0.000 and 0.003, respectively; Day 56: As compared with GLP-1-Linker-V1W5 group, vehicle and positive control groups showed statistical P value of 0.003 and 0.028, respectively.
Figure 14:
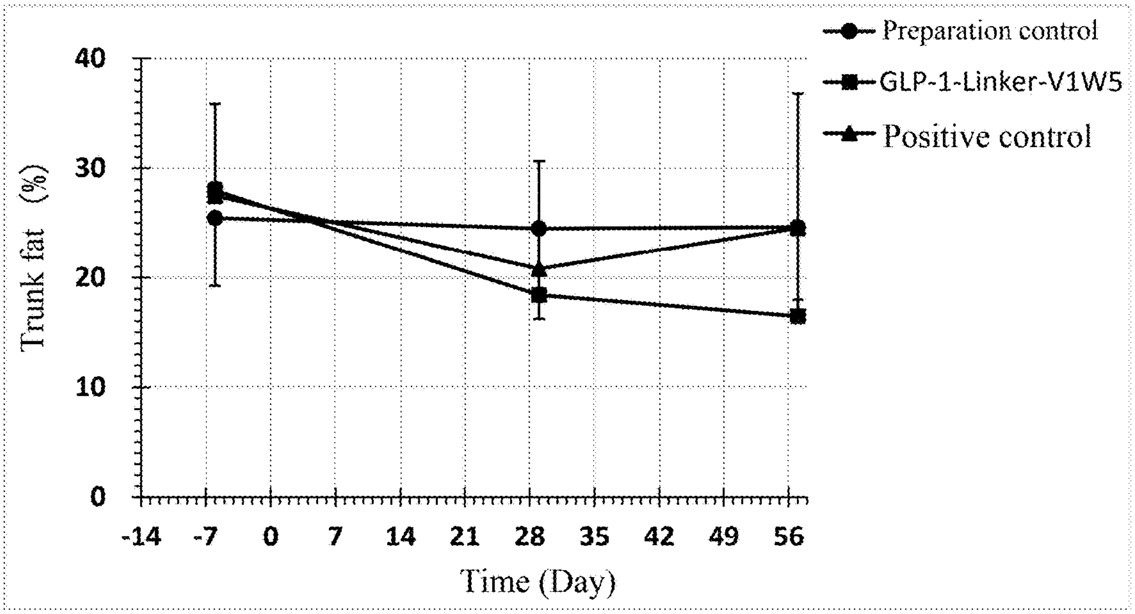
FIG. 14 shows the time curve of the effect of hGIPR antibody/GLP-1 fusion protein on trunk fat change during the efficacy study period in obese cynomolgus macaque induced by high fat diet.
Figure 15:
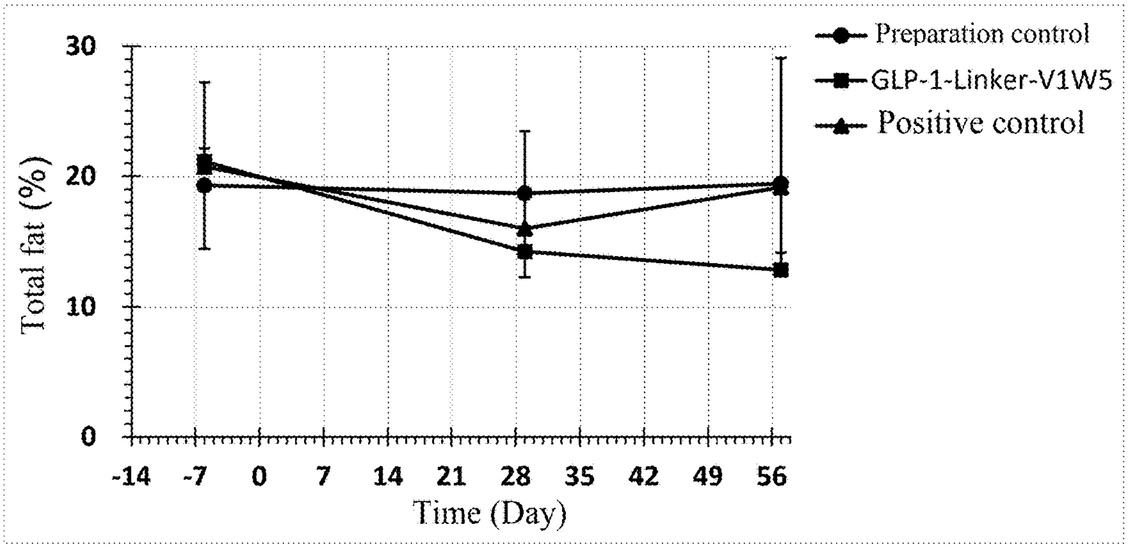
FIG. 15 shows the time curve of the effect of hGIPR antibody/GLP-1 fusion protein on total fat change during the efficacy study period in obese cynomolgus macaque induced by high fat diet.
Figure 16:
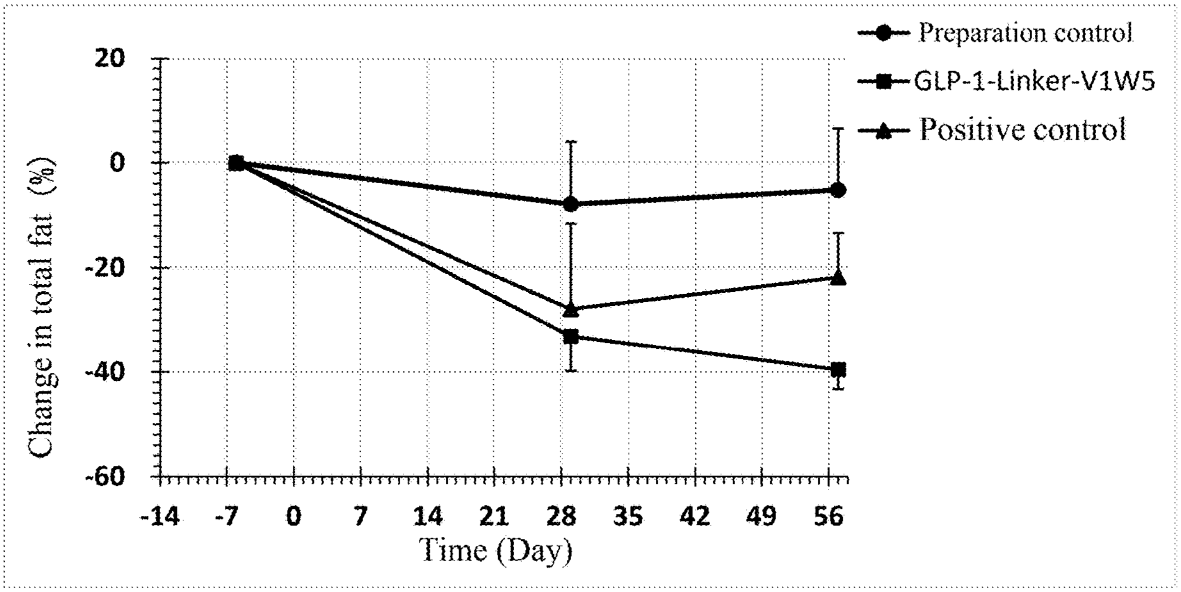
FIG. 16 shows the time curve of the effect of hGIPR antibody/GLP-1 fusion protein on the ratio of total fat change during the efficacy study period in obese cynomolgus macaque induced by high fat diet.
Figure 17:
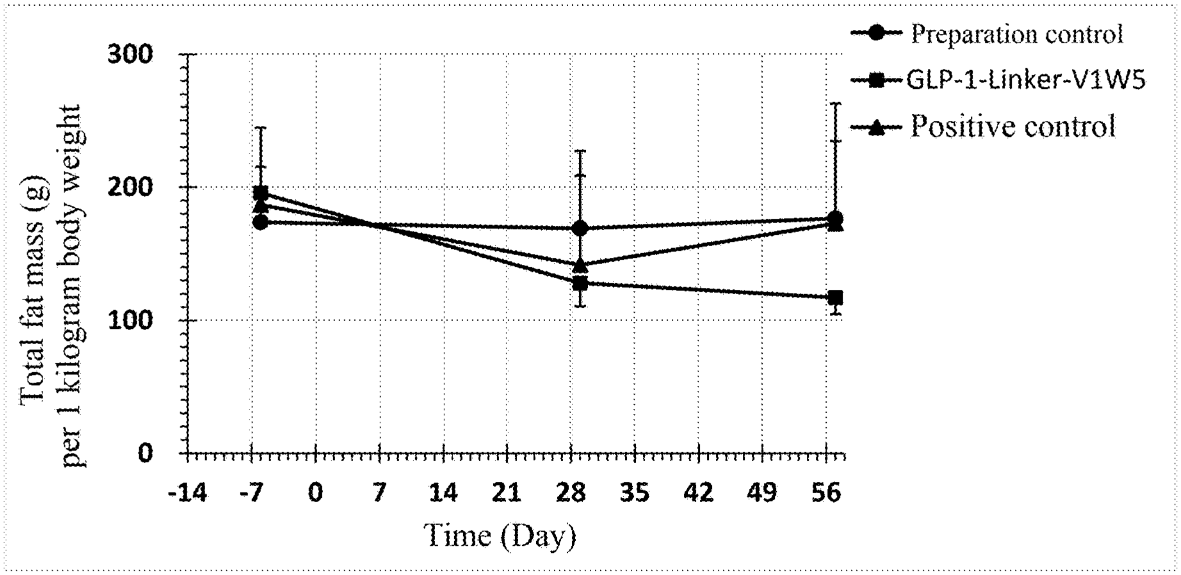
FIG. 17 shows the time curve of the effect of hGIPR antibody/GLP-1 fusion protein on the change of total fat mass per one kilogram body weight during the efficacy study period in obese cynomolgus macaque induced by high fat diet.
Figure 18:
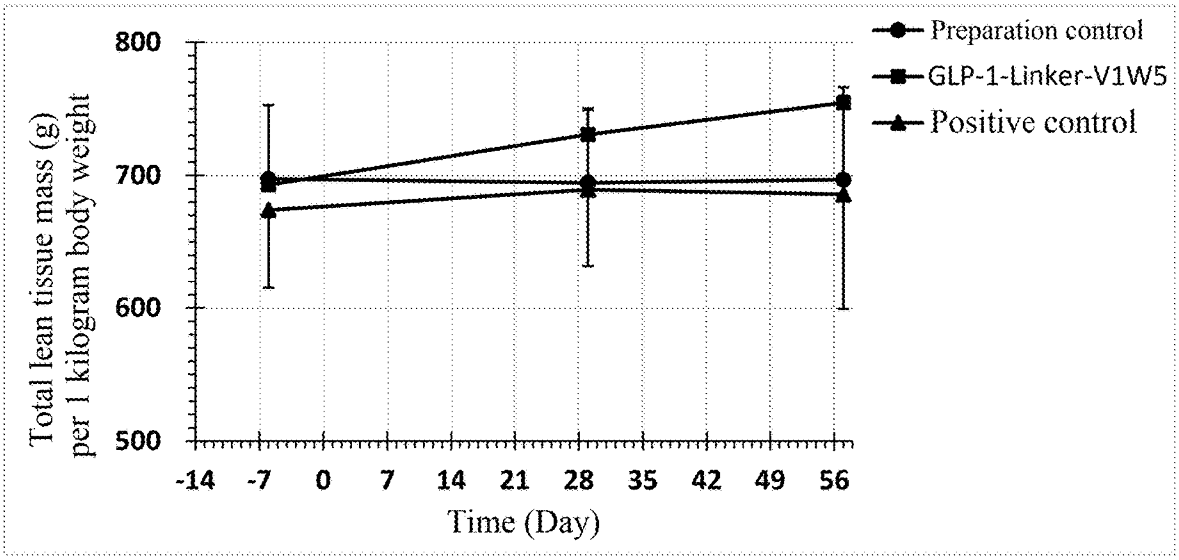
FIG. 18 shows the time curve of the effect of hGIPR antibody/GLP-1 fusion protein on the change of total lean tissue mass per one kilogram body weight during the efficacy study period in obese cynomolgus macaque induced by high fat diet.

The methods described above was used for determination of GLP-1-Linker-V1W5. Nine obese cynomolgus monkeys were randomly divided into preparation control group, GLP-1-Linker-V1W5 group and positive control (use of a fusion protein of GLP-1R antibody and GLP-1) group, three monkeys per group. The drug was injected subcutaneously twice per week for a total of 8 weeks, with 1 mg/kg at the first week and 2 mg/kg from the second week, and the preparation control group was given equal volume of blank formulation. During the study, the data of food intake of monkeys (FIG. 11), the body weight and the calculated body weight change (FIGS. 12 and 13), behavioral observation, blood routine examination/blood biochemistry test and DEXA test were collected, including the time curves of trunk fat change and total fat change (FIGS. 14 and 15), and the time curve of the ratio of total fat change (FIG. 16); While FIG. 17 showed the time curve of the change of total fat mass per one kilogram body weight of monkeys, and FIG. 18 showed the time curve of the change of total lean tissue mass per one kilogram body weight of monkeys.

The efficacy study showed that GLP-1-Linker-V1W5 reduced animals' food intake, further significantly reduced the body weight of obese cynomolgus monkeys, and more importantly, GLP-1-Linker-V1W5 reduced the total fat and trunk fat of obese cynomolgus monkeys while increased lean tissue mass of monkeys, as compared with preparation control and fusion protein of GLP-1R antibody and GLP-1. Meanwhile, no abnormal observations in terms of behavioral observation, blood routine examination and blood biochemistry test.

At study termination, animal livers were biopsied, and liver TP, TG and TC were detected (results are shown in Table 5). The result of liver biochemical test of different groups showed that GLP-1-Linker-V1W5 reduced the liver TC content.

TABLE 5

The result of liver biochemical test of different groups after treatment

| Biochemical Parameters | Preparation control | GLP-1-Linker-V1W5 | GMA102 |
|---|---|---|---|
| TP (g/L) | 5.25 ± 0.55 | 3.95 ± 0.65 | 4.60 ± 0.20 |
| TG (mmol/L) | 2.44 ± 1.01 | 2.11 ± 0.47 | 2.82 ± 1.19 |
| TC (mmol/L) | 0.83 ± 0.18 | 0.33 ± 0.04 | 1.11 ± 0.50 |

TABLE 5-continued

The result of liver biochemical test of different groups after treatment

| Biochemical Parameters | Preparation control | GLP-1-Linker-V1W5 | GMA102 |
|---|---|---|---|
| TG (mmol/g protein) | 0.45 ± 0.14 | 0.57 ± 0.21 | 0.60 ± 0.23 |
| TC (mmol/g protein) | 0.16 ± 0.02 | 0.08 ± 0.00 | 0.24 ± 0.10 |

Note:
mean ± standard error

The above embodiments are meant to fully disclose and explain how to make and use the claimed embodiments to one of ordinary skill in the art, and they are not meant to limit the scope of this disclosure. Modifications obvious to those skilled in the art are within the scope of the claims herein. All the publications, patents and patent applications cited in the specifications were incorporated herein as references, just as each of them was specifically and independently incorporated herein as a reference.

What is claimed is:

1. An antibody specifically binding to human gastric inhibitory polypeptide receptor (GIPR), wherein the antibody comprises a combination of light chain amino acid sequence and heavy chain amino acid sequence independently selected from the group consisting of: SEQ ID NO: 125 and SEQ ID NO: 131 (V1W5), SEQ ID NO: 125 and SEQ ID NO: 127 (V1W1), SEQ ID NO: 125 and SEQ ID NO: 128 (V1W2), SEQ ID NO: 125 and SEQ ID NO: 129 (V1W3), SEQ ID NO: 125 and SEQ ID NO: 130 (V1W4), SEQ ID NO: 125 and SEQ ID NO: 132 (V1W6), SEQ ID NO: 125 and SEQ ID NO: 133 (V1W7), SEQ ID NO: 125 and SEQ ID NO: 134 (V1W8), SEQ ID NO: 125 and SEQ ID NO: 135 (V1W9), SEQ ID NO: 126 and SEQ ID NO: 127 (V2W1), SEQ ID NO: 126 and SEQ ID NO: 128 (V2W2), SEQ ID NO: 126 and SEQ ID NO: 129 (V2W3), SEQ ID NO: 126 and SEQ ID NO: 130 (V2W4), SEQ ID NO: 126 and SEQ ID NO: 131 (V2W5), SEQ ID NO: 126 and SEQ ID NO: 132 (V2W6), SEQ ID NO: 126 and SEQ ID NO: 133 (V2W7), SEQ ID NO: 126 and SEQ ID NO: 134 (V2W8), or SEQ ID NO: 126 and SEQ ID NO: 135 (V2W9).

2. The antibody of claim 1, wherein the antibody is GIPR monoclonal antibody.

3. The antibody of claim 1, wherein the antibody has an IC50 approximately 1 nM to 200 nM or 1 nM to 100 nM in reducing the signal transduction of human GIP.

4. A protein construct, comprising the antibody of claim 1 and a GLP-1 fragment or a reverse GLP-1 fragment; wherein the carboxy terminal of the GLP-1 fragment is fused with the amino terminal of a light chain or a heavy chain of the antibody or the amino terminal of the reverse GLP-1 fragment is fused with the carboxy terminal of a light chain or a heavy chain of the antibody, wherein the GLP-1 fragment or the reverse GLP-1 fragment has a length of at least 20 amino acids and has biological activity of binding and activating GLP-1 receptor.

5. The protein construct of claim 4, wherein the protein construct comprises one, two, three, or four GLP-1 fragments, wherein the carboxy terminal of each GLP-1 fragment is fused via a peptide linker with the amino terminal of a light chain or a heavy chain of the antibody.

6. The protein construct of claim 4, wherein the protein construct comprises two GLP-1 fragments, wherein the carboxy terminal of each GLP-1 fragment is fused via a peptide linker with the amino terminal of each light chain of the antibody, or wherein the carboxy terminal of each GLP-1 fragment is fused via a peptide linker with the amino terminal of each heavy chain of the antibody.

7. The protein construct of claim 5, wherein the peptide linker comprises the amino acid sequence independently selected from the group consisting of: SEQ ID NO: 110, SEQ ID NO: 111, and SEQ ID NO: 112.

8. The protein construct of claim 5, wherein each GLP-1 fragment comprises the amino acid sequence of SEQ ID NO: 106.

9. The protein construct of claim 8, wherein each peptide linker comprises the amino acid sequence of SEQ ID NO: 111.

10. The protein construct of claim 4, wherein the protein construct comprises one, two, three, or four reverse GLP-1 fragments, wherein the amino terminal of each reverse GLP-1 fragment is fused via a peptide linker with the carboxy terminal of a light chain or a heavy chain of the antibody.

11. The protein construct of claim 10, wherein the protein construct comprises two reverse GLP-1 fragments, wherein the amino terminal of each reverse GLP-1 fragment is fused via a peptide linker with the carboxy terminal of each light chain of the antibody, or wherein the amino terminal of each reverse GLP-1 fragment is fused via a peptide linker with the carboxy terminal of each heavy chain of the antibody.

12. The protein construct of claim 4, comprising:

(i) a first polypeptide comprising from the N-terminus to C-terminus: the GLP-1 fragment, a peptide linker, and the light chain of the GIPR antibody and (ii) a second polypeptide comprising the heavy chain of the GIPR antibody; wherein the first polypeptide comprises the amino acid sequence of SEQ ID NO: 136, and the second polypeptide comprises the amino acid sequence of SEQ ID NO: 131.

13. The protein construct of claim 4, wherein the carboxy terminal of the GLP-1 fragment is fused to the amino terminal of a light chain of the antibody via a peptide linker: N'-GLP-1-Linker-R-C'; or the carboxy terminal of the GLP-1 fragment is fused to the amino terminal of a heavy chain of the antibody via a peptide linker: N'-GLP-1-Linker-R-C'; wherein: N' represents an amino terminal of the GLP-1 fusion protein polypeptide chain, C' represents a carboxy terminal of the GLP-1 fusion protein polypeptide chain, GLP-1 represents the GLP-1 fragment, and R represents the amino acid sequence of the light chain or heavy chain of the antibody, and Linker represents the polypeptide linker.

14. The protein construct of claim 4, wherein the GLP-1 fragment comprises the amino acid sequence independently selected from the group consisting of: SEQ ID NO: 105, SEQ ID NO: 106, SEQ ID NO: 107, SEQ ID NO: 108, and SEQ ID NO: 109; or wherein the reverse GLP-1 fragment comprises the amino acid sequence independently selected from SEQ ID NO: 119, SEQ ID NO: 120, SEQ ID NO: 121, SEQ ID NO: 122, and SEQ ID NO: 123.

15. A polynucleotide encoding the antibody of claim 1, or the protein construct of claim 4.

16. A vector comprising the polynucleotide of claim 15.

17. A host cell comprising the vector of claim 16.

18. A pharmaceutical composition comprising the antibody of claim 1 or the protein construct of claim 4 mixed with pharmaceutically acceptable carrier.

19. A method for reducing the severity of nonalcoholic fatty liver disease comprising administering the pharmaceutical composition of claim 18 to a patient having the nonalcoholic fatty liver disease.

20. A method for reducing the severity of type 2 diabetes comprising administering the pharmaceutical composition of claim 18 to a patient having type 2 diabetes.

21. A method for losing body weight, comprising administering the pharmaceutical composition of claim 18 to a patient having obesity.

22. A pharmaceutical composition of claim 18, wherein the pharmaceutical composition is to be administrated intravenously or subcutaneously.

* * * * *

SEQUENCE LISTING

```
<160> NUMBER OF SEQ ID NOS: 142

<210> SEQ ID NO 1
<211> LENGTH: 11
<212> TYPE: PRT
<213> ORGANISM: Mus musculus

<400> SEQUENCE: 1

Lys Ala Ser Gln Asp Val Gly Thr Ala Val Ala
1               5                   10


<210> SEQ ID NO 2
<211> LENGTH: 7
<212> TYPE: PRT
<213> ORGANISM: Mus musculus

<400> SEQUENCE: 2

Trp Ala Tyr Ile Arg His Thr
1               5


<210> SEQ ID NO 3
<211> LENGTH: 9
<212> TYPE: PRT
<213> ORGANISM: Mus musculus

<400> SEQUENCE: 3

Gln Gln Tyr Ser Ser Tyr Pro Trp Thr
1               5


<210> SEQ ID NO 4
<211> LENGTH: 15
<212> TYPE: PRT
<213> ORGANISM: Mus musculus

<400> SEQUENCE: 4

Arg Pro Ser Glu Ser Val Asp Ser Tyr Gly Asn Ser Phe Met His
1               5                   10                  15


<210> SEQ ID NO 5
<211> LENGTH: 7
<212> TYPE: PRT
<213> ORGANISM: Mus musculus

<400> SEQUENCE: 5
```

Leu Ala Ser Asn Leu Glu Ser
1 5

<210> SEQ ID NO 6
<211> LENGTH: 9
<212> TYPE: PRT
<213> ORGANISM: Mus musculus

<400> SEQUENCE: 6

Gln Gln Asn Asn Glu Asp Pro Arg Thr
1 5

<210> SEQ ID NO 7
<211> LENGTH: 11
<212> TYPE: PRT
<213> ORGANISM: Mus musculus

<400> SEQUENCE: 7

Lys Ala Ser Glu Asp Ile Tyr Asn Arg Phe Ala
1 5 10

<210> SEQ ID NO 8
<211> LENGTH: 7
<212> TYPE: PRT
<213> ORGANISM: Mus musculus

<400> SEQUENCE: 8

Asp Ala Thr Ser Leu Glu Thr
1 5

<210> SEQ ID NO 9
<211> LENGTH: 9
<212> TYPE: PRT
<213> ORGANISM: Mus musculus

<400> SEQUENCE: 9

Gln Gln Tyr Trp Ser Ile Pro Trp Thr
1 5

<210> SEQ ID NO 10
<211> LENGTH: 15
<212> TYPE: PRT
<213> ORGANISM: Mus musculus

<400> SEQUENCE: 10

Arg Ala Ser Gln Ser Val Asn Thr Ser Val Tyr Ser Tyr Ile His
1 5 10 15

<210> SEQ ID NO 11
<211> LENGTH: 7
<212> TYPE: PRT
<213> ORGANISM: Mus musculus

<400> SEQUENCE: 11

Tyr Ala Ser Asn Leu Glu Ser
1 5

<210> SEQ ID NO 12
<211> LENGTH: 9
<212> TYPE: PRT
<213> ORGANISM: Mus musculus

<400> SEQUENCE: 12

Gln His Ser Trp Asp Phe Pro Tyr Thr 1 5

<210> SEQ ID NO 13
<211> LENGTH: 15
<212> TYPE: PRT
<213> ORGANISM: Mus musculus

<400> SEQUENCE: 13

Arg Ala Ser Gln Ser Val Asn Thr Ala Val Tyr Ser Tyr Ile His
1 5 10 15

<210> SEQ ID NO 14
<211> LENGTH: 9
<212> TYPE: PRT
<213> ORGANISM: Mus musculus

<400> SEQUENCE: 14

Gln His Ser Phe Asp Phe Pro Tyr Thr
1 5

<210> SEQ ID NO 15
<211> LENGTH: 11
<212> TYPE: PRT
<213> ORGANISM: Mus musculus

<400> SEQUENCE: 15

Lys Ala Ser Gln Asp Ile Asn Ser Tyr Leu Ser
1 5 10

<210> SEQ ID NO 16
<211> LENGTH: 6
<212> TYPE: PRT
<213> ORGANISM: Mus musculus

<400> SEQUENCE: 16

Ala Asn Arg Leu Val Asp
1 5

<210> SEQ ID NO 17
<211> LENGTH: 9
<212> TYPE: PRT
<213> ORGANISM: Mus musculus

<400> SEQUENCE: 17

Leu Gln Tyr Asp Glu Phe Pro Phe Thr
1 5

<210> SEQ ID NO 18
<211> LENGTH: 10
<212> TYPE: PRT
<213> ORGANISM: Mus musculus

<400> SEQUENCE: 18

Gly Phe Thr Phe Ser Ser Tyr Ala Met Ser
1 5 10

<210> SEQ ID NO 19
<211> LENGTH: 16
<212> TYPE: PRT
<213> ORGANISM: Mus musculus

<400> SEQUENCE: 19

Ser Ile Ser Ser Gly Gly Ala Thr Tyr Tyr Pro Asp Ser Val Lys Gly
1 5 10 15

<210> SEQ ID NO 20
<211> LENGTH: 13
<212> TYPE: PRT
<213> ORGANISM: Mus musculus

<400> SEQUENCE: 20

Gly Glu Gly Gly Ser Ser Tyr Pro Ala Trp Phe Ala Phe
1 5 10

<210> SEQ ID NO 21
<211> LENGTH: 17
<212> TYPE: PRT
<213> ORGANISM: Mus musculus

<400> SEQUENCE: 21

Glu Ile Ser Ser Gly Gly Ser Tyr Thr Tyr Tyr Pro Asp Thr Val Thr
1 5 10 15

Gly

<210> SEQ ID NO 22
<211> LENGTH: 17
<212> TYPE: PRT
<213> ORGANISM: Mus musculus

<400> SEQUENCE: 22

Asp Lys Ala Thr Arg Thr Gly Met Gly Phe Phe Tyr His Thr Met Asp
1 5 10 15

Tyr

<210> SEQ ID NO 23
<211> LENGTH: 10
<212> TYPE: PRT
<213> ORGANISM: Mus musculus

<400> SEQUENCE: 23

Gly Tyr Thr Phe Ser Arg Tyr Trp Ile Glu
1 5 10

<210> SEQ ID NO 24
<211> LENGTH: 16
<212> TYPE: PRT
<213> ORGANISM: Mus musculus

<400> SEQUENCE: 24

Glu Ile Leu Pro Gly Ser Asp Ser Pro Asn Tyr Asn Glu Lys Phe Lys
1 5 10 15

<210> SEQ ID NO 25
<211> LENGTH: 9
<212> TYPE: PRT
<213> ORGANISM: Mus musculus

<400> SEQUENCE: 25

Thr Val Val Ala Thr Arg Phe Ala Tyr
1 5

<210> SEQ ID NO 26
<211> LENGTH: 11
<212> TYPE: PRT
<213> ORGANISM: Mus musculus

<400> SEQUENCE: 26

Gly Tyr Ser Ile Thr Ser Asp Tyr Ala Trp Asn 1 5 10

<210> SEQ ID NO 27
<211> LENGTH: 16
<212> TYPE: PRT
<213> ORGANISM: Mus musculus

<400> SEQUENCE: 27

Tyr Ile Ser Tyr Arg Gly Ile Ala Thr Tyr Lys Pro Ser Leu Lys Ser
1 5 10 15

<210> SEQ ID NO 28
<211> LENGTH: 10
<212> TYPE: PRT
<213> ORGANISM: Mus musculus

<400> SEQUENCE: 28

Gly Glu Tyr Gly Pro Gly Asn Phe Asp Phe
1 5 10

<210> SEQ ID NO 29
<211> LENGTH: 16
<212> TYPE: PRT
<213> ORGANISM: Mus musculus

<400> SEQUENCE: 29

Tyr Met Ser Tyr Arg Gly Thr Ala Thr Tyr Asn Pro Phe Leu Lys Ser
1 5 10 15

<210> SEQ ID NO 30
<211> LENGTH: 10
<212> TYPE: PRT
<213> ORGANISM: Mus musculus

<400> SEQUENCE: 30

Tyr Asp Tyr Asp Val Pro Arg Phe Pro Tyr
1 5 10

<210> SEQ ID NO 31
<211> LENGTH: 33
<212> TYPE: DNA
<213> ORGANISM: Mus musculus

<400> SEQUENCE: 31
aaggccagtc aggatgtggg tactgctgta gcc 33

<210> SEQ ID NO 32
<211> LENGTH: 21
<212> TYPE: DNA
<213> ORGANISM: Mus musculus

<400> SEQUENCE: 32
tgggcataca tccggcacac t 21

<210> SEQ ID NO 33
<211> LENGTH: 27
<212> TYPE: DNA
<213> ORGANISM: Mus musculus

<400> SEQUENCE: 33
cagcaatata gcagctatcc gtggacg 27

<210> SEQ ID NO 34
<211> LENGTH: 45

<212> TYPE: DNA
<213> ORGANISM: Mus musculus

<400> SEQUENCE: 34
agacccagtg aaagtgttga tagttatggc aatagtttta tgcac 45

<210> SEQ ID NO 35
<211> LENGTH: 21
<212> TYPE: DNA
<213> ORGANISM: Mus musculus

<400> SEQUENCE: 35
cttgcatcca acctagaatc t 21

<210> SEQ ID NO 36
<211> LENGTH: 27
<212> TYPE: DNA
<213> ORGANISM: Mus musculus

<400> SEQUENCE: 36
cagcaaaata atgaggatcc tcggacg 27

<210> SEQ ID NO 37
<211> LENGTH: 33
<212> TYPE: DNA
<213> ORGANISM: Mus musculus

<400> SEQUENCE: 37
aaggcaagtg aggacatata taatcggttc gcc 33

<210> SEQ ID NO 38
<211> LENGTH: 21
<212> TYPE: DNA
<213> ORGANISM: Mus musculus

<400> SEQUENCE: 38
gatgcaacca gtttggaaac t 21

<210> SEQ ID NO 39
<211> LENGTH: 27
<212> TYPE: DNA
<213> ORGANISM: Mus musculus

<400> SEQUENCE: 39
caacagtatt ggagtattcc gtggacg 27

<210> SEQ ID NO 40
<211> LENGTH: 45
<212> TYPE: DNA
<213> ORGANISM: Mus musculus

<400> SEQUENCE: 40
agggccagcc aaagtgtcaa tacatctgtc tatagttata tacac 45

<210> SEQ ID NO 41
<211> LENGTH: 21
<212> TYPE: DNA
<213> ORGANISM: Mus musculus

<400> SEQUENCE: 41
tatgcatcca acctagaatc t 21

<210> SEQ ID NO 42

<211> LENGTH: 27
<212> TYPE: DNA
<213> ORGANISM: Mus musculus

<400> SEQUENCE: 42
caacacagtt gggattttcc ttacacg 27

<210> SEQ ID NO 43
<211> LENGTH: 45
<212> TYPE: DNA
<213> ORGANISM: Mus musculus

<400> SEQUENCE: 43
agagccagcc agtccgtgaa cacagccgtg tactcttata tccac 45

<210> SEQ ID NO 44
<211> LENGTH: 27
<212> TYPE: DNA
<213> ORGANISM: Mus musculus

<400> SEQUENCE: 44
cagcacagct tcgatttccc ctacacc 27

<210> SEQ ID NO 45
<211> LENGTH: 33
<212> TYPE: DNA
<213> ORGANISM: Mus musculus

<400> SEQUENCE: 45
aaggcgagtc aggacattaa tagctattta agc 33

<210> SEQ ID NO 46
<211> LENGTH: 18
<212> TYPE: DNA
<213> ORGANISM: Mus musculus

<400> SEQUENCE: 46
gcaaacagat tggtagat 18

<210> SEQ ID NO 47
<211> LENGTH: 27
<212> TYPE: DNA
<213> ORGANISM: Mus musculus

<400> SEQUENCE: 47
ctacagtatg atgagtttcc attcacg 27

<210> SEQ ID NO 48
<211> LENGTH: 30
<212> TYPE: DNA
<213> ORGANISM: Mus musculus

<400> SEQUENCE: 48
ggattcactt tcagtagcta tgccatgtct 30

<210> SEQ ID NO 49
<211> LENGTH: 45
<212> TYPE: DNA
<213> ORGANISM: Mus musculus

<400> SEQUENCE: 49
tccattagta gtggtggtgc cacctactat ccagacagtg tgaag 45

<210> SEQ ID NO 50
<211> LENGTH: 39
<212> TYPE: DNA
<213> ORGANISM: Mus musculus

<400> SEQUENCE: 50
ggcgagggcg gtagtagcta cccggcctgg tttgctttc 39

<210> SEQ ID NO 51
<211> LENGTH: 51
<212> TYPE: DNA
<213> ORGANISM: Mus musculus

<400> SEQUENCE: 51
gaaattagta gtggtggtag ttacacctac tatccagaca ctgtgacggg c 51

<210> SEQ ID NO 52
<211> LENGTH: 51
<212> TYPE: DNA
<213> ORGANISM: Mus musculus

<400> SEQUENCE: 52
gataaggcga ctcgaactgg catgggattt ttttaccata ctatggacta c 51

<210> SEQ ID NO 53
<211> LENGTH: 30
<212> TYPE: DNA
<213> ORGANISM: Mus musculus

<400> SEQUENCE: 53
ggctacacat tcagtaggta ctggatagag 30

<210> SEQ ID NO 54
<211> LENGTH: 51
<212> TYPE: DNA
<213> ORGANISM: Mus musculus

<400> SEQUENCE: 54
gagattttac ctggaagtga tagtcctaac tacaatgaga agttcaaggg c 51

<210> SEQ ID NO 55
<211> LENGTH: 27
<212> TYPE: DNA
<213> ORGANISM: Mus musculus

<400> SEQUENCE: 55
acggtagtag ctacaaggtt tgcttac 27

<210> SEQ ID NO 56
<211> LENGTH: 33
<212> TYPE: DNA
<213> ORGANISM: Mus musculus

<400> SEQUENCE: 56
ggctactcaa tcaccagtga ttatgcctgg aac 33

<210> SEQ ID NO 57
<211> LENGTH: 48
<212> TYPE: DNA
<213> ORGANISM: Mus musculus

<400> SEQUENCE: 57
tacataagct acagaggcat cgctacctat aaaccatctc tcaaaagt 48

<210> SEQ ID NO 58
<211> LENGTH: 30
<212> TYPE: DNA
<213> ORGANISM: Mus musculus

<400> SEQUENCE: 58
ggggaatacg gccccggcaa ctttgacttc 30

<210> SEQ ID NO 59
<211> LENGTH: 48
<212> TYPE: DNA
<213> ORGANISM: Mus musculus

<400> SEQUENCE: 59
tacatgagct accgtggtac cgcaacgtac aatccatttc tcaaaagt 48

<210> SEQ ID NO 60
<211> LENGTH: 30
<212> TYPE: DNA
<213> ORGANISM: Mus musculus

<400> SEQUENCE: 60
tatgattacg acgttccccg gtttccttac 30

<210> SEQ ID NO 61
<211> LENGTH: 108
<212> TYPE: PRT
<213> ORGANISM: Mus musculus

<400> SEQUENCE: 61

Asp Ile Val Met Thr Gln Ser His Lys Phe Met Ser Thr Ser Val Gly
1 5 10 15

Asp Arg Val Asn Ile Thr Cys Lys Ala Ser Gln Asp Val Gly Thr Ala
20 25 30

Val Ala Trp Tyr Gln Gln Lys Pro Gly Gln Ser Pro Lys Leu Leu Ile
35 40 45

Tyr Trp Ala Tyr Ile Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Thr Asp Tyr Phe Cys Gln Gln Tyr Ser Ser Tyr Pro Trp
85 90 95

Thr Phe Gly Gly Gly Thr Lys Leu Glu Ile Lys Arg
100 105

<210> SEQ ID NO 62
<211> LENGTH: 112
<212> TYPE: PRT
<213> ORGANISM: Mus musculus

<400> SEQUENCE: 62

Asn Ile Val Leu Thr Gln Ser Pro Ala Ser Leu Ala Val Ser Leu Gly
1 5 10 15

Gln Arg Ala Thr Ile Ser Cys Arg Pro Ser Glu Ser Val Asp Ser Tyr
20 25 30

Gly Asn Ser Phe Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

```
Arg Phe Ser Gly Ser Gly Ser Gly Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Arg Thr Phe Gly Gly Gly Thr Lys Leu Glu Ile Lys Arg
            100                 105                 110


<210> SEQ ID NO 63
<211> LENGTH: 112
<212> TYPE: PRT
<213> ORGANISM: Artificial Sequence
<220> FEATURE:
<223> OTHER INFORMATION: Synthetic construct

<400> SEQUENCE: 63

Asn Ile Val Leu Thr Gln Ser Pro Ala Ser Leu Ala Val Ser Pro Gly
1               5                   10                  15

Gln Arg Ala Thr Ile Thr Cys Arg Pro Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Asn Asn
                85                  90                  95

Glu Asp Pro Arg Thr Phe Gly Gly Gly Thr Lys Val Glu Ile Lys Arg
            100                 105                 110


<210> SEQ ID NO 64
<211> LENGTH: 112
<212> TYPE: PRT
<213> ORGANISM: Artificial Sequence
<220> FEATURE:
<223> OTHER INFORMATION: Synthetic construct

<400> SEQUENCE: 64

Asn Ile Val Leu Thr Gln Ser Pro Asp Ser Leu Ala Val Ser Leu Gly
1               5                   10                  15

Glu Arg Ala Thr Ile Asn Cys Arg Pro Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110


<210> SEQ ID NO 65
<211> LENGTH: 108
<212> TYPE: PRT
<213> ORGANISM: Mus musculus

<400> SEQUENCE: 65
```

```
Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Phe Ala Trp Phe Gln Gln Lys Pro Gly Asn Ala Pro Arg Leu Leu Ile
        35                  40                  45

Ser Asp Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ile Pro Trp
                85                  90                  95

Thr Phe Gly Gly Gly Thr Lys Leu Glu Ile Lys Arg
            100                 105


<210> SEQ ID NO 66
<211> LENGTH: 112
<212> TYPE: PRT
<213> ORGANISM: Mus musculus

<400> SEQUENCE: 66

Asp Ile Val Leu Thr Gln Ser Pro Ala Ser Leu Ala Val Ser Leu Gly
1               5                   10                  15

Gln Arg Gly Thr Ile Ser Cys Arg Ala Ser Gln Ser Val Asn Thr Ser
            20                  25                  30

Val Tyr Ser Tyr Ile His Trp Tyr Arg Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Gly Glu Asp Ser Ala Thr Tyr Tyr Cys Gln His Ser Trp
                85                  90                  95

Asp Phe Pro Tyr Thr Phe Gly Gly Gly Thr Lys Leu Glu Ile Lys Arg
            100                 105                 110


<210> SEQ ID NO 67
<211> LENGTH: 112
<212> TYPE: PRT
<213> ORGANISM: Artificial Sequence
<220> FEATURE:
<223> OTHER INFORMATION: Synthetic construct

<400> SEQUENCE: 67

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Asn Thr Ala
            20                  25                  30

Val Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Ala Ala Asn Tyr Tyr Cys Gln His Ser Phe
                85                  90                  95

Asp Phe Pro Tyr Thr Phe Gly Gly Gly Thr Lys Val Glu Ile Lys Arg
```

100 105 110

<210> SEQ ID NO 68
<211> LENGTH: 112
<212> TYPE: PRT
<213> ORGANISM: Artificial Sequence
<220> FEATURE:
<223> OTHER INFORMATION: Synthetic construct

<400> SEQUENCE: 68

Asp Ile Val Leu Thr Gln Ser Pro Asp Ser Leu Ala Val Ser Leu Gly
1 5 10 15

Glu Arg Ala Thr Ile Asn Cys Arg Ala Ser Gln Ser Val Asn Thr Ser
20 25 30

Val Tyr Ser Tyr Ile His Trp Tyr Gln Gln Lys Pro Gly Gln Pro Pro
35 40 45

Lys Leu Leu Ile Lys Tyr Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln His Ser Trp
85 90 95

Asp Phe Pro Tyr Thr Phe Gly Gly Gly Thr Lys Val Glu Ile Lys Arg
100 105 110

<210> SEQ ID NO 69
<211> LENGTH: 108
<212> TYPE: PRT
<213> ORGANISM: Mus musculus

<400> SEQUENCE: 69

Asp Ile Lys Met Thr Gln Ser Pro Ser Ser Val Tyr Ala Ser Leu Gly
1 5 10 15

Glu Arg Val Thr Ile Thr Cys Lys Ala Ser Gln Asp Ile Asn Ser Tyr
20 25 30

Leu Ser Trp Phe Gln Gln Lys Pro Gly Lys Ser Pro Lys Thr Leu Ile
35 40 45

Tyr Arg Ala Asn Arg Leu Val Asp Gly Val Pro Ser Arg Phe Ser Gly
50 55 60

Ser Gly Ser Gly Gln Asp Tyr Ser Leu Thr Ile Ser Ser Leu Glu Tyr
65 70 75 80

Glu Asp Met Gly Ile Tyr Tyr Cys Leu Gln Tyr Asp Glu Phe Pro Phe
85 90 95

Thr Phe Gly Ser Gly Thr Lys Leu Glu Met Lys Arg
100 105

<210> SEQ ID NO 70
<211> LENGTH: 110
<212> TYPE: PRT
<213> ORGANISM: Homo sapiens

<400> SEQUENCE: 70

Ser Tyr Val Leu Thr Gln Pro Pro Ser Ala Ser Gly Thr Pro Gly Gln
1 5 10 15

Arg Val Ala Ile Ser Cys Ser Gly Ser Asn Ser Asn Ile Gly Ser Asn
20 25 30

Thr Val His Trp Tyr Gln Gln Leu Pro Gly Ala Ala Pro Lys Leu Leu
35 40 45

```
Ile Tyr Ser Asn Asn Gln Arg Pro Ser Gly Val Pro Asp Arg Phe Ser
    50                  55                  60

Gly Ser Asn Ser Gly Thr Ser Ala Ser Leu Ala Ile Ser Arg Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Val Thr Val Leu
            100                 105                 110


<210> SEQ ID NO 71
<211> LENGTH: 110
<212> TYPE: PRT
<213> ORGANISM: Homo sapiens

<400> SEQUENCE: 71

Ser Tyr Val Leu Thr Gln Pro Pro Ser Ala Ser Gly Thr Pro Gly Gln
1               5                   10                  15

Arg Val Ala Ile Ser Cys Ser Gly Ser Asn Ser Asn Ile Gly Ser Asn
            20                  25                  30

Thr Val His Trp Tyr Gln Gln Leu Pro Gly Ala Ala Pro Lys Leu Leu
        35                  40                  45

Ile Tyr Gly Asn Asn Asp Arg Pro Ser Gly Val Pro Asp Arg Phe Ser
    50                  55                  60

Gly Ser Asn Ser Gly Thr Ser Ala Ser Leu Ala Ile Ser Arg Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Val Thr Val Leu
            100                 105                 110


<210> SEQ ID NO 72
<211> LENGTH: 121
<212> TYPE: PRT
<213> ORGANISM: Mus musculus

<400> SEQUENCE: 72

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Leu Thr Pro Glu Lys Arg Leu Glu Trp Val
        35                  40                  45

Ala Ser Ile Ser Ser Gly Gly Ala Thr Tyr Tyr Pro Asp Ser Val Lys
    50                  55                  60

Gly Arg Phe Thr Phe Ser Arg Asp Asn Ala Arg Asn Ile Leu Tyr Leu
65                  70                  75                  80

Gln Met Asn Ser Leu Arg Ser Glu Asp Thr Ala Met Tyr Tyr Cys Thr
                85                  90                  95

Arg Gly Glu Gly Gly Ser Ser Tyr Pro Ala Trp Phe Ala Phe Trp Gly
            100                 105                 110

Gln Gly Thr Leu Val Thr Val Ser Ala
        115                 120


<210> SEQ ID NO 73
<211> LENGTH: 126
<212> TYPE: PRT
<213> ORGANISM: Mus musculus
```

<400> SEQUENCE: 73

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Val Arg Asp Lys Ala Thr Arg Thr Gly Met Gly Phe Phe Tyr His Thr
            100                 105                 110

Met Asp Tyr Trp Gly Gln Gly Thr Ser Val Thr Val Ser Ser
        115                 120                 125
```

<210> SEQ ID NO 74
<211> LENGTH: 126
<212> TYPE: PRT
<213> ORGANISM: Artificial Sequence
<220> FEATURE:
<223> OTHER INFORMATION: Synthetic construct

<400> SEQUENCE: 74

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Lys Ala Thr Arg Thr Gly Met Gly Phe Phe Tyr His Thr
            100                 105                 110

Met Asp Tyr Trp Gly Gln Gly Thr Leu Val Thr Val Ser Ser
        115                 120                 125
```

<210> SEQ ID NO 75
<211> LENGTH: 118
<212> TYPE: PRT
<213> ORGANISM: Mus musculus

<400> SEQUENCE: 75

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Asp Ser Pro Asn Tyr Asn Glu Lys Phe
    50                  55                  60
```

```
Lys Gly Lys Ala Thr Phe Thr Ala Asn Thr Ser Ser Asn Thr Ala Tyr
65                  70                  75                  80

Met Gln Leu Ser Ser Leu Thr Phe Glu Asp Ser Ala Val Tyr Tyr Cys
                85                  90                  95

Ala Arg Thr Val Val Ala Thr Arg Phe Ala Tyr Trp Gly Gln Gly Thr
            100                 105                 110

Leu Val Thr Val Phe Ala
        115


<210> SEQ ID NO 76
<211> LENGTH: 119
<212> TYPE: PRT
<213> ORGANISM: Mus musculus

<400> SEQUENCE: 76

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Ser Ile Thr Arg Asp Thr Ser Lys Asn Gln Phe Phe
65                  70                  75                  80

Leu Asn Phe Asn Ser Val Thr Thr Glu Asp Thr Ala Thr Tyr Tyr Cys
                85                  90                  95

Val Arg Gly Glu Tyr Gly Pro Gly Asn Phe Asp Phe Trp Gly Gln Gly
            100                 105                 110

Thr Thr Leu Thr Val Ser Ser
        115


<210> SEQ ID NO 77
<211> LENGTH: 119
<212> TYPE: PRT
<213> ORGANISM: Artificial Sequence
<220> FEATURE:
<223> OTHER INFORMATION: Synthetic construct

<400> SEQUENCE: 77

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser
        115
```

<210> SEQ ID NO 78
<211> LENGTH: 119
<212> TYPE: PRT
<213> ORGANISM: Mus musculus

<400> SEQUENCE: 78

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Met Ser Tyr Arg Gly Thr Ala Thr Tyr Asn Pro Phe Leu
    50                  55                  60

Lys Ser Arg Ile Ser Ile Asn Arg Asp Thr Ser Lys Asn Gln Val Phe
65                  70                  75                  80

Leu Lys Leu Asn Ser Val Thr Thr Glu Asp Thr Ala Thr Tyr Tyr Cys
                85                  90                  95

Ala Ser Tyr Asp Tyr Asp Val Pro Arg Phe Pro Tyr Trp Gly Gln Gly
            100                 105                 110

Thr Leu Val Ile Val Ser Ala
        115
```

<210> SEQ ID NO 79
<211> LENGTH: 119
<212> TYPE: PRT
<213> ORGANISM: Homo sapiens

<400> SEQUENCE: 79

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Thr Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gln Gly Pro Ile Val Gly Ala Pro Thr Asp Tyr Trp Gly Lys Gly
            100                 105                 110

Thr Leu Val Thr Val Ser Ser
        115
```

<210> SEQ ID NO 80
<211> LENGTH: 119
<212> TYPE: PRT
<213> ORGANISM: Homo sapiens

<400> SEQUENCE: 80

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Lys Ser Tyr
            20                  25                  30

Ala Ile Ser Trp Val Arg Gln Ala Pro Gly Gln Gly Leu Glu Trp Met
```

```
        35                  40                  45

Gly Gly Ile Ile Pro Thr Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gln Gly Pro Ile Val Gly Ala Pro Thr Asp Tyr Trp Gly Lys Gly
            100                 105                 110

Thr Leu Val Thr Val Ser Ser
        115


<210> SEQ ID NO 81
<211> LENGTH: 324
<212> TYPE: DNA
<213> ORGANISM: Mus musculus

<400> SEQUENCE: 81

gacattgtga tgacccagtc tcacaaattc atgtccacat cagtaggaga cagggtcaac     60

atcacctgca aggccagtca ggatgtgggt actgctgtag cctggtatca acagaaacca    120

gggcaatctc ctaaactact gatttactgg gcatacatcc ggcacactgg agtccctgat    180

cgcttcacag gcagtggatc tgggacagat ttcactctca ccattagcaa tgtgcagtct    240

gaagacttga cagattattt ctgtcagcaa tatagcagct atccgtggac gttcggtgga    300

ggcaccaagc tggaaatcaa acgg                                           324


<210> SEQ ID NO 82
<211> LENGTH: 336
<212> TYPE: DNA
<213> ORGANISM: Mus musculus

<400> SEQUENCE: 82

aacattgtgc tgacccaatc tccagcttct ttggctgtgt ctctagggca gagggccacc     60

atatcctgca gacccagtga aagtgttgat agttatggca atagttttat gcactggtac    120

cagcagaaac caggacagcc acccaaactc ctcatctatc ttgcatccaa cctagaatct    180

ggggtccctg ccaggttcag tggcagtggg tctgggacag acttcaccct caccattgat    240

cctgtggagg ctgatgatgc tgcaacctat tactgtcagc aaaataatga ggatcctcgg    300

acgttcggtg gaggcaccaa gctggaaatc aaacgg                               336


<210> SEQ ID NO 83
<211> LENGTH: 336
<212> TYPE: DNA
<213> ORGANISM: Artificial Sequence
<220> FEATURE:
<223> OTHER INFORMATION: Synthetic construct

<400> SEQUENCE: 83

aatatcgtgc tgacccagtc tccagccagc ctggccgtgt ctccaggaca gagggccacc     60

atcacatgca gacctagcga gtccgtggat tcctacggca actctttcat gcactggtat    120

cagcagaagc ccggccagcc ccctaagctg ctgatctacc tggccagcaa tctggagtcc    180

ggagtgcctg caaggttctc tggaagcgga tccggaaccg actttaccct gacaatcaac    240

ccagtggagg ccaacgatac agccaattac tattgtcagc agaacaatga ggacccacgg    300

acctttggcg gaggaacaaa ggtggagatc aagcgt                               336
```

<210> SEQ ID NO 84
<211> LENGTH: 336
<212> TYPE: DNA
<213> ORGANISM: Artificial Sequence
<220> FEATURE:
<223> OTHER INFORMATION: Synthetic construct

<400> SEQUENCE: 84
aacatcgtgc tgacccagtc cccagactct ctggccgtgt ccctgggaga gagggccaca 60
atcaactgca gaccctctga gagcgtggat agctacggca attccttcat gcactggtat 120
cagcagaagc ctggccagcc ccctaagctg ctgatctacc tggcctctaa tctggagagc 180
ggcgtgccag acaggttctc cggatctgga agcggaaccg acttcaccct gacaatcagc 240
tccctgcagg cagaggacgt ggccgtgtac tattgtcagc agaacaatga ggatccccgg 300
acctttggcg gcggcacaaa ggtggagatc aagcgt 336

<210> SEQ ID NO 85
<211> LENGTH: 324
<212> TYPE: DNA
<213> ORGANISM: Mus musculus

<400> SEQUENCE: 85
gacatccaga tgacacaatc ttcatcctcc ttttctgtat ctctaggaga cagagtcacc 60
attacttgca aggcaagtga ggacatatat aatcggttcg cctggtttca gcagaaacca 120
ggaaatgctc ctaggctctt aatatctgat gcaaccagtt tggaaactgg ggttccttca 180
agattcagtg gcagtggatc tggaaaggat tacactctca gcattaccag tcttcagact 240
gaagatgttg ctacttatta ctgtcaacag tattggagta ttccgtggac gttcggtgga 300
ggcaccaagc tggaaatcaa acgg 324

<210> SEQ ID NO 86
<211> LENGTH: 336
<212> TYPE: DNA
<213> ORGANISM: Mus musculus

<400> SEQUENCE: 86
gacattgtgc tgacacagtc tcctgcttcc ttagctgtat ctctggggca gaggggcacc 60
atctcatgca gggccagcca aagtgtcaat acatctgtct atagttatat acactggtac 120
cggcagaaac caggtcagcc acccaaactc ctcatcaagt atgcatccaa cctagaatct 180
ggggtccctg ccaggttcag tggcagtggg tctgggacag acttcaccct caacatccat 240
cctgtggagg gggaggattc cgcaacatac tactgtcaac acagttggga ttttccttac 300
acgttcggag gggggaccaa gctggaaata aaacgg 336

<210> SEQ ID NO 87
<211> LENGTH: 336
<212> TYPE: DNA
<213> ORGANISM: Artificial Sequence
<220> FEATURE:
<223> OTHER INFORMATION: Synthetic construct

<400> SEQUENCE: 87
gacatcgtgc tgacccagtc tccagccagc ctggccgtgt ctccaggaca gagggccacc 60
atcacatgca gagccagcca gtccgtgaac acagccgtgt actcttatat ccactggtac 120
cagcagaagc ctggccagcc ccctaagctg ctgatcaagt atgccagcaa cctggagtcc 180
ggagtgcctg cacggttctc tggaagcgga tccggaaccg acttcaccct gacaatcaat 240
ccagtggagg ccaacgacgc cgccaattac tattgtcagc acagcttcga tttcccctac 300
acctttggcg gcggcacaaa ggtggagatc aagcgt 336

<210> SEQ ID NO 88
<211> LENGTH: 336
<212> TYPE: DNA
<213> ORGANISM: Artificial Sequence
<220> FEATURE:
<223> OTHER INFORMATION: Synthetic construct

<400> SEQUENCE: 88
gacatcgtgc tgacccagtc ccctgattct ctggccgtgt ccctgggaga gagggcaacc 60
atcaactgca gagcctctca gagcgtgaat acaagcgtgt actcctatat ccactggtac 120
cagcagaagc caggccagcc ccctaagctg ctgatcaagt atgcctctaa cctggagagc 180
ggagtgccag accggttctc cggctctggc agcggcacag acttcaccct gacaatcagc 240
tccctgcagg cagaggacgt ggccgtgtac tattgtcagc actcttggga tttcccctac 300
acctttggcg gcggcacaaa ggtggagatc aagcgt 336

<210> SEQ ID NO 89
<211> LENGTH: 324
<212> TYPE: DNA
<213> ORGANISM: Mus musculus

<400> SEQUENCE: 89
gacatcaaga tgacccagtc tccatcttcc gtgtatgcat ctctaggaga gagagtcact 60
atcacttgca aggcgagtca ggacattaat agctatttaa gctggttcca gcagaaacca 120
gggaaatctc ctaagaccct gatctatcgt gcaaacagat tggtagatgg ggtcccatca 180
aggttcagtg gcagtggatc tggcaagat tattctctca ccatcagcag cctggagtat 240
gaagatatgg gaatttatta ttgtctacag tatgatgagt ttccattcac gttcggctcg 300
gggacaaagt tggaaatgaa acgg 324

<210> SEQ ID NO 90
<211> LENGTH: 330
<212> TYPE: DNA
<213> ORGANISM: Homo sapiens

<400> SEQUENCE: 90
agctacgtgc tgacccagcc acctagcgcc tccggaacac caggccagag ggtggccatc 60
tcttgcagcg gctccaactc taatatcggc tccaacaccg tgcactggta ccagcagctg 120
ccaggagcag cacccaagct gctgatctat tccaacaatc agcggccttc tggcgtgcca 180
gacagattca gcggctccaa ctctggcaca agcgcctccc tggccatctc tcggctgcag 240
agcgaggacg aggccgatta ctattgtgcc gcctgggacg attctctgaa tggcgtggtg 300
tttggcggcg gcaccaaggt gacagtgctg 330

<210> SEQ ID NO 91
<211> LENGTH: 330
<212> TYPE: DNA
<213> ORGANISM: Homo sapiens

<400> SEQUENCE: 91
agctacgtgc tgacccagcc acctagcgcc tccggaacac caggccagag ggtggccatc 60
tcttgcagcg gctccaactc taatatcggc tccaacaccg tgcactggta tcagcagctg 120

```
ccaggagcag cacccaagct gctgatctat ggcaacaatg atcggccttc tggcgtgcca    180

gacagattca gcggctccaa ctctggcaca agcgcctccc tggccatctc tcggctgcag    240

agcgaggacg aggccgatta ctattgtgcc gcctgggacg attctctgaa tggcgtggtg    300

tttggcggcg gtaccaaggt gacagtgctg                                     330
```

```
<210> SEQ ID NO 92
<211> LENGTH: 363
<212> TYPE: DNA
<213> ORGANISM: Mus musculus

<400> SEQUENCE: 92

gaagtgaagc tggtggagtc tgggggaggc ttagtgaagc ctggagggtc cctgaaactc     60

tcctgtgcag cctctggatt cactttcagt agctatgcca tgtcttgggt tcgcctgact    120

ccagaaaaaa ggctggagtg ggtcgcatcc attagtagtg gtggtgccac ctactatcca    180

gacagtgtga agggccgatt caccttctcc agagataatg ccaggaacat cctgtacctg    240

caaatgaaca gtctgaggtc tgaggacacg gccatgtatt actgtacaag aggcgagggc    300

ggtagtagct acccggcctg gtttgctttc tggggccaag ggactctggt cactgtctct    360

gca                                                                  363
```

```
<210> SEQ ID NO 93
<211> LENGTH: 378
<212> TYPE: DNA
<213> ORGANISM: Mus musculus

<400> SEQUENCE: 93

gaagtgcagc tggtggagtc tgggggaggc ttagtgaagc ctggagggtc cctgaaactc     60

tcctgtgcag cctctggatt cactttcagt agctatgcca tgtcttgggt tcgccagtct    120

ccagagaaga ggctggagtg ggtcgcagaa attagtagtg gtggtagtta cacctactat    180

ccagacactg tgacgggccg attcaccatc tccagagaca atgccaagaa caccctgtac    240

ctggaaatga gcagtctgag gtctgaggac acggccatgt attactgtgt aagggataag    300

gcgactcgaa ctggcatggg attttttttac catactatgg actactgggg tcaaggaacc    360

tcagtcaccg tctcctca                                                  378
```

```
<210> SEQ ID NO 94
<211> LENGTH: 378
<212> TYPE: DNA
<213> ORGANISM: Artificial Sequence
<220> FEATURE:
<223> OTHER INFORMATION: Synthetic construct

<400> SEQUENCE: 94

gaggtgcagc tggtggagtc tggaggagga ctggtgaagc caggaggaag cctgaggctg     60

tcctgcgcag cctctggctt cacctttagc tcctacgcca tgagctgggt gaggcaggca    120

ccaggcaagg gactggagtg ggtggccgag atctctagcg gcggctccta cacctactat    180

cctgacaccg tgacaggccg gttcacaatc agcagagata acgccaagaa ttccctgtat    240

ctgcagatga actctctgcg ggccgaggac accgccgtgt actattgcgt gcgggataag    300

gccacccgca caggcatggg cttcttttac cacacaatgg actattgggg ccagggcacc    360

ctggtgacag tgtcctct                                                  378
```

```
<210> SEQ ID NO 95
<211> LENGTH: 354
```

<212> TYPE: DNA
<213> ORGANISM: Mus musculus

<400> SEQUENCE: 95
caggttcaac tgcagcagtc tggagctgag ctgatgaagc ctggggcctc agtgaagata 60
tcctgcaagg ctactggcta cacattcagt aggtactgga tagagtggat aaagcagagg 120
cctggacatg gccttgagtg gattggagag attttacctg gaagtgatag tcctaactac 180
aatgagaagt tcaagggcaa ggccacattc actgcaaata catcctccaa cacagcctac 240
atgcaactca gcagcctgac atttgaggac tctgccgtct attactgtgc aagaacggta 300
gtagctacaa ggtttgctta ctggggccaa gggactctgg tcactgtctt tgca 354

<210> SEQ ID NO 96
<211> LENGTH: 357
<212> TYPE: DNA
<213> ORGANISM: Mus musculus

<400> SEQUENCE: 96
gatgtgcagc ttcaggagtc gggacctggc ctggtgaaac cttctcagtc tctgtccctc 60
acctgcactg tcactggcta ctcaatcacc agtgattatg cctggaactg gatccggcag 120
tttcctggaa acaaagtgga gtggatgggc tacataagct acagaggcat cgctacctat 180
aaaccatctc tcaaaagtcg aatctctatc actcgagaca catccaagaa ccagttcttc 240
ctgaacttta attctgtgac tactgaggac acagccacat attactgtgt aagaggggaa 300
tacggccccg gcaactttga cttctggggc caaggcacca ctctcacagt ctcctca 357

<210> SEQ ID NO 97
<211> LENGTH: 357
<212> TYPE: DNA
<213> ORGANISM: Artificial Sequence
<220> FEATURE:
<223> OTHER INFORMATION: Synthetic construct

<400> SEQUENCE: 97
caggtgcagc tgcaggagtc cggaccagga ctggtgaagc caagccagac cctgtccctg 60
acctgcacag tgtccggcta ctctatcaca agcgattatg cctggaactg gatcaggcag 120
ccacctggca agggagtgga gtggatgggc tacatctcct atcgcggcat cgccacctac 180
aagccttccc tgaagtctcg gatcaccatc tctagagaca caagcaagaa ccagttctct 240
ctgaagctga gctccgtgac cgccgccgat acagccgtgt actattgcgt gcggggcgag 300
tatggccccg gcaatttcga cttttggggc cagggcacca cagtgacagt gtctagc 357

<210> SEQ ID NO 98
<211> LENGTH: 357
<212> TYPE: DNA
<213> ORGANISM: Mus musculus

<400> SEQUENCE: 98
gatgtgcagc ttcaagagtc gggacctggc ctggtgaaac cttctcagtc tctgtccctc 60
acctgcactg tcactggcta ctcaatcacc agtgattatg cctggaactg gatccggcag 120
tttccaggaa acaaactgga gtggatgggc tacatgagct accgtggtac cgcaacgtac 180
aatccatttc tcaaaagtcg aatctctatc aatcgggaca catccaagaa ccaggtcttc 240
ctgaagttga attctgtgac tactgaggac acagccacat attactgtgc aagttatgat 300
tacgacgttc cccggtttcc ttactggggc caagggactc tggtcattgt ttctgca 357

<210> SEQ ID NO 99
<211> LENGTH: 357
<212> TYPE: DNA
<213> ORGANISM: Homo sapiens

<400> SEQUENCE: 99
caggtgcagc tgcagcagag cggagcagag gtgaagaagc caggaagctc cgtgaaggtg 60
tcctgcaagg cctctggcgg caccttctct agctacgcca tctcctgggt gcggcaggca 120
ccaggacagg gactggagtg gatgggagga atcatcccca ccttcggcac agccaactac 180
gcccagaagt ttcagggccg ggtgaccatc acagccgacg agtctaccag cacagcctat 240
atggagctgt cctctctgag atctgaggat accgccgtgt actattgtgc acagggacca 300
atcgtgggag cacctacaga ctattggggc aagggcaccc tggtgacagt gagctcc 357

<210> SEQ ID NO 100
<211> LENGTH: 357
<212> TYPE: DNA
<213> ORGANISM: Homo sapiens

<400> SEQUENCE: 100
caggtgcagc tgcagcagag cggagcagag gtgaagaagc caggaagctc cgtgaaggtg 60
tcctgcaagg cctctggcgg caccttcaag agctacgcca tctcctgggt gcggcaggca 120
ccaggacagg gactggagtg gatgggagga atcatcccca ccttcggcac agccaactac 180
gcccagaagt ttcagggccg ggtgaccatc acagccgacg agtctaccag cacagcctat 240
atggagctgt cctctctgag atctgaggat accgccgtgt actattgtgc acagggacca 300
atcgtgggag cacctacaga ctattggggc aagggcaccc tggtgacagt gagctcc 357

<210> SEQ ID NO 101
<211> LENGTH: 106
<212> TYPE: PRT
<213> ORGANISM: Homo sapiens

<400> SEQUENCE: 101

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 102
<211> LENGTH: 106
<212> TYPE: PRT
<213> ORGANISM: Homo sapiens

<400> SEQUENCE: 102

Gly Gln Pro Lys Ala Ala Pro Ser Val Thr Leu Phe Pro Pro Ser Ser
1 5 10 15

```
Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 103
<211> LENGTH: 326
<212> TYPE: PRT
<213> ORGANISM: Homo sapiens
<220> FEATURE:
<221> NAME/KEY: MISC_FEATURE
<222> LOCATION: (131)..(131)
<223> OTHER INFORMATION: Xaa at position 131 is Met or Tyr
<220> FEATURE:
<221> NAME/KEY: MISC_FEATURE
<222> LOCATION: (133)..(133)
<223> OTHER INFORMATION: Xaa at position 133 is Ser or Thr
<220> FEATURE:
<221> NAME/KEY: MISC_FEATURE
<222> LOCATION: (135)..(135)
<223> OTHER INFORMATION: Xaa at position 135 is Thr or Glu
<220> FEATURE:
<221> NAME/KEY: MISC_FEATURE
<222> LOCATION: (307)..(307)
<223> OTHER INFORMATION: Xaa at position 307 is Met or Leu
<220> FEATURE:
<221> NAME/KEY: MISC_FEATURE
<222> LOCATION: (313)..(313)
<223> OTHER INFORMATION: Xaa at position 313 is Asn or Ser
<220> FEATURE:
<221> NAME/KEY: MISC_FEATURE
<222> LOCATION: (326)..(326)
<223> OTHER INFORMATION: Xaa at position 326 is Lys or does not exist

<400> SEQUENCE: 103

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Xaa Ile Xaa Arg Xaa Pro Glu Val Thr Cys Val Val Val Asp
    130                 135                 140

Val Ser His Glu Asp Pro Glu Val Gln Phe Asn Trp Tyr Val Asp Gly
```

```
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Xaa His Glu Ala Leu His Xaa His Tyr Thr Gln Lys Ser Leu
305                 310                 315                 320

Ser Leu Ser Pro Gly Xaa
                325


<210> SEQ ID NO 104
<211> LENGTH: 327
<212> TYPE: PRT
<213> ORGANISM: Homo sapiens
<220> FEATURE:
<221> NAME/KEY: MISC_FEATURE
<222> LOCATION: (132)..(132)
<223> OTHER INFORMATION: Xaa at position 132 is Met or Tyr
<220> FEATURE:
<221> NAME/KEY: MISC_FEATURE
<222> LOCATION: (134)..(134)
<223> OTHER INFORMATION: Xaa at position 134 is Ser or Thr
<220> FEATURE:
<221> NAME/KEY: MISC_FEATURE
<222> LOCATION: (136)..(136)
<223> OTHER INFORMATION: Xaa at position 136 is Thr or Glu
<220> FEATURE:
<221> NAME/KEY: MISC_FEATURE
<222> LOCATION: (308)..(308)
<223> OTHER INFORMATION: Xaa at position 308 is Met or Leu
<220> FEATURE:
<221> NAME/KEY: MISC_FEATURE
<222> LOCATION: (314)..(314)
<223> OTHER INFORMATION: Xaa at position 314 is Asn or Ser
<220> FEATURE:
<221> NAME/KEY: MISC_FEATURE
<222> LOCATION: (327)..(327)
<223> OTHER INFORMATION: Xaa at position 327 is Lys or does not exist

<400> SEQUENCE: 104

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Xaa Ile Xaa Arg Xaa Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Xaa His Glu Ala Leu His Xaa His Tyr Thr Gln Lys Ser
305                 310                 315                 320

Leu Ser Leu Ser Leu Gly Xaa
                325
```

<210> SEQ ID NO 105
<211> LENGTH: 29
<212> TYPE: PRT
<213> ORGANISM: Homo sapiens

<400> SEQUENCE: 105

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25
```

<210> SEQ ID NO 106
<211> LENGTH: 29
<212> TYPE: PRT
<213> ORGANISM: Artificial Sequence
<220> FEATURE:
<223> OTHER INFORMATION: Synthetic construct

<400> SEQUENCE: 106

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
```

```
            20                  25


<210> SEQ ID NO 107
<211> LENGTH: 22
<212> TYPE: PRT
<213> ORGANISM: Artificial Sequence
<220> FEATURE:
<223> OTHER INFORMATION: Synthetic construct

<400> SEQUENCE: 107

His Gly Glu Gly Thr Phe Thr Ser Asp Val Ser Ser Tyr Leu Glu Gly
1               5                   10                  15

Gln Ala Ala Lys Glu Phe
            20


<210> SEQ ID NO 108
<211> LENGTH: 23
<212> TYPE: PRT
<213> ORGANISM: Artificial Sequence
<220> FEATURE:
<223> OTHER INFORMATION: Synthetic construct

<400> SEQUENCE: 108

His Gly Glu Gly Thr Phe Thr Ser Asp Val Ser Ser Tyr Leu Glu Gly
1               5                   10                  15

Gln Ala Ala Lys Glu Phe Ile
            20


<210> SEQ ID NO 109
<211> LENGTH: 24
<212> TYPE: PRT
<213> ORGANISM: Artificial Sequence
<220> FEATURE:
<223> OTHER INFORMATION: Synthetic construct

<400> SEQUENCE: 109

His Gly Glu Gly Thr Phe Thr Ser Asp Val Ser Ser Tyr Leu Glu Gly
1               5                   10                  15

Gln Ala Ala Lys Glu Phe Ile Ala
            20


<210> SEQ ID NO 110
<211> LENGTH: 10
<212> TYPE: PRT
<213> ORGANISM: Artificial Sequence
<220> FEATURE:
<223> OTHER INFORMATION: Synthetic construct

<400> SEQUENCE: 110

Gly Gly Gly Gly Ser Gly Gly Gly Gly Ser
1               5                   10


<210> SEQ ID NO 111
<211> LENGTH: 15
<212> TYPE: PRT
<213> ORGANISM: Artificial Sequence
<220> FEATURE:
<223> OTHER INFORMATION: Synthetic construct

<400> SEQUENCE: 111

Gly Gly Gly Gly Ser Gly Gly Gly Gly Ser Gly Gly Gly Gly Ser
1               5                   10                  15


<210> SEQ ID NO 112
<211> LENGTH: 20
```

<212> TYPE: PRT
<213> ORGANISM: Artificial Sequence
<220> FEATURE:
<223> OTHER INFORMATION: Synthetic construct

<400> SEQUENCE: 112

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 113
<211> LENGTH: 466
<212> TYPE: PRT
<213> ORGANISM: Homo sapiens

<400> SEQUENCE: 113

```
Met Thr Thr Ser Pro Ile Leu Gln Leu Leu Leu Gly Leu Ser Leu Cys
1               5                   10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Arg Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
            180                 185                 190

Leu Leu Pro Arg Pro Gly Pro Tyr Leu Gly Asp Gln Ala Leu Ala Leu
        195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
            260                 265                 270

Pro Trp Val Ile Val Arg Tyr Leu Tyr Glu Asn Thr Gln Cys Trp Glu
        275                 280                 285

Arg Asn Glu Val Lys Ala Ile Trp Trp Ile Ile Arg Thr Pro Ile Leu
    290                 295                 300

Met Thr Ile Leu Ile Asn Phe Leu Ile Phe Ile Arg Ile Leu Gly Ile
```

```
305                 310                 315                 320

Leu Leu Ser Lys Leu Arg Thr Arg Gln Met Arg Cys Arg Asp Tyr Arg
                325                 330                 335

Val Arg Leu Ala Arg Ser Thr Leu Thr Leu Val Pro Leu Leu Gly Val
            340                 345                 350

His Glu Val Val Phe Ala Pro Val Thr Glu Glu Gln Ala Arg Gly Ala
        355                 360                 365

Leu Arg Phe Ala Lys Leu Gly Phe Glu Ile Phe Leu Ser Ser Phe Gln
    370                 375                 380

Gly Phe Leu Val Ser Val Leu Tyr Cys Phe Ile Asn Lys Glu Val Gln
385                 390                 395                 400

Ser Glu Ile Arg Arg Gly Trp His His Cys Arg Leu Arg Arg Ser Leu
                405                 410                 415

Gly Glu Glu Gln Arg Gln Leu Pro Glu Arg Ala Phe Arg Ala Leu Pro
            420                 425                 430

Ser Gly Ser Gly Pro Gly Glu Val Pro Thr Ser Arg Gly Leu Ser Ser
        435                 440                 445

Gly Thr Leu Pro Gly Pro Gly Asn Glu Ala Ser Arg Glu Leu Glu Ser
    450                 455                 460

Tyr Cys
465


<210> SEQ ID NO 114
<211> LENGTH: 1401
<212> TYPE: DNA
<213> ORGANISM: Homo sapiens

<400> SEQUENCE: 114

atgactacct ctccgatcct gcagctgctg ctcgggctct cactgtgcgg gctgctgctc     60

cagagggcgg agacaggctc taaggggcag actgcggggg agctgtacca gcgctgggaa    120

cggtaccgca gggagtgcca ggagaccttg gcagccgcgg aaccgccttc aggcctcgcc    180

tgtaacgggt ccttcgatat gtacgtctgc tgggactatg ctgcacccaa tgccactgcc    240

cgtgcgtcct gcccctggta cctgccctgg caccaccatg tggctgcagg tttcgtcctc    300

cgccagtgtc ggagtgatgg ccaatgggga ctttggagag accatacaca atgtgagaac    360

ccagagaaga atgaggcctt tctggaccaa aggctcatct tggagcggtt gcaggtcatg    420

tacactgtcg gctactccct gtctctcgcc acactgctgc tagccctgct catcttgagt    480

ttgttcaggc ggctacattg cactagaaac tatatccaca tcaacctgtt cacgtctttc    540

atgctgcgag ctgcggccat tctcagccga gaccgtctgc tacctcgacc tggcccctac    600

cttggggacc aggcccttgc gctgtggaac caggccctcg ctgcctgccg cacggcccag    660

atcgtgaccc agtactgcgt gggtgccaac tacacgtggc tgctggtgga gggcgtctac    720

ctgcacagtc tcctggtgct cgtgggaggc tccgaggagg gccacttccg ctactacctg    780

ctcctcggct ggggggcccc cgcgcttttc gtcattccct gggtgatcgt caggtacctg    840

tacgagaaca cgcagtgctg ggagcgcaac gaagtcaagg ccatttggtg gattatacgg    900

acccccatcc tcatgaccat cttgattaat ttcctcattt ttatccgcat tcttggcatt    960

ctcctgtcca agctgaggac acggcaaatg cgctgccggg attaccgcgt gaggctggct   1020

cgctccacgc tgacgctggt gcccctgctg ggtgtccacg aggtggtgtt tgctcccgtg   1080

acagaggaac aggcccgggg cgccctgcgt ttcgccaagc tcggctttga gatcttcctc   1140

agctccttcc agggcttcct ggtcagcgtc ctctactgct tcatcaacaa ggaggtgcag   1200
```

tcggagatcc gccgtggctg gcaccactgc cgcctgcgcc gcagcctggg cgaggagcaa 1260
cgccagctcc cggagcgcgc cttccgggcc ctgccctccg gctccggccc gggcgaggtc 1320
cccaccagcc gcggcttgtc ctcggggacc ctcccagggc ctgggaatga ggccagccgg 1380
gagttggaaa gttactgcta g 1401

<210> SEQ ID NO 115
<211> LENGTH: 466
<212> TYPE: PRT
<213> ORGANISM: Macaca mulatta

<400> SEQUENCE: 115

Met Thr Thr Ser Pro Ile Leu Gln Leu Leu Leu Arg Leu Ser Leu Trp
1 5 10 15

Gly Leu Leu Leu Arg Arg Ala Glu Thr Gly Ser Glu Gly Gln Thr Ala
20 25 30

Gly Glu Leu Tyr Gln Arg Trp Glu Arg Tyr Arg Arg Glu Cys Gln Glu
35 40 45

Thr Leu Ala Thr Ala Glu Pro Pro Ser Gly Leu Ala Cys Asn Gly Ser
50 55 60

Phe Asp Met Tyr Val Cys Trp Asn Tyr Ala Ala Pro Asn Ala Thr Ala
65 70 75 80

Arg Ala Ser Cys Pro Trp Tyr Leu Pro Trp His His His Val Ala Ala
85 90 95

Gly Phe Val Leu Arg Gln Cys Gly Ser Asp Gly Gln Trp Gly Leu Trp
100 105 110

Arg Asp His Thr Gln Cys Glu Asn Pro Glu Lys Asn Glu Ala Phe Leu
115 120 125

Asp Gln Arg Leu Ile Leu Glu Arg Leu Gln Val Met Tyr Thr Val Gly
130 135 140

Tyr Ser Leu Ser Leu Ala Thr Leu Leu Leu Ala Leu Leu Ile Leu Ser
145 150 155 160

Leu Phe Arg Arg Leu His Cys Thr Arg Asn Tyr Ile His Ile Asn Leu
165 170 175

Phe Thr Ser Phe Thr Leu Arg Ala Ala Ala Ile Leu Ser Arg Asp Arg
180 185 190

Leu Leu Pro Arg Pro Gly Pro Tyr Leu Gly Asp Gln Ala Leu Val Leu
195 200 205

Trp Asn Gln Ala Leu Ala Ala Cys Arg Thr Ala Gln Ile Val Thr Gln
210 215 220

Tyr Cys Val Gly Ala Asn Tyr Thr Trp Leu Leu Val Glu Gly Val Tyr
225 230 235 240

Leu His Ser Leu Leu Val Ile Val Gly Gly Ser Glu Glu Gly His Phe
245 250 255

Arg Tyr Tyr Leu Leu Leu Gly Trp Gly Ala Pro Ala Leu Phe Val Ile
260 265 270

Pro Trp Val Ile Val Arg Tyr Leu Tyr Glu Asn Thr Gln Cys Trp Glu
275 280 285

Arg Asn Glu Val Lys Ala Ile Trp Trp Ile Ile Arg Thr Pro Ile Leu
290 295 300

Met Thr Ile Leu Ile Asn Phe Leu Ile Phe Ile Arg Ile Leu Gly Ile
305 310 315 320

Leu Leu Ser Lys Leu Arg Thr Arg Gln Met Arg Cys Arg Asp Tyr Arg
325 330 335

Leu Arg Leu Ala Arg Ser Thr Leu Thr Leu Val Pro Leu Leu Gly Val
340 345 350

His Glu Val Val Phe Ala Pro Val Thr Glu Glu Gln Ala Arg Gly Ala
355 360 365

Leu Arg Phe Ala Lys Leu Gly Phe Glu Ile Phe Leu Ser Ser Phe Gln
370 375 380

Gly Leu Leu Val Ser Val Leu Tyr Cys Phe Ile Asn Lys Glu Val Gln
385 390 395 400

Ser Glu Ile Arg Arg Gly Trp His His Cys Arg Leu Arg Arg Ser Leu
405 410 415

Gly Glu Glu Gln Arg Gln Leu Pro Glu Arg Ala Phe Arg Ala Leu Pro
420 425 430

Ser Gly Ser Gly Pro Gly Glu Val Pro Thr Gly Arg Gly Leu Ser Ser
435 440 445

Gly Thr Leu Pro Gly Pro Gly Asn Glu Ala Arg Arg Val Leu Glu Ser
450 455 460

Tyr Cys
465

<210> SEQ ID NO 116
<211> LENGTH: 1398
<212> TYPE: DNA
<213> ORGANISM: Macaca mulatta

<400> SEQUENCE: 116
atgactacct ctccgatcct gcagttgctg ttgcggctct cactgtgggg gctgctgctc 60
cggagggcgg agacaggctc tgaggggcag acggcggggg agctgtacca gcgctgggaa 120
cggtaccgca gggagtgcca ggagaccttg gcaaccgcgg aaccaccttc aggcctcgcc 180
tgtaacgggt ccttcgatat gtacgtctgc tggaactatg ctgcacccaa cgccactgcc 240
cgtgcctcct gcccctggta cctgccctgg caccaccacg tggctgcagg tttcgtcctc 300
cgccagtgtg gcagtgatgg ccagtgggga ctttggagag accacacaca atgtgagaac 360
ccagagaaga atgaggcctt tctggaccaa aggctcatct tggagcggct gcaggtcatg 420
tacaccgtcg gctactccct gtctctcgcc acactgctgc tagccctgct catcttgagc 480
ttgttcaggc gactacattg cactagaaac tatatccaca tcaacctgtt cacgtctttc 540
acactgcgag cggcggcgat tctcagccgg gaccgtctac tgcctcgacc tggcccctac 600
cttggggacc aggcccttgt gctgtggaac caggccctcg ctgcctgccg cacggcccag 660
atcgtgaccc agtactgcgt gggtgccaac tacacgtggc tgctggtgga gggcgtctac 720
ttgcacagtc tcctggtgat cgtgggaggc tccgaggagg gtcacttccg ctactacctg 780
ctcctcggct ggggggcccc cgcgcttttc gtcattccct gggtgatcgt caggtacctg 840
tacgagaaca cgcagtgctg ggagcgcaac gaagtcaagg ccatttggtg gattatacgg 900
acccccatcc tcatgaccat cttgattaat ttcctcattt ttatccgcat tcttggcatt 960
ctcctgtcca agctgaggac acggcaaatg cgctgccggg attaccggct gaggctggct 1020
cgctccacgc tgacgctggt gcccctgctg ggtgtccacg aggtggtgtt tgctcccgtg 1080
accgaggaac aggcccgggg cgccctgcgc ttcgccaagc tcggctttga gatcttcctc 1140
agctctttcc agggcttgct ggtcagcgtc ctctactgct tcatcaacaa ggaggtgcag 1200
tcggagatcc gccgtggctg gcaccactgc cgcctgcgcc gcagcctggg cgaggagcag 1260
cggcagctcc cggagcgcgc cttccgggcc ctgccctccg gctccggccc cggcgaggtc 1320
cccaccggcc gcggcttgtc ttcggggacc ctcccagggc ctgggaatga ggccagacgg 1380
gtgttggaaa gttactgc 1398

<210> SEQ ID NO 117
<211> LENGTH: 460
<212> TYPE: PRT
<213> ORGANISM: Mus musculus

<400> SEQUENCE: 117

Met Pro Leu Arg Leu Leu Leu Leu Leu Leu Trp Leu Trp Gly Leu Gln
1 5 10 15

Trp Ala Glu Thr Asp Ser Glu Gly Gln Thr Thr Thr Gly Glu Leu Tyr
20 25 30

Gln Arg Trp Glu His Tyr Gly Gln Glu Cys Gln Lys Met Leu Glu Thr
35 40 45

Thr Glu Pro Pro Ser Gly Leu Ala Cys Asn Gly Ser Phe Asp Met Tyr
50 55 60

Ala Cys Trp Asn Tyr Thr Ala Ala Asn Thr Thr Ala Arg Val Ser Cys
65 70 75 80

Pro Trp Tyr Leu Pro Trp Phe Arg Gln Val Ser Ala Gly Phe Val Phe
85 90 95

Arg Gln Cys Gly Ser Asp Gly Gln Trp Gly Ser Trp Arg Asp His Thr
100 105 110

Gln Cys Glu Asn Pro Glu Lys Asn Gly Ala Phe Gln Asp Gln Thr Leu
115 120 125

Ile Leu Glu Arg Leu Gln Ile Met Tyr Thr Val Gly Tyr Ser Leu Ser
130 135 140

Leu Thr Thr Leu Leu Leu Ala Leu Leu Ile Leu Ser Leu Phe Arg Arg
145 150 155 160

Leu His Cys Thr Arg Asn Tyr Ile His Met Asn Leu Phe Thr Ser Phe
165 170 175

Met Leu Arg Ala Ala Ala Ile Leu Thr Arg Asp Gln Leu Leu Pro Pro
180 185 190

Leu Gly Pro Tyr Thr Gly Asp Gln Ala Pro Thr Pro Trp Asn Gln Ala
195 200 205

Leu Ala Ala Cys Arg Thr Ala Gln Ile Met Thr Gln Tyr Cys Val Gly
210 215 220

Ala Asn Tyr Thr Trp Leu Leu Val Glu Gly Val Tyr Leu His His Leu
225 230 235 240

Leu Val Ile Val Gly Arg Ser Glu Lys Gly His Phe Arg Cys Tyr Leu
245 250 255

Leu Leu Gly Trp Gly Ala Pro Ala Leu Phe Val Ile Pro Trp Val Ile
260 265 270

Val Arg Tyr Leu Arg Glu Asn Thr Gln Cys Trp Glu Arg Asn Glu Val
275 280 285

Lys Ala Ile Trp Trp Ile Ile Arg Thr Pro Ile Leu Ile Thr Ile Leu
290 295 300

Ile Asn Phe Leu Ile Phe Ile Arg Ile Leu Gly Ile Leu Val Ser Lys
305 310 315 320

Leu Arg Thr Arg Gln Met Arg Cys Pro Asp Tyr Arg Leu Arg Leu Ala
325 330 335

Arg Ser Thr Leu Thr Leu Val Pro Leu Leu Gly Val His Glu Val Val
340 345 350

```
Phe Ala Pro Val Thr Glu Glu Gln Val Glu Gly Ser Leu Arg Phe Ala
        355                 360                 365

Lys Leu Ala Phe Glu Ile Phe Leu Ser Ser Phe Gln Gly Phe Leu Val
    370                 375                 380

Ser Val Leu Tyr Cys Phe Ile Asn Lys Glu Val Gln Ser Glu Ile Arg
385                 390                 395                 400

Gln Gly Trp Arg His Arg Arg Leu Arg Leu Ser Leu Gln Glu Gln Arg
                405                 410                 415

Pro Arg Pro His Gln Glu Leu Ala Pro Arg Ala Val Pro Leu Ser Ser
            420                 425                 430

Ala Cys Arg Glu Ala Ala Val Gly Asn Ala Leu Pro Ser Gly Met Leu
        435                 440                 445

His Val Pro Gly Asp Glu Val Leu Glu Ser Tyr Cys
    450                 455                 460


<210> SEQ ID NO 118
<211> LENGTH: 1380
<212> TYPE: DNA
<213> ORGANISM: Mus musculus

<400> SEQUENCE: 118

atgcccctgc ggttgctgct tctgctgctg tggttgtggg gactccagtg ggcggagaca     60

gactctgagg ggcagaccac cacgggggag ctgtaccagc gctgggagca ctacggccag    120

gagtgccaaa agatgttgga gaccacagaa cctccctcag gcctggcctg taacggttcc    180

ttcgatatgt atgcctgctg gaactacacg gccgccaaca ccactgctcg ggtgtcttgc    240

ccctggtatc tgccctggtt ccgtcaggtg tctgcaggct ttgtcttccg ccagtgtggc    300

agtgatggcc agtggggatc ttggagagac cacactcagt gtgagaatcc agagaagaat    360

ggggcttttc aggaccagac gctgatcctg gagcgcctgc agatcatgta taccgtgggc    420

tactccctgt ccctgacgac tctgctgcta gccctactca tcttaagttt gttcaggcgg    480

ctgcactgca ctcgtaatta cattcacatg aacctgttca cgtctttcat gctgcgggca    540

gcagccatcc tcacccgaga tcagctgctg cctccactgg gtccctacac tggagaccag    600

gcccctaccc cgtggaacca ggccctagct gcctgccgca cggcccagat catgacccaa    660

tattgtgtgg gagccaatta cacctggcta ctggtggagg gtgtttatct gcaccatctg    720

ctggtgatcg tgggacgctc agaaaagggc cacttccgct gctacctgct tcttggctgg    780

ggggcccccg cgcttttcgt cattccctgg gtgatcgtca ggtacctgcg cgagaacaca    840

cagtgctggg agcgcaacga agtcaaagcc atttggtgga tcattcgcac tcccatccta    900

ataaccatct tgatcaattt cctcatcttc atccgcatcc ttggcatcct tgtttcaaag    960

ctgaggacac ggcagatgcg ctgccccgac taccgactaa ggctggctcg ctccacgctg   1020

acactggtgc ccctgctggg tgtccacgag gtggtgtttg cgcctgtgac ggaggaacag   1080

gttgaaggct ccctgcgctt cgccaaactg gcctttgaaa tcttcctaag ttccttccag   1140

ggtttcctgg tgagcgtgct ctactgcttc atcaacaaag aggtgcagtc ggagatccgc   1200

cagggttggc gccaccgccg cctgcgtctc agtcttcaag agcagcgtcc acgtccgcac   1260

caggaactcg ccccccgggc tgtgcctttg agctctgcgt gccgagaagc tgccgttggc   1320

aacgccttgc cctctgggat gctgcatgtg cctggggatg aggtcttgga aagttactgc   1380


<210> SEQ ID NO 119
<211> LENGTH: 29
<212> TYPE: PRT
```

<213> ORGANISM: Homo sapiens

<400> SEQUENCE: 119

```
Gly Lys Val Leu Trp Ala Ile Phe Glu Lys Ala Ala Gln Gly Glu Leu
1               5                   10                  15

Tyr Ser Ser Val Asp Ser Thr Phe Thr Gly Glu Ala His
            20                  25
```

<210> SEQ ID NO 120
<211> LENGTH: 29
<212> TYPE: PRT
<213> ORGANISM: Artificial Sequence
<220> FEATURE:
<223> OTHER INFORMATION: Synthetic construct

<400> SEQUENCE: 120

```
Gly Lys Val Leu Trp Ala Ile Phe Glu Lys Ala Ala Gln Gly Glu Leu
1               5                   10                  15

Tyr Ser Ser Val Asp Ser Thr Phe Thr Gly Glu Gly His
            20                  25
```

<210> SEQ ID NO 121
<211> LENGTH: 22
<212> TYPE: PRT
<213> ORGANISM: Artificial Sequence
<220> FEATURE:
<223> OTHER INFORMATION: Synthetic construct

<400> SEQUENCE: 121

```
Phe Glu Lys Ala Ala Gln Gly Glu Leu Tyr Ser Ser Val Asp Ser Thr
1               5                   10                  15

Phe Thr Gly Glu Gly His
            20
```

<210> SEQ ID NO 122
<211> LENGTH: 23
<212> TYPE: PRT
<213> ORGANISM: Artificial Sequence
<220> FEATURE:
<223> OTHER INFORMATION: Synthetic construct

<400> SEQUENCE: 122

```
Ile Phe Glu Lys Ala Ala Gln Gly Glu Leu Tyr Ser Ser Val Asp Ser
1               5                   10                  15

Thr Phe Thr Gly Glu Gly His
            20
```

<210> SEQ ID NO 123
<211> LENGTH: 24
<212> TYPE: PRT
<213> ORGANISM: Artificial Sequence
<220> FEATURE:
<223> OTHER INFORMATION: Synthetic construct

<400> SEQUENCE: 123

```
Ala Ile Phe Glu Lys Ala Ala Gln Gly Glu Leu Tyr Ser Ser Val Asp
1               5                   10                  15

Ser Thr Phe Thr Gly Glu Gly His
            20
```

<210> SEQ ID NO 124
<211> LENGTH: 327
<212> TYPE: PRT
<213> ORGANISM: Homo sapiens

```
<220> FEATURE:
<221> NAME/KEY: MISC_FEATURE
<222> LOCATION: (132)..(132)
<223> OTHER INFORMATION: Xaa at position 132 is Met or Tyr
<220> FEATURE:
<221> NAME/KEY: MISC_FEATURE
<222> LOCATION: (134)..(134)
<223> OTHER INFORMATION: Xaa at position 134 is Ser or Thr
<220> FEATURE:
<221> NAME/KEY: MISC_FEATURE
<222> LOCATION: (136)..(136)
<223> OTHER INFORMATION: Xaa at position 136 is Thr or Glu
<220> FEATURE:
<221> NAME/KEY: MISC_FEATURE
<222> LOCATION: (308)..(308)
<223> OTHER INFORMATION: Xaa at position 308 is Met or Leu
<220> FEATURE:
<221> NAME/KEY: MISC_FEATURE
<222> LOCATION: (314)..(314)
<223> OTHER INFORMATION: Xaa at position 314 is Asn or Ser
<220> FEATURE:
<221> NAME/KEY: MISC_FEATURE
<222> LOCATION: (327)..(327)
<223> OTHER INFORMATION: Xaa at position 327 is Lys or does not exist

<400> SEQUENCE: 124

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Xaa Ile Xaa Arg Xaa Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
        275                 280                 285

Arg Leu Thr Val Asp Lys Ser Arg Trp Gln Glu Gly Asn Val Phe Ser
    290                 295                 300

Cys Ser Val Xaa His Glu Ala Leu His Xaa His Tyr Thr Gln Lys Ser
305                 310                 315                 320

Leu Ser Leu Ser Leu Gly Xaa
                325


<210> SEQ ID NO 125
<211> LENGTH: 218
<212> TYPE: PRT
<213> ORGANISM: Homo sapiens

<400> SEQUENCE: 125

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Asn Thr Ala
            20                  25                  30

Val Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Ala Ala Asn Tyr Tyr Cys Gln His Ser Phe
                85                  90                  95

Asp Phe Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 126
<211> LENGTH: 218
<212> TYPE: PRT
<213> ORGANISM: Homo sapiens

<400> SEQUENCE: 126

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Asn Thr Ala
            20                  25                  30

Val Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
```

```
    50                  55                  60

Arg Phe Ser Gly Ser Gly Ser Gly Thr Asp Phe Thr Leu Thr Ile Asn
65                  70                  75                  80

Pro Val Glu Ala Asn Asp Ala Ala Asn Tyr Tyr Cys Gln His Ser Phe
                85                  90                  95

Asp Phe Pro Tyr Thr Phe Gly Gly Gly Thr Lys Val Glu Ile Lys Arg
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 127
<211> LENGTH: 445
<212> TYPE: PRT
<213> ORGANISM: Homo sapiens

<400> SEQUENCE: 127

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205
```

```
Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 128
<211> LENGTH: 445
<212> TYPE: PRT
<213> ORGANISM: Homo sapiens

<400> SEQUENCE: 128

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Tyr Ile Thr Arg Glu Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 129
<211> LENGTH: 445
<212> TYPE: PRT
<213> ORGANISM: Homo sapiens

<400> SEQUENCE: 129

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
```

```
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Leu His Glu Ala Leu His Ser
            420                 425                 430

His Tyr Thr Gln Lys Ser Leu Ser Leu Ser Pro Gly Lys
        435                 440                 445
```

<210> SEQ ID NO 130
<211> LENGTH: 445
<212> TYPE: PRT
<213> ORGANISM: Homo sapiens

<400> SEQUENCE: 130

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
```

```
            420                 425                 430

Asn His Tyr Thr Gln Lys Ser Leu Ser Leu Ser Leu Gly
        435                 440                 445


<210> SEQ ID NO 131
<211> LENGTH: 445
<212> TYPE: PRT
<213> ORGANISM: Homo sapiens

<400> SEQUENCE: 131

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350
```

Ser Gln Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Arg Leu Thr Val Asp Lys Ser Arg Trp
405 410 415

Gln Glu Gly Asn Val Phe Ser Cys Ser Val Met His Glu Ala Leu His
420 425 430

Asn His Tyr Thr Gln Lys Ser Leu Ser Leu Ser Leu Gly
435 440 445

<210> SEQ ID NO 132
<211> LENGTH: 445
<212> TYPE: PRT
<213> ORGANISM: Homo sapiens

<400> SEQUENCE: 132

Gln Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Thr Ser Asp
20 25 30

Tyr Ala Trp Asn Trp Ile Arg Gln Pro Pro Gly Lys Gly Val Glu Trp
35 40 45

Met Gly Tyr Ile Ser Tyr Arg Gly Ile Ala Thr Tyr Lys Pro Ser Leu
50 55 60

Lys Ser Arg Ile Thr Ile Ser Arg Asp Thr Ser Lys Asn Gln Phe Ser
65 70 75 80

Leu Lys Leu Ser Ser Val Thr Ala Ala Asp Thr Ala Val Tyr Tyr Cys
85 90 95

Val Arg Gly Glu Tyr Gly Pro Gly Asn Phe Asp Phe Trp Gly Gln Gly
100 105 110

Thr Thr Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Lys Thr Tyr Thr Cys Asn Val Asp His Lys Pro
195 200 205

Ser Asn Thr Lys Val Asp Lys Arg Val Glu Ser Lys Tyr Gly Pro Pro
210 215 220

Cys Pro Pro Cys Pro Ala Pro Glu Ala Ala Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Gln Glu Asp Pro Glu Val
260 265 270

Gln Phe Asn Trp Tyr Val Asp Gly Val Glu Val His Asn Ala Lys Thr
275 280 285

```
Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Leu His Glu Ala Leu His
            420                 425                 430

Ser His Tyr Thr Gln Lys Ser Leu Ser Leu Ser Leu Gly
        435                 440                 445


<210> SEQ ID NO 133
<211> LENGTH: 445
<212> TYPE: PRT
<213> ORGANISM: Homo sapiens

<400> SEQUENCE: 133

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
```

```
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445


<210> SEQ ID NO 134
<211> LENGTH: 445
<212> TYPE: PRT
<213> ORGANISM: Homo sapiens

<400> SEQUENCE: 134

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445


<210> SEQ ID NO 135
<211> LENGTH: 445
<212> TYPE: PRT
<213> ORGANISM: Homo sapiens

<400> SEQUENCE: 135

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Val Glu Trp
        35                  40                  45

Met Gly Tyr Ile Ser Tyr Arg Gly Ile Ala Thr Tyr Lys Pro Ser Leu
    50                  55                  60

Lys Ser Arg Ile Thr Ile Ser Arg Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Val Arg Gly Glu Tyr Gly Pro Gly Asn Phe Asp Phe Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Leu His Glu Ala Leu His
            420                 425                 430

Ser His Tyr Thr Gln Lys Ser Leu Ser Leu Ser Leu Gly
        435                 440                 445
```

<210> SEQ ID NO 136
<211> LENGTH: 262
<212> TYPE: PRT
<213> ORGANISM: Homo sapiens

<400> SEQUENCE: 136

```
His Gly Glu Gly Thr Phe Thr Ser Asp Val Ser Ser Tyr Leu Glu Gly
```

```
1               5                   10                  15

Gln Ala Ala Lys Glu Phe Ile Ala Trp Leu Val Lys Gly Gly Gly Gly
            20                  25                  30

Gly Ser Gly Gly Gly Gly Ser Gly Gly Gly Gly Ser Asp Ile Val Leu
        35                  40                  45

Thr Gln Ser Pro Ala Ser Leu Ala Val Ser Pro Gly Gln Arg Ala Thr
    50                  55                  60

Ile Thr Cys Arg Ala Ser Gln Ser Val Asn Thr Ala Val Tyr Ser Tyr
65                  70                  75                  80

Ile His Trp Tyr Gln Gln Lys Pro Gly Gln Pro Pro Lys Leu Leu Ile
                85                  90                  95

Lys Tyr Ala Ser Asn Leu Glu Ser Gly Val Pro Ala Arg Phe Ser Gly
            100                 105                 110

Ser Gly Ser Gly Thr Asp Phe Thr Leu Thr Ile Asn Pro Val Glu Ala
        115                 120                 125

Asn Asp Ala Ala Asn Tyr Tyr Cys Gln His Ser Phe Asp Phe Pro Tyr
    130                 135                 140

Thr Phe Gly Gly Gly Thr Lys Val Glu Ile Lys Arg Thr Val Ala Ala
145                 150                 155                 160

Pro Ser Val Phe Ile Phe Pro Pro Ser Asp Glu Gln Leu Lys Ser Gly
                165                 170                 175

Thr Ala Ser Val Val Cys Leu Leu Asn Asn Phe Tyr Pro Arg Glu Ala
            180                 185                 190

Lys Val Gln Trp Lys Val Asp Asn Ala Leu Gln Ser Gly Asn Ser Gln
        195                 200                 205

Glu Ser Val Thr Glu Gln Asp Ser Lys Asp Ser Thr Tyr Ser Leu Ser
    210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
            260
```

<210> SEQ ID NO 137
<211> LENGTH: 20
<212> TYPE: DNA
<213> ORGANISM: Artificial Sequence
<220> FEATURE:
<223> OTHER INFORMATION: Synthetic construct

<400> SEQUENCE: 137
tttggrggga agatgaagac 20

<210> SEQ ID NO 138
<211> LENGTH: 21
<212> TYPE: DNA
<213> ORGANISM: Artificial Sequence
<220> FEATURE:
<223> OTHER INFORMATION: Synthetic construct

<400> SEQUENCE: 138
ttaacactct cccctgttga a 21

<210> SEQ ID NO 139
<211> LENGTH: 21
<212> TYPE: DNA
<213> ORGANISM: Artificial Sequence -continued

```
<220> FEATURE:
<223> OTHER INFORMATION: Synthetic construct

<400> SEQUENCE: 139

ttaacactca ttcctgttga a                                               21


<210> SEQ ID NO 140
<211> LENGTH: 21
<212> TYPE: DNA
<213> ORGANISM: Artificial Sequence
<220> FEATURE:
<223> OTHER INFORMATION: Synthetic construct

<400> SEQUENCE: 140

tggacaggga tccagagttc c                                               21


<210> SEQ ID NO 141
<211> LENGTH: 21
<212> TYPE: DNA
<213> ORGANISM: Artificial Sequence
<220> FEATURE:
<223> OTHER INFORMATION: Synthetic construct

<400> SEQUENCE: 141

tggacagggc tccatagttc c                                               21


<210> SEQ ID NO 142
<211> LENGTH: 20
<212> TYPE: DNA
<213> ORGANISM: Artificial Sequence
<220> FEATURE:
<223> OTHER INFORMATION: Synthetic construct

<400> SEQUENCE: 142

actcgtcctt ggtcaacgtg                                                 20
```